(12) United States Patent
Jentsch et al.

(10) Patent No.: US 9,927,423 B2
(45) Date of Patent: Mar. 27, 2018

(54) LRRC8 PROTEINS AND PROTEIN COMPLEXES AND METHODS FOR IDENTIFICATION OF CHANNEL MODULATORS

(71) Applicants: MAX-DELBRUECK-CENTRUM FUER MOLEKULARE MEDIZIN, Berlin (DE); Forschungsverbund Berlin e.V., Berlin (DE)

(72) Inventors: Thomas Jentsch, Berlin (DE); Tobias Stauber, Berlin (DE); Felizia K. Voss, Berlin (DE)

(73) Assignees: FORSCHUNGSVERBUND BERLIN E.V., Berlin (DE); MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 284 days.

(21) Appl. No.: 14/642,776

(22) Filed: Mar. 10, 2015

(65) Prior Publication Data
US 2015/0253303 A1   Sep. 10, 2015

(30) Foreign Application Priority Data

Mar. 10, 2014  (EP) .................................. 14075014
Jun. 17, 2014  (EP) .................................. 14172703

(51) Int. Cl.
*G01N 33/50*    (2006.01)
*G01N 33/68*    (2006.01)
*C07K 14/705*   (2006.01)

(52) U.S. Cl.
CPC ......... *G01N 33/502* (2013.01); *C07K 14/705* (2013.01); *G01N 33/6872* (2013.01); *G01N 2500/10* (2013.01)

(58) Field of Classification Search
CPC ............. G01N 33/502; G01N 33/6872; G01N 2500/10; C07K 14/705
See application file for complete search history.

(56) References Cited

FOREIGN PATENT DOCUMENTS

JP   2004 141048 A   5/2004

OTHER PUBLICATIONS

F. K. Voss et al: "Identification of LRRC8 Heteromers as an Essential Component of the Volume-Regulated Anion Channel VRAC", in: Science, vol. 344, No. 6184, May 9, 2014, pp. 634-638.
Qiu Zhaozhu et al: "SWELL1, a Plasma Membrane Protein, Is an Essential Component of Volume-Regulated Anion Channel", in: Cell, vol. 157, No. 2, Apr. 10, 2014, pp. 447-458.
Akihisa Sawada et al: "A congenital mutation of the novel gene LRRC8 causes agammaglobulinemia in humans" in: Journal of Clinical Investigation, vol. 112, No. 11, Dec. 1, 2003 pp. 1707-1713.
Federico Abascal et al: "LRRC8 proteins share a common ancestor with pannexins, and may form hexameric channels involved in cel1-cel1 communication", in: Bioessays, vol. 34, No. 7, Apr. 25, 2012, pp. 551-560.
Takahiro Hayashi et al: "Factor for Adipocyte Differentiation 158 Gene Disruption Prevents the Body Weight Gain and Insulin Resistance Induced by a High-Fat Diet", in: Biological & Pharmaceutical Bulletin, vol. 34, No. 8, May 27, 2011, pp. 1257-1263.

*Primary Examiner* — Ruixiang Li
(74) *Attorney, Agent, or Firm* — Agris & Von Natzmer, LLP; Joyce Von Natzmer

(57) ABSTRACT

The invention relates to a method for the identification of a channel modulator, such as an agonist or antagonist, that interacts with one or more LRRC8A, LRRC8B, LRRC8C, LRRC8D and/or LRRC8E and/or protein complexes thereof. The invention further relates to an isolated heteromeric protein complex comprising one or more LRRC8A, LRRC8B, LRRC8C, LRRC8D and/or LRRC8E for use in such methods, in addition to kits suitable for carrying out such methods. The invention therefore relate preferably to the use of LRRC8 proteins and complexes thereof for the identification of VRAC (VSOAC) modulators.

11 Claims, 30 Drawing Sheets

- WT HCT116 (n=9)
- LRRC8A + LRRC8C-GFP (n=7)
- LRRC8A + LRRC8D-GFP (n=5)
- LRRC8A + LRRC8E-GFP (n=8)

A

B

G

FLIPR ccd camera image no. 1 (before dispense)

FLIPR ccd camera image no. 9 (end of measurement)

US 9,927,423 B2

LRRC8 PROTEINS AND PROTEIN COMPLEXES AND METHODS FOR IDENTIFICATION OF CHANNEL MODULATORS

CROSS REFERENCE TO RELATED APPLICATION

This application claims priority to European application nos. EP 14075014.2, filed Mar. 10, 2014 and EP 14172703.2, filed on Jun. 17, 2014, which are incorporated herein by reference in their entirety.

INCORPORATION OF SEQUENCE LISTING

This application contains a sequence listing submitted via the USPTO's EFS system and is incorporated herein by reference in its entirety. The sequence listing text file is named "7014-1850-Sequence-Listing", is 5 kilobytes (measured in MS-WINDOWS) and is dated Mar. 5, 2015.

FIELD OF THE INVENTION

The invention relates to a method for the identification of a channel modulator, such as an agonist or antagonist, that interacts with one or more of LRRC8A, LRRC8B, LRRC8C, LRRC8D and/or LRRC8E and/or protein complexes thereof. The invention further relates to an isolated heteromeric protein complex comprising one or more of LRRC8A, LRRC8B, LRRC8C, LRRC8D and/or LRRC8E for use in such methods, in addition to kits suitable for carrying out such methods. The invention therefore relate preferably to the use of LRRC8 proteins and complexes thereof for the identification of VRAC (VSOAC) modulators.

BACKGROUND OF THE INVENTION AND BRIEF INTRODUCTION OF THE INVENTION

Cells regulate their volume not only to counteract swelling or shrinkage caused by osmotic challenges, but also during processes like cell growth, division, and migration. As water transport across cellular membranes is driven by osmotic gradients, cell volume regulation requires appropriate changes of intracellular concentrations of ions or organic osmolytes like taurine (Hoffmann et al., Pasantes-Morales et al.). Regulatory volume decrease (RVD) follows the extrusion of intracellular Cl⁻ and K⁺ ions, as well as other osmolytes, across the plasma membrane. A key player is the volume-regulated anion channel (VRAC) that mediates characteristic swelling-activated Cl⁻ currents ($I_{Cl(swell)}$), and appears to be ubiquitously expressed in vertebrate cells (Nilius et al. 1997, Okada et al. 2009, Okada et al. 1997). Nearly inactive under resting conditions, VRAC is slowly opened by hypotonic swelling. The mechanism by which cell swelling leads to VRAC opening remains enigmatic, with a plethora of studies suggesting a confusingly complex and controversial signal transduction cascade.

VRAC currents are outwardly rectifying (hence the alternative name VSOR for volume stimulated outward rectifier (Okada et al. 2009, Okada et al. 1997)) and show variable inactivation at inside-positive voltages. VRAC conducts iodide better than chloride and is inhibited by several rather non-specific compounds. VRAC might also conduct organic osmolytes like taurine (Jackson et al., Mulligan et al., Roy et al.) (hence the name VSOAC, volume-stimulated organic osmolyte/anion channel (Strange et al.)), but this notion has remained controversial (Lambert et al., Shennan et al., Stutzin et al.). VRAC activity is believed to be not only important for cell volume regulation per se, but also for basic cellular functions like the regulation of cell cycle, proliferation and migration (Hoffmann et al., Nilius et al. 1997, Okada et al. 2009). It is thought to play a role in apoptosis and various pathological states including sickle cell anemia, ischemic brain edema and cancer (Okada et al. 1997, Okada et al. 2006), and VRAC-mediated membrane depolarization may trigger swelling-induced exocytosis (Moser et al.). However, progress in the characterization of VRAC and its biological roles has been severely limited by the failure to identify the underlying protein(s) despite intense efforts for more than two decades.

Hence, the identification of modulators, such as inhibitors or activators, of VRAC could enable the development of medically relevant compounds for potential use in the modulation of medical conditions associated with changes in cell volume, such as those mentioned above.

The lack of specific high-affinity inhibitors of $I_{Cl(swell)}$ has precluded the biochemical identification of VRAC. Expression cloning approaches have been hampered by the ubiquitous expression pattern of the channel, its complex regulation, and potentially by a heteromeric architecture. Nonetheless, several proteins were suggested to embody VRAC. These proteins include the multidrug-resistance (mdr) P-glycoprotein (Valverde et al.) which is a transport ATPase, $pI_{Cln}$, (Paulmichl et al., Fürst et al.) which turned out to be a spliceosome component (Pu et al.), as well as ClC-3 (Duan et al.) which rather is an endosomal anion transporter (Stobrawa et al.). All these claims were disproved by further experimentation (Stobrawa et al., Voets et al., Wine et al., Tominaga et al., Gong et al.). ClC-2 Cl⁻ channels activate upon cell swelling, but their inward rectification and Cl⁻ over I⁻ selectivity deviate from VRAC (Gründer et al.). Drosophila dBest1, a member of a family of bona fide $Ca^{2+}$-activated Cl⁻ channels (Hartzell et al.), mediates swelling-activated Cl⁻ currents in insect cells (Stotz et al., Chien et al.), but their characteristics differ from VRAC currents and the closest mammalian homolog of dBest1 is swelling-insensitive (Fischmeister et al.).

The present invention is based on a structural and functional characterisation of VRAC and its components. VRAC represents a structurally new class of channel that conducts ions and organic osmolytes. The invention relates to a practical utilisation of the VRAC characterisation shown herein, in order to provide methods and compounds used for identifying VRAC modulators in addition to the VRAC components themselves.

BRIEF DESCRIPTION OF THE FIGURES

The invention is further described by the figures. The figures provide particular and/or preferred embodiments of the invention described herein that do not limit the scope of the invention.

SHORT DESCRIPTION OF THE FIGURES

Figure 1:
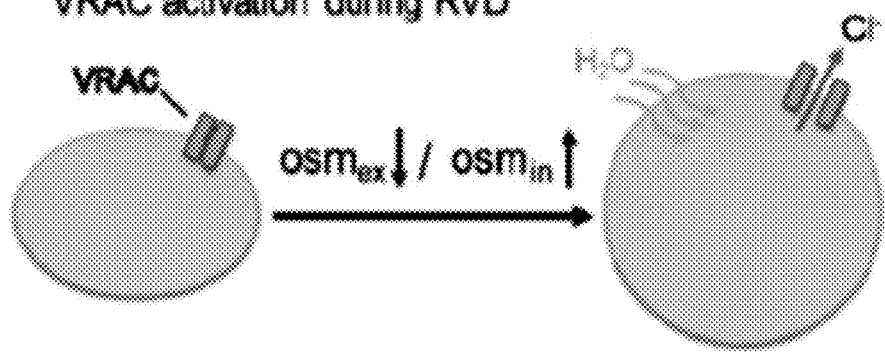
Figure 1:
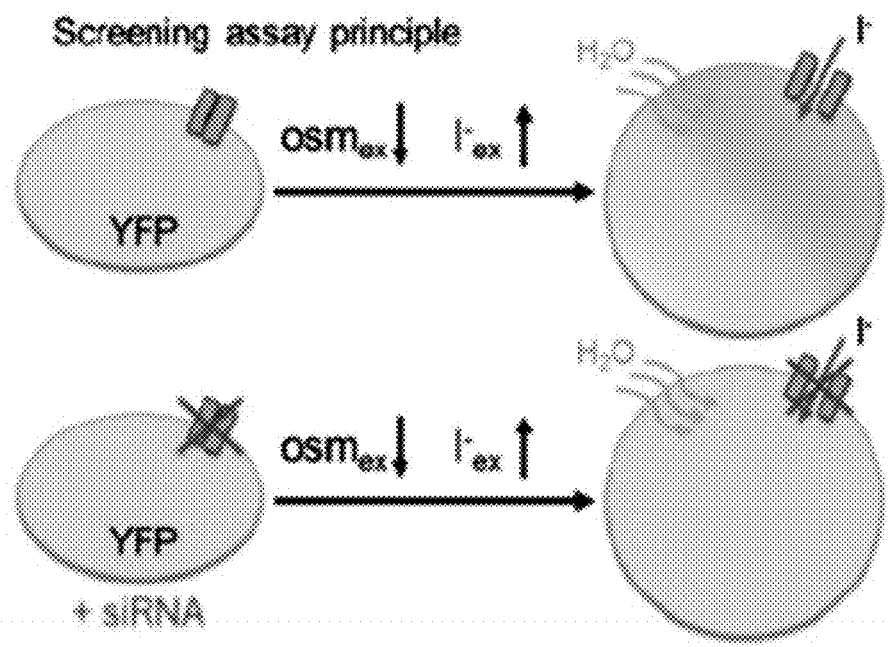
Figure 1:
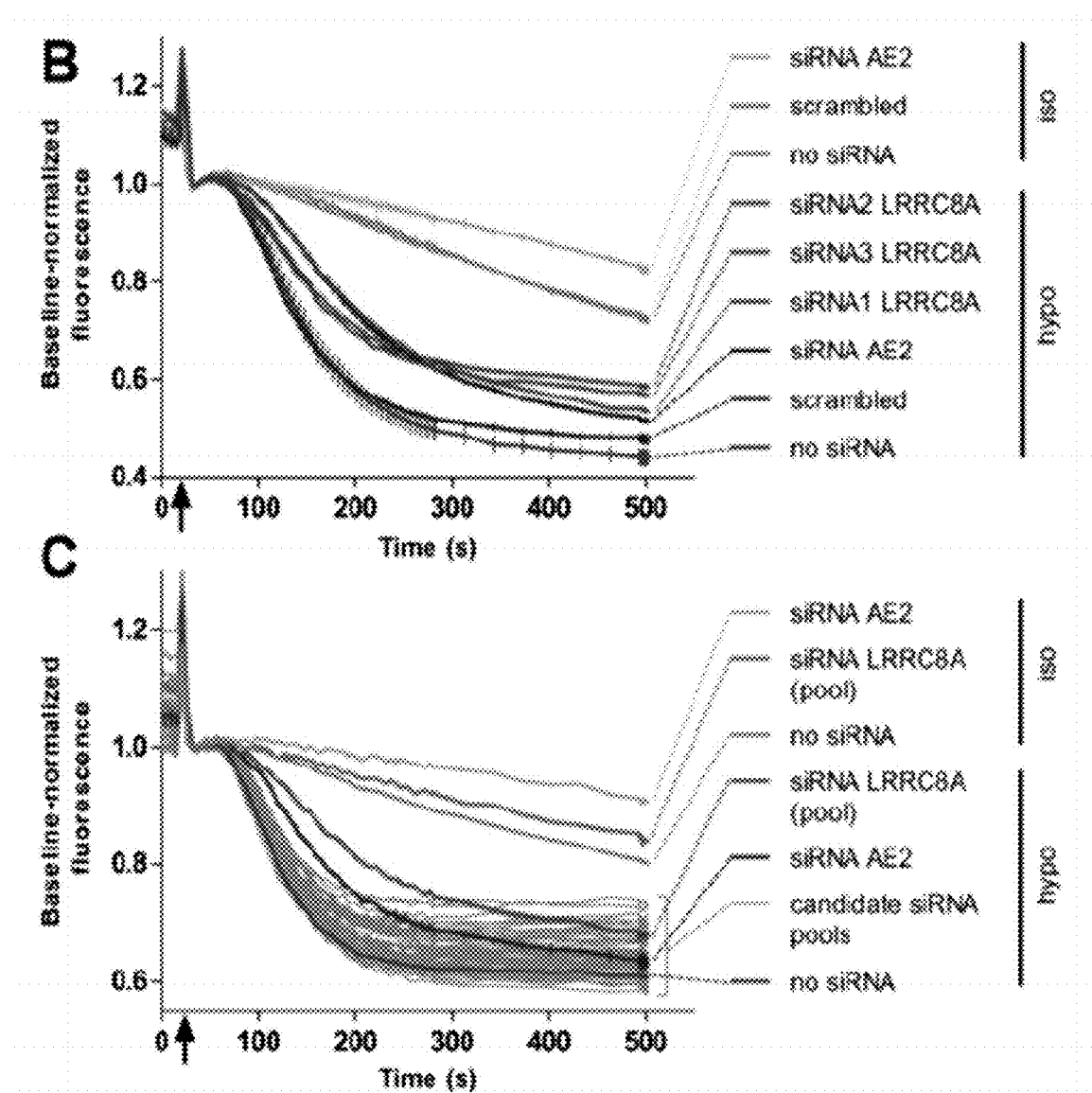
Figure 1:
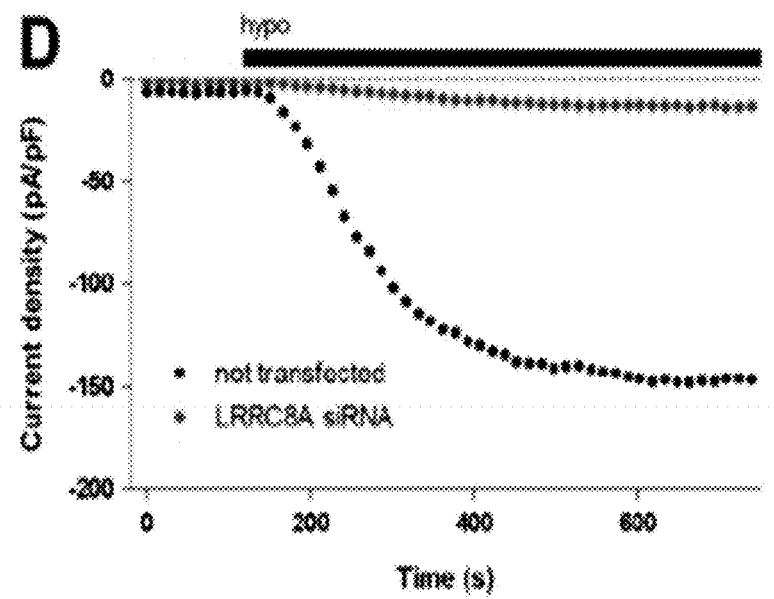
Figure 1:
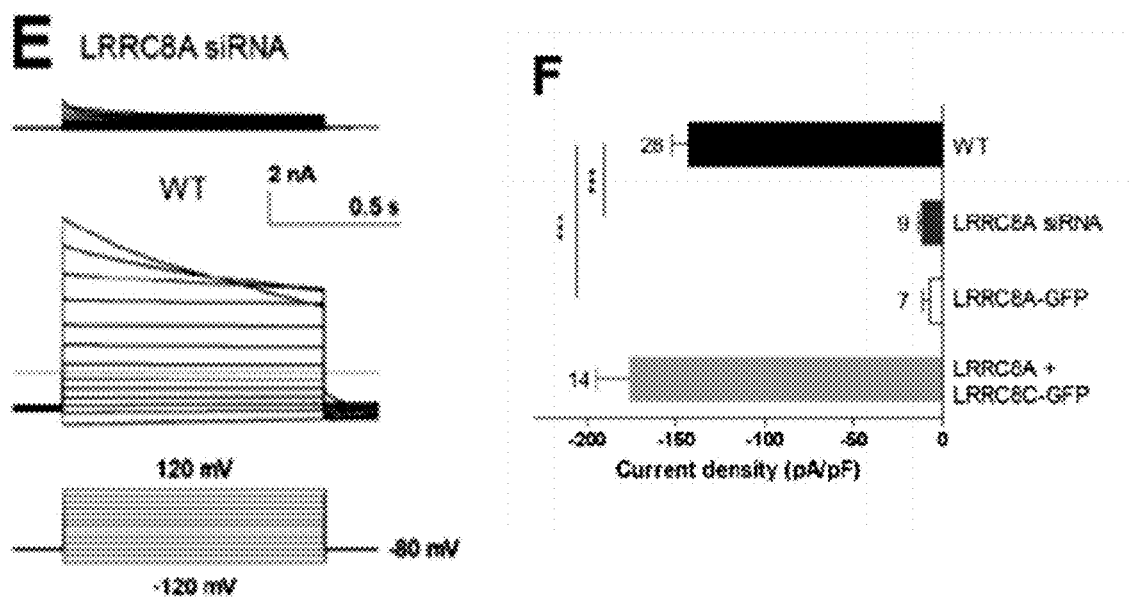

FIG. 1. siRNA screen for volume-regulated anion channel VRAC identifies LRRC8A.

Figure 2:
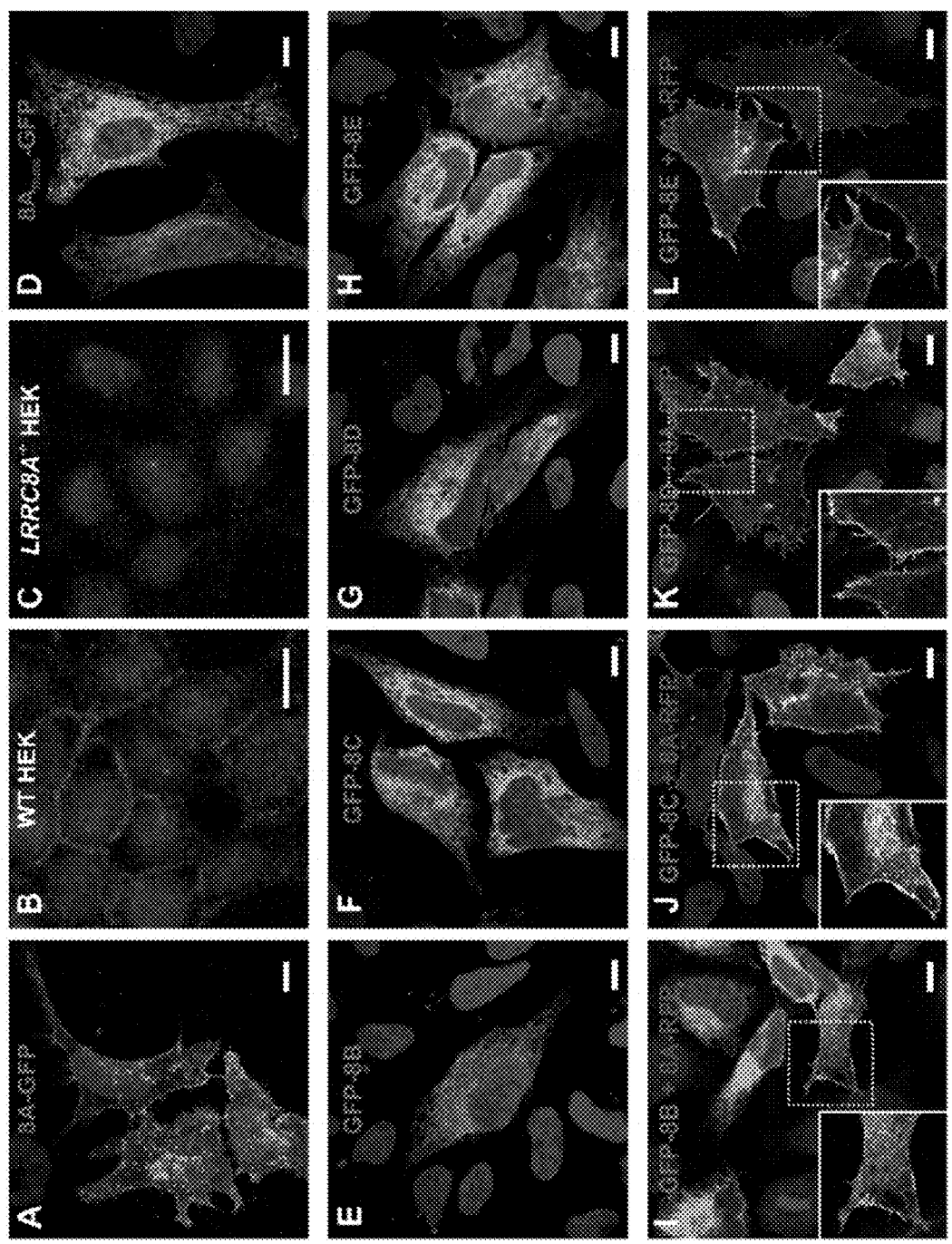

FIG. 2. Subcellular localization of LRRC8 proteins.

Figure 3:
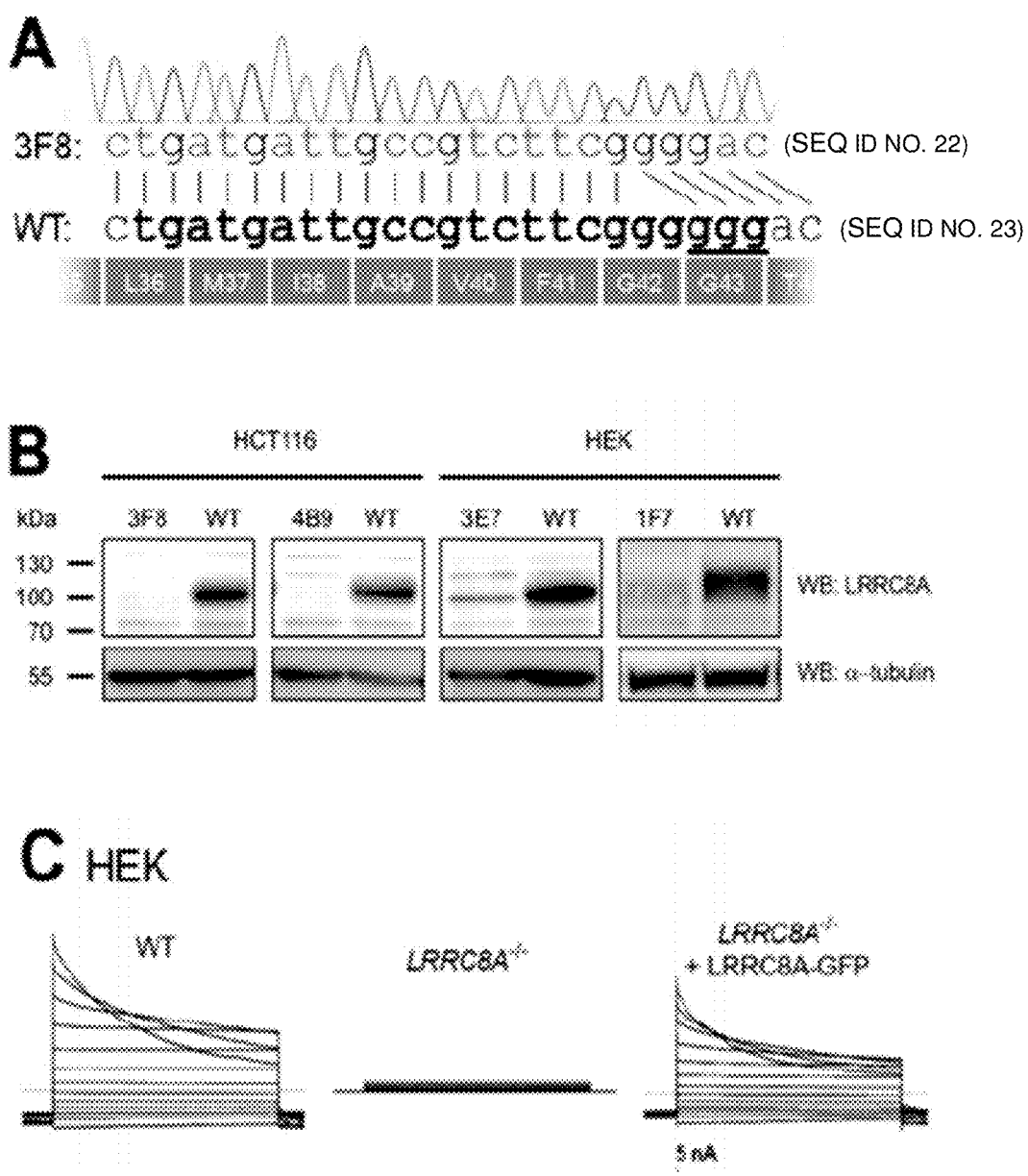
Figure 3:
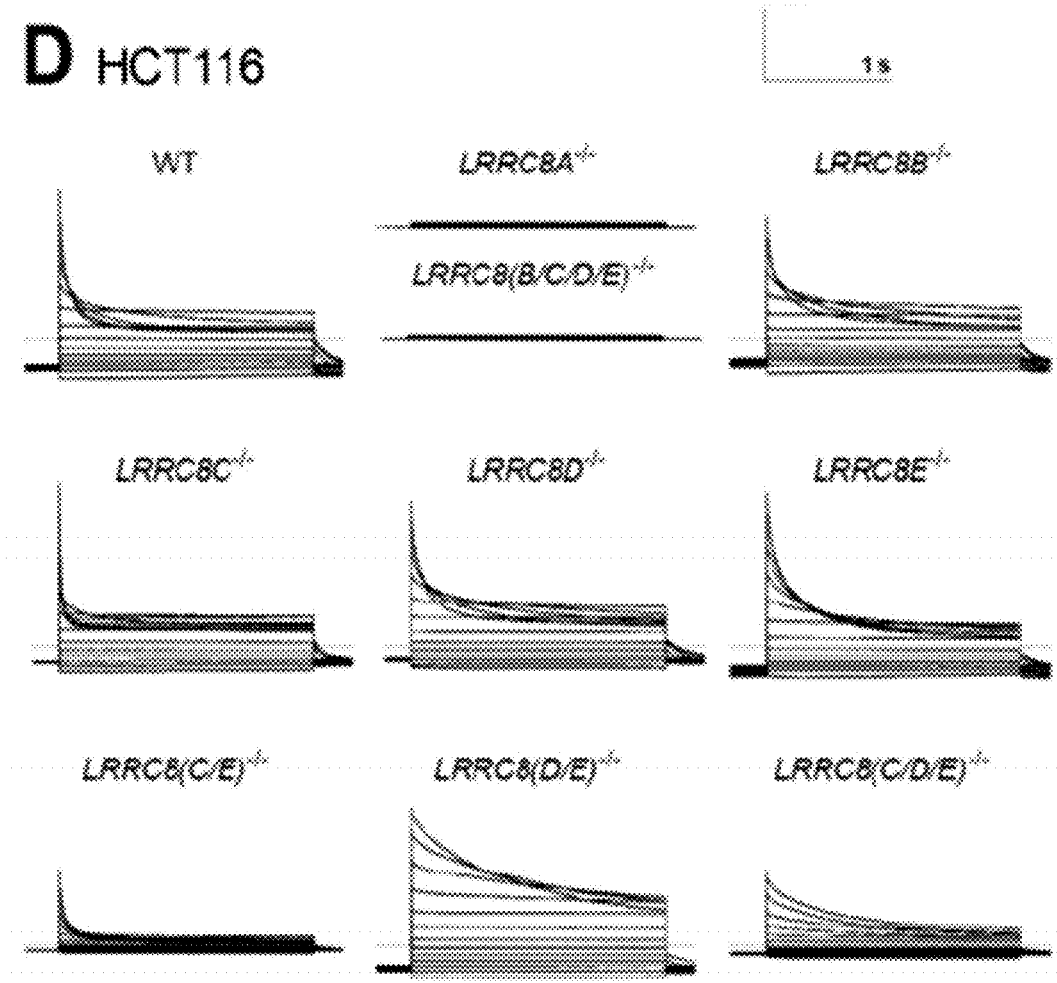
Figure 3:
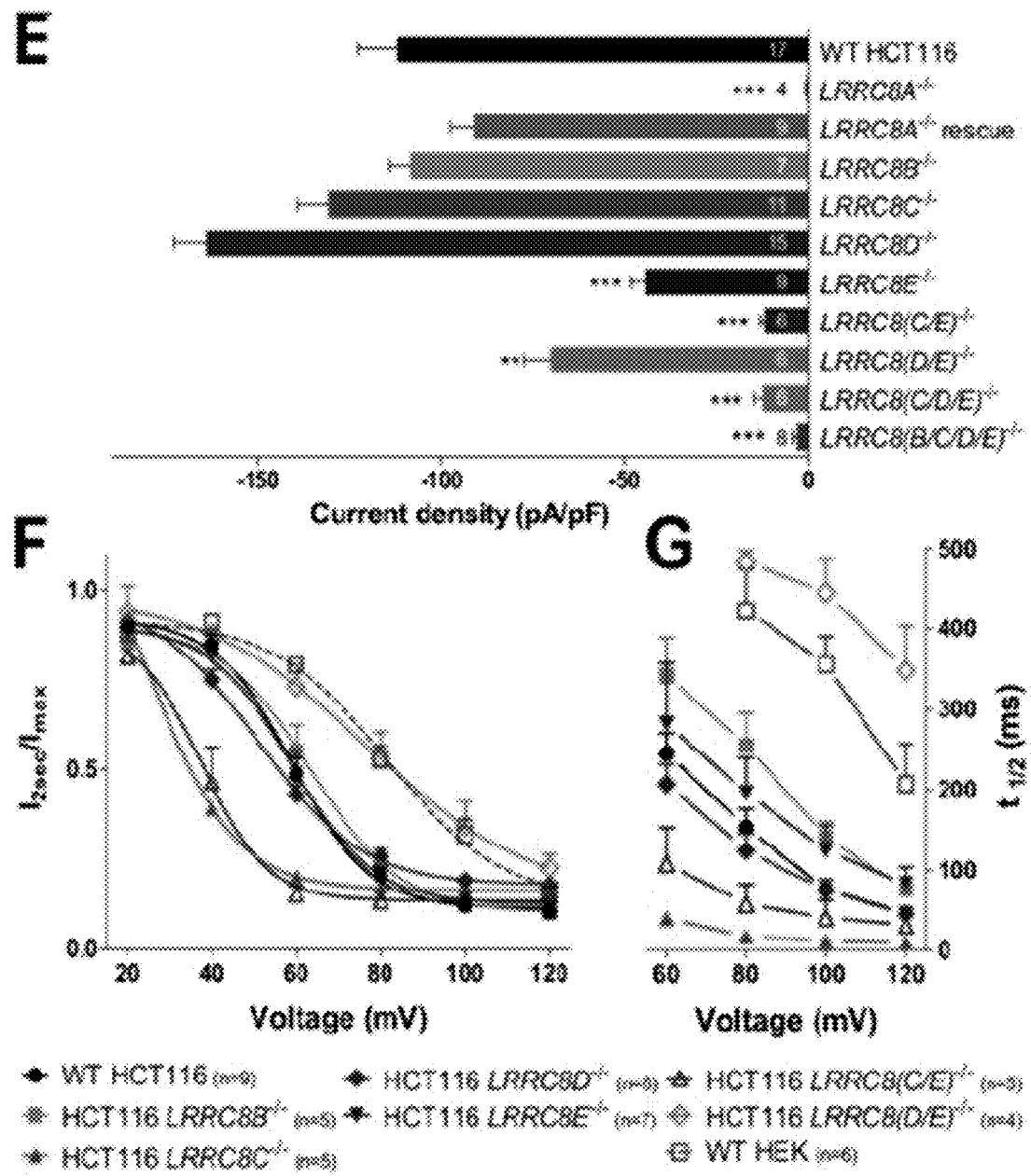

FIG. 3. Characterization of LRRC8 KO cell lines.

Figure 4:
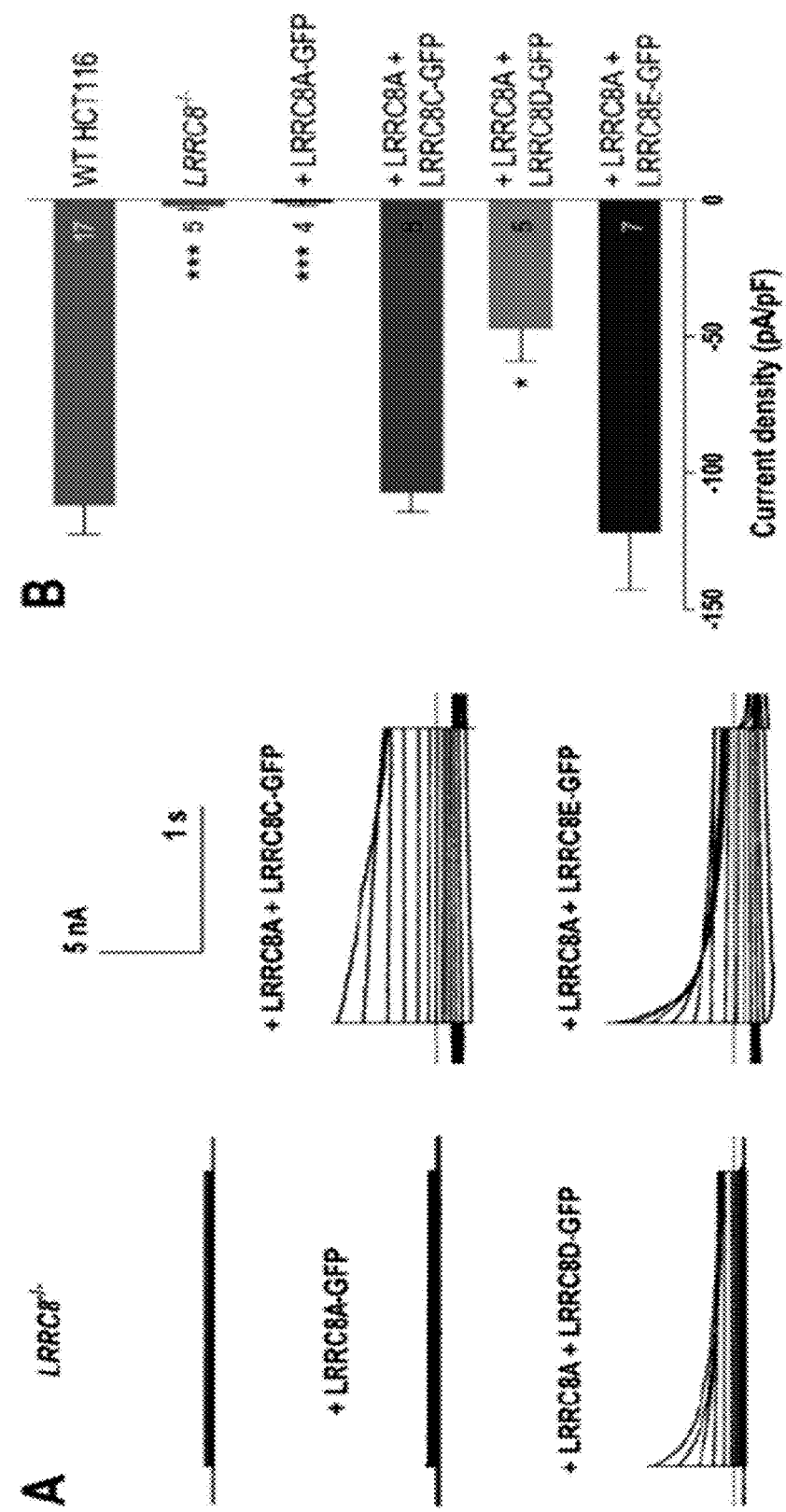
Figure 4:
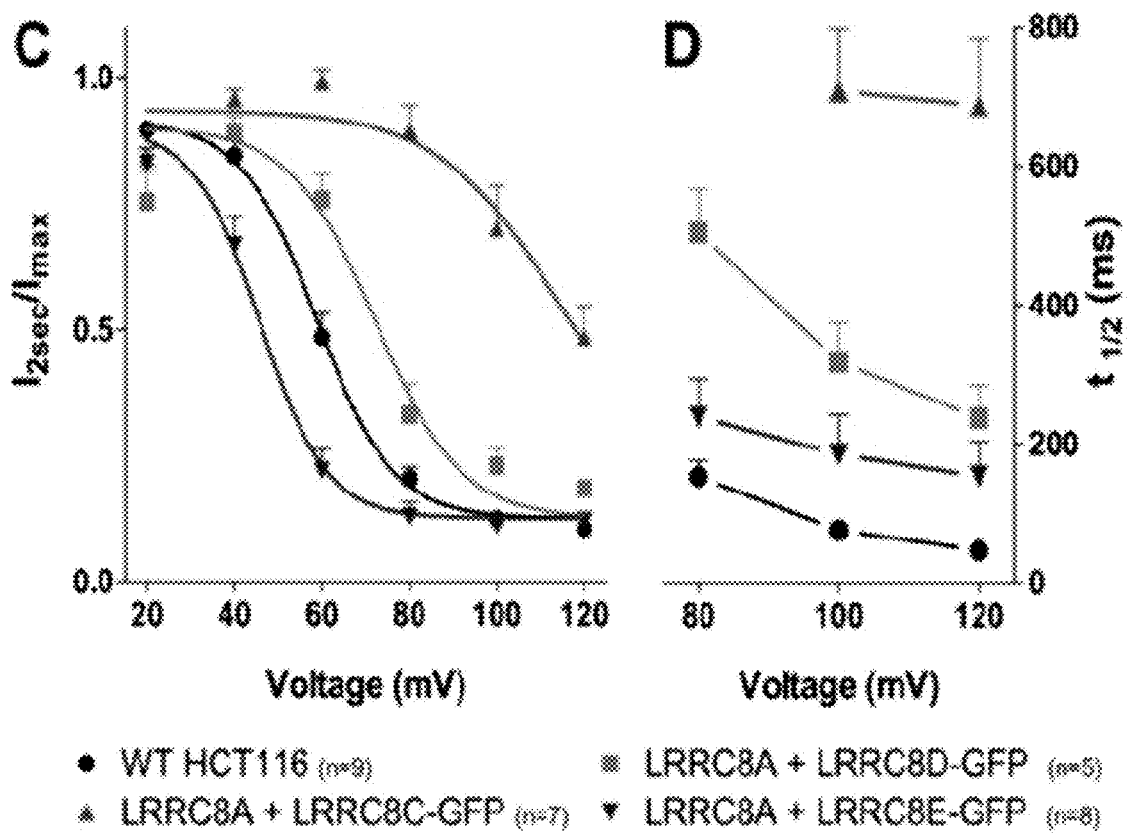
Figure 4:
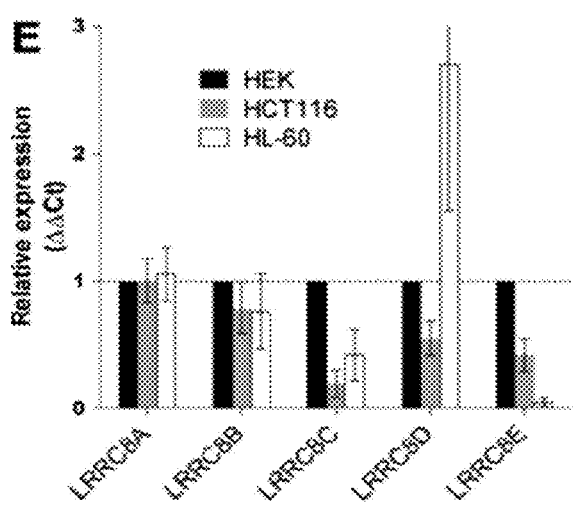

FIG. 4. Reconstitution of $I_{Cl(swell)}$ in the quintuple KO cell line LRRC8⁻/⁻.

Figure 5:
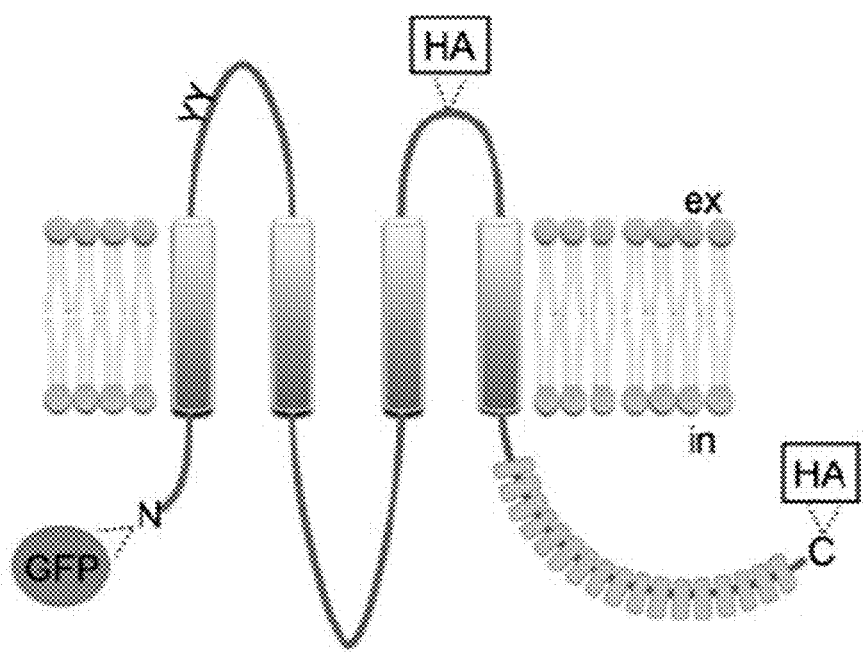
Figure 5:
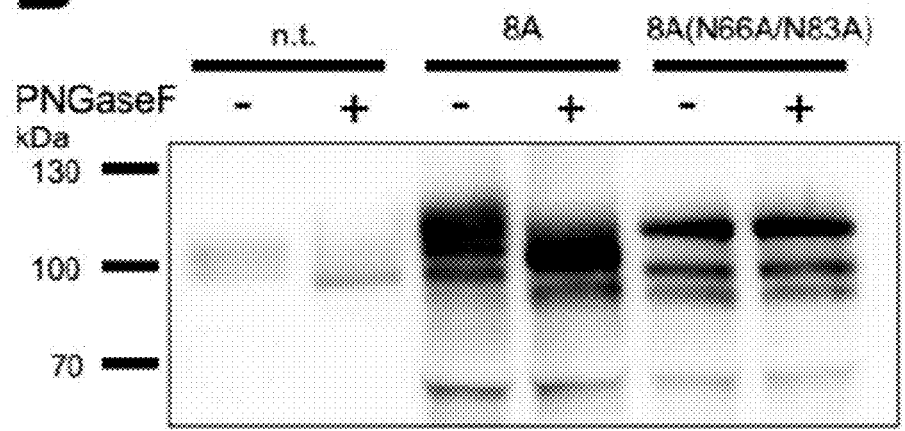
Figure 5:
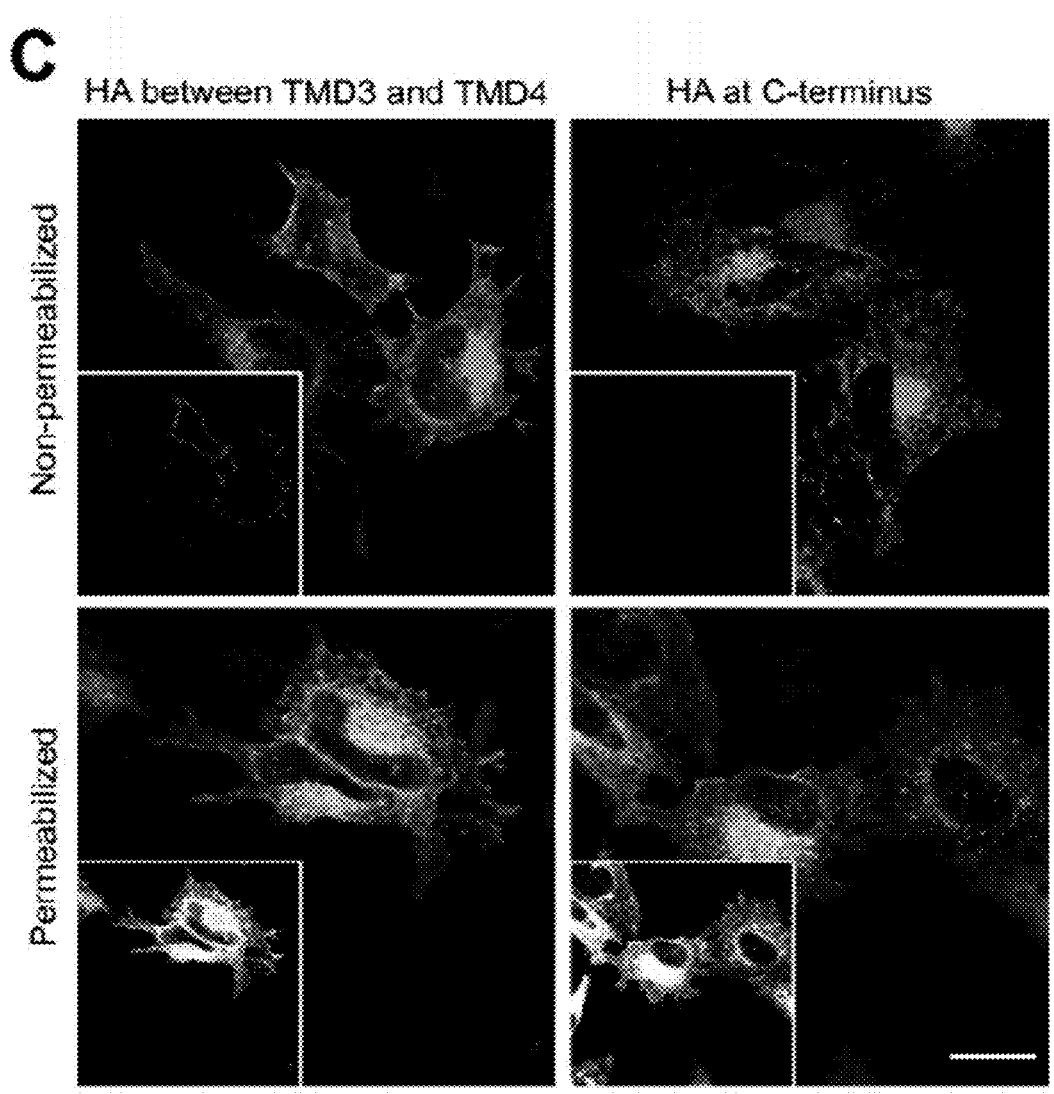
Figure 5:
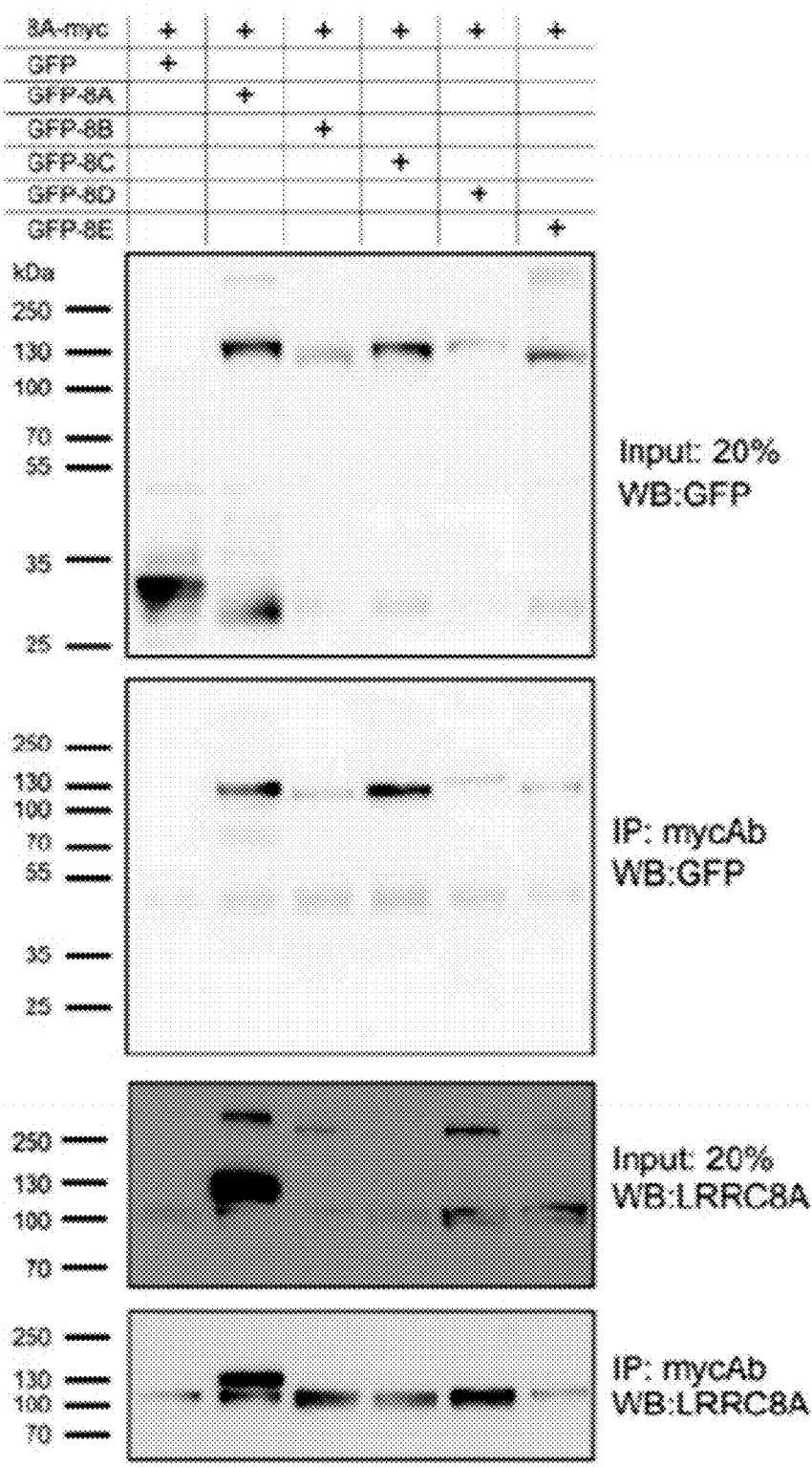
Figure 5:
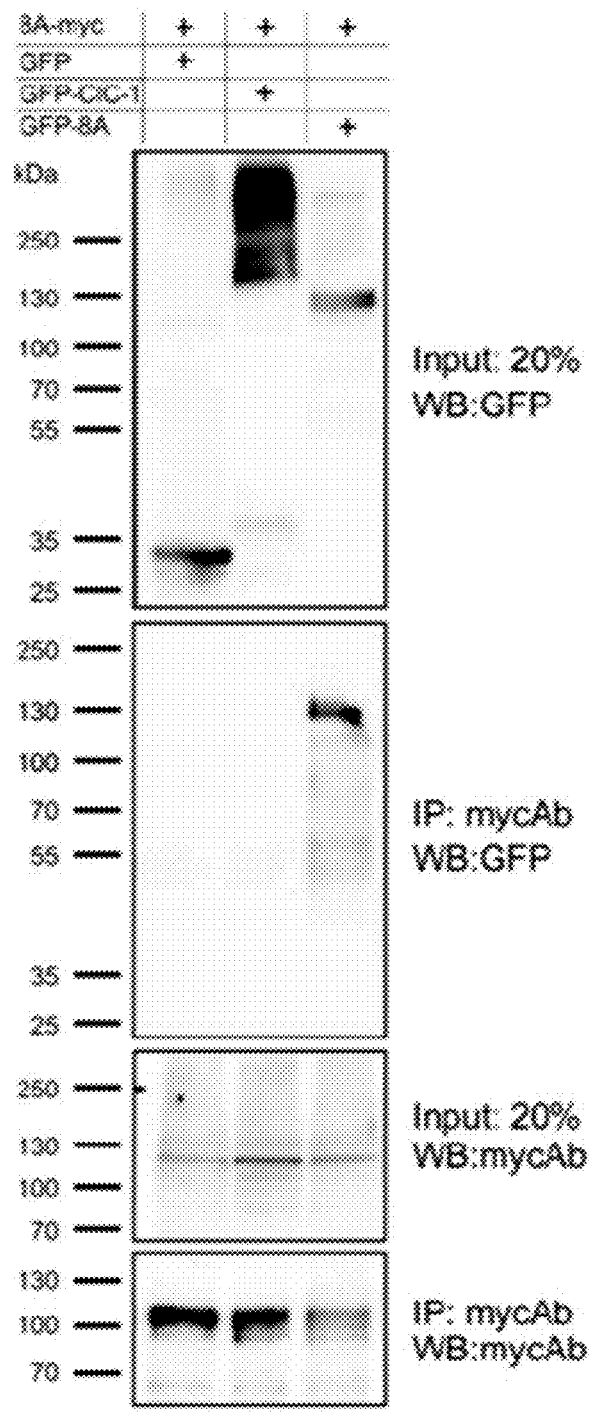
Figure 5:
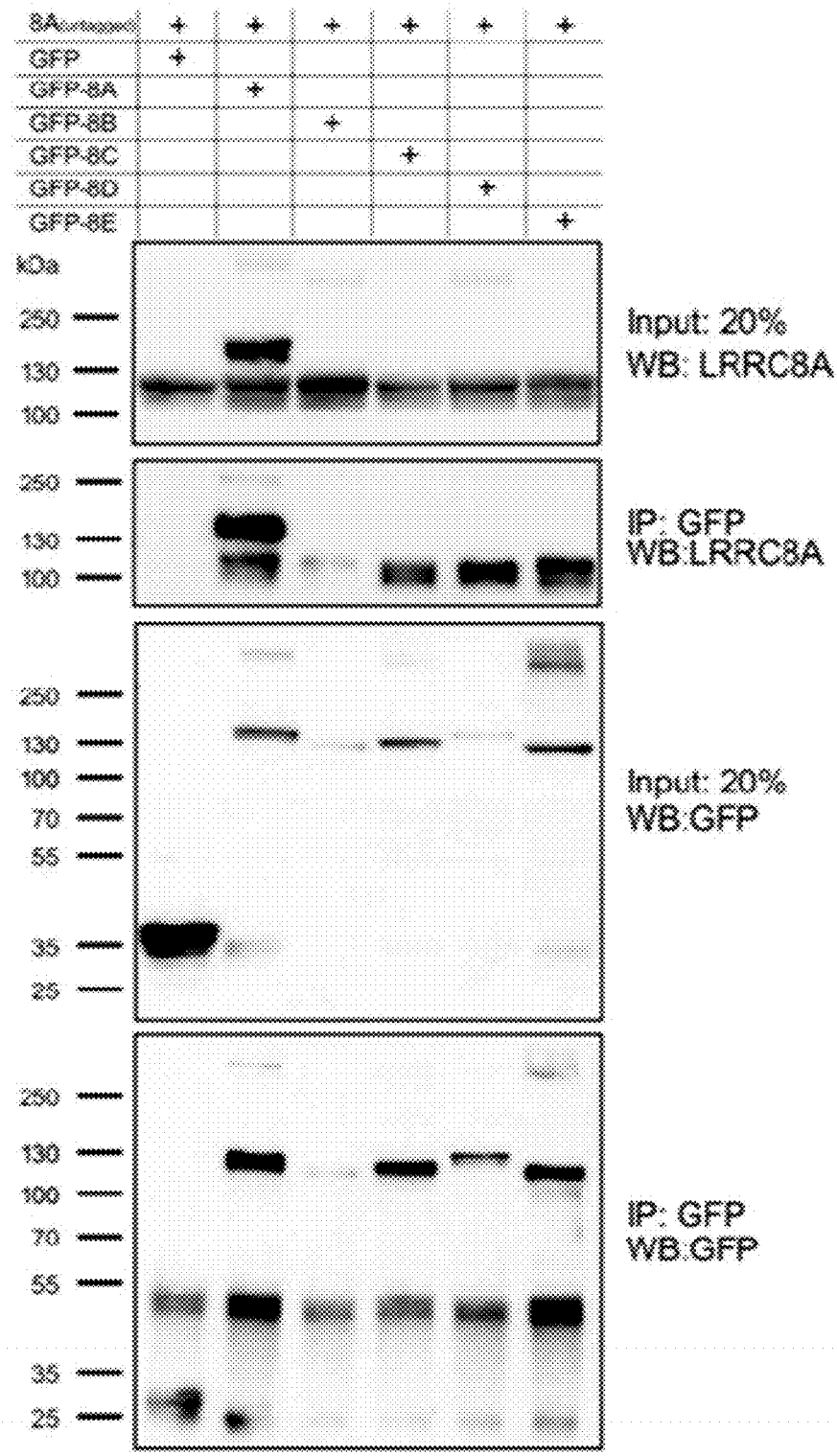
Figure 5:
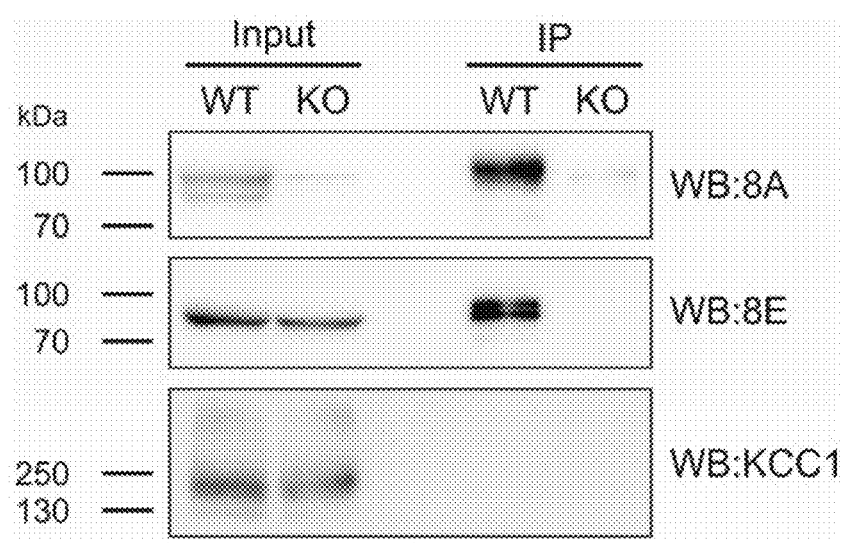

FIG. 5. Transmembrane topology and heteromerization of LRRC8A.

Figure 6:
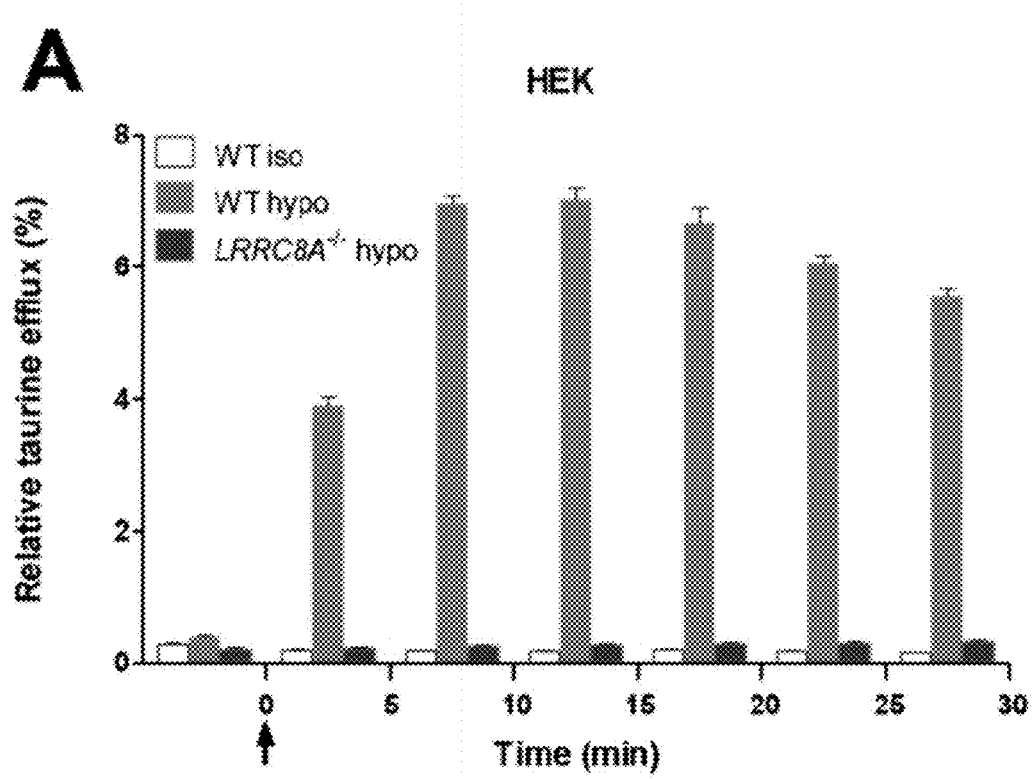
Figure 6:
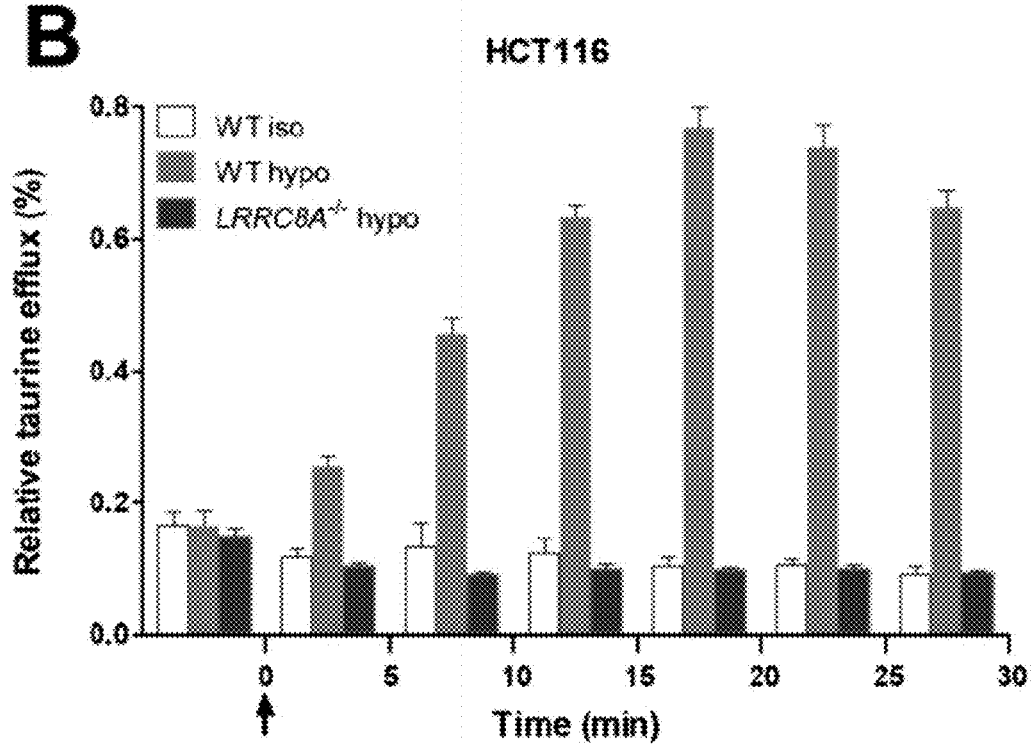
Figure 6:
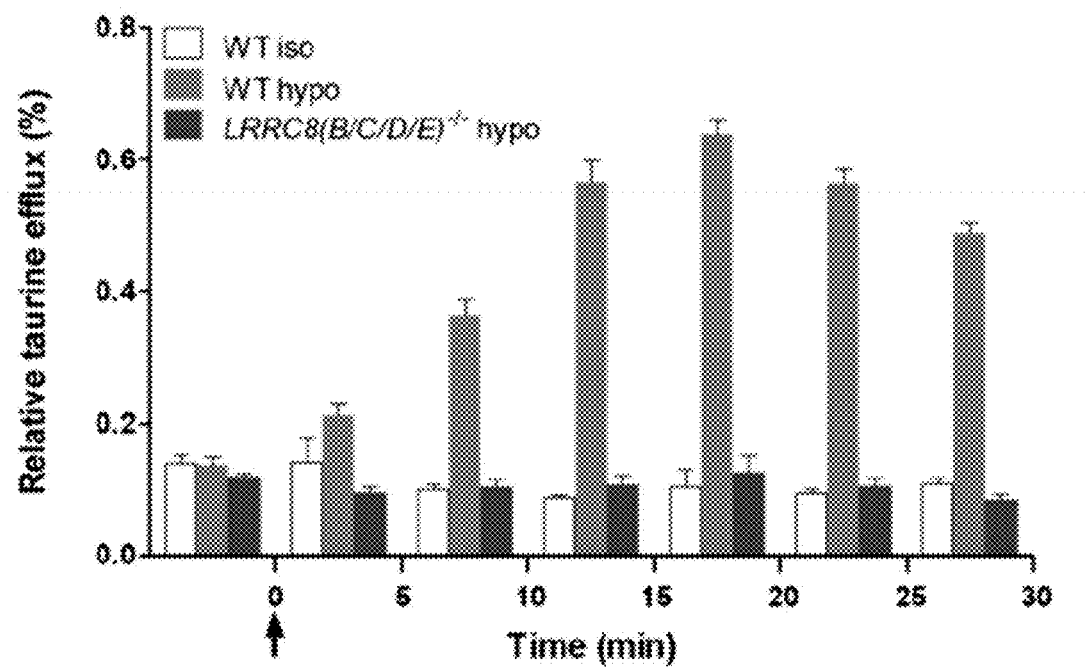
Figure 6:
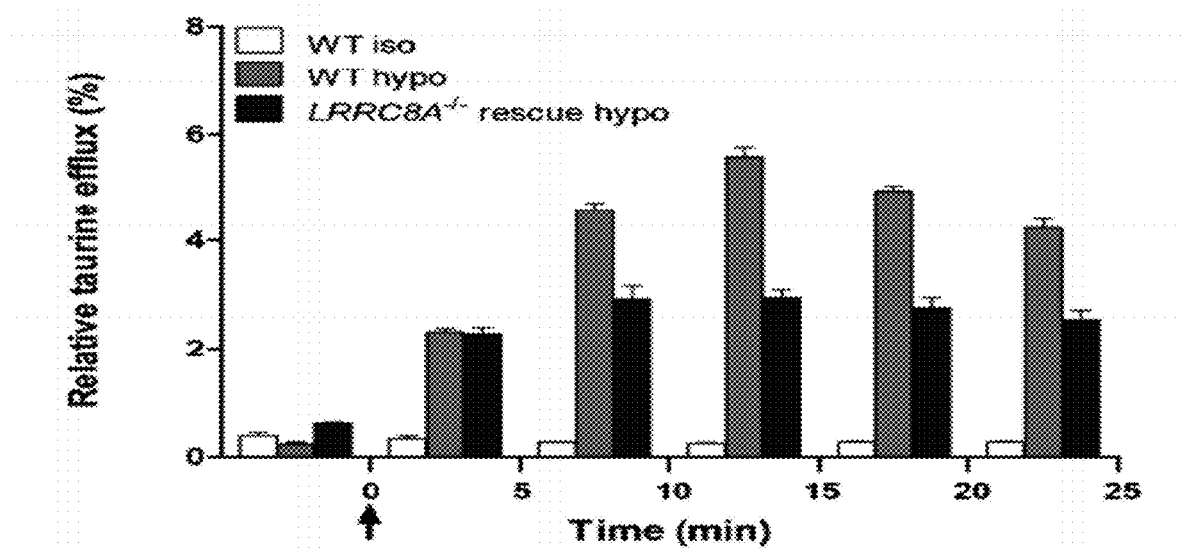

FIG. 6. LRRC8 proteins are indispensable for swelling-induced efflux of taurine.

Figure 7:
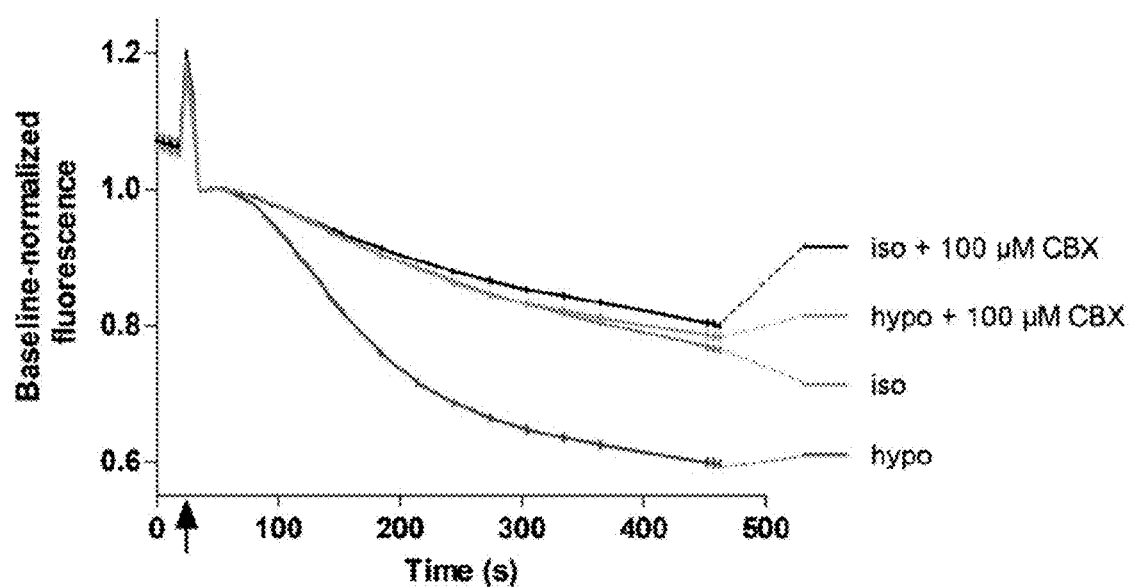

FIG. 7. Effect of carbenoxolone on hypotonicity-induced YFP quenching by iodide.

Figure 8:
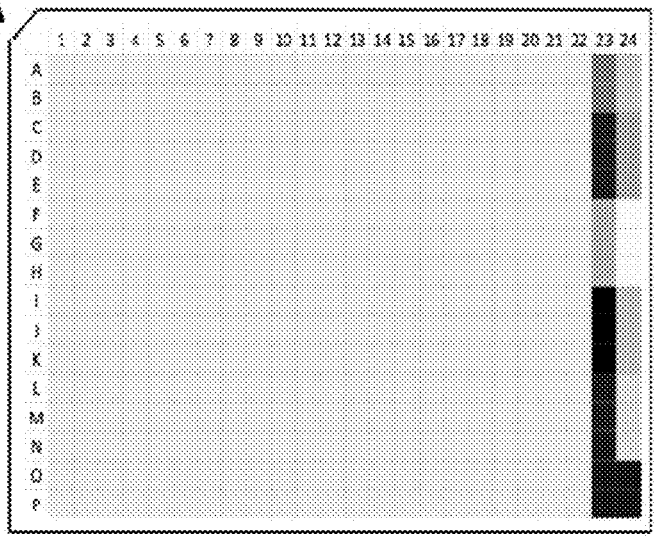
Figure 8:
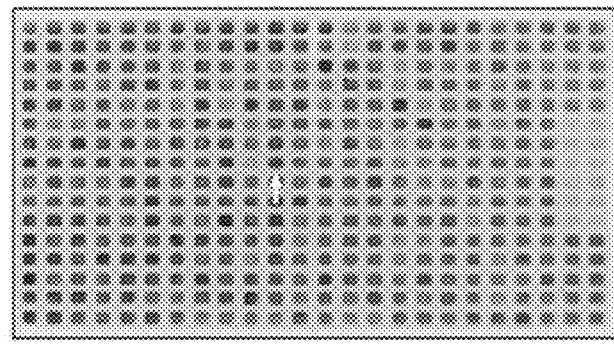
Figure 8:
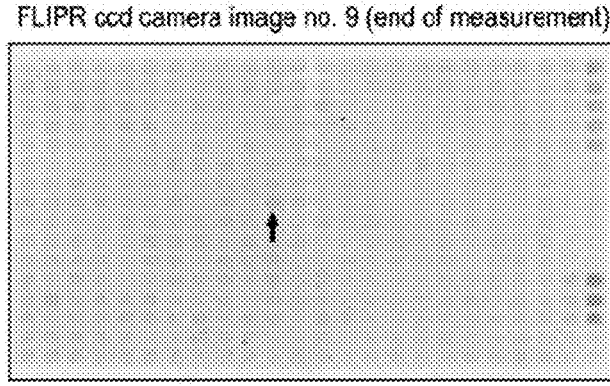
Figure 8:
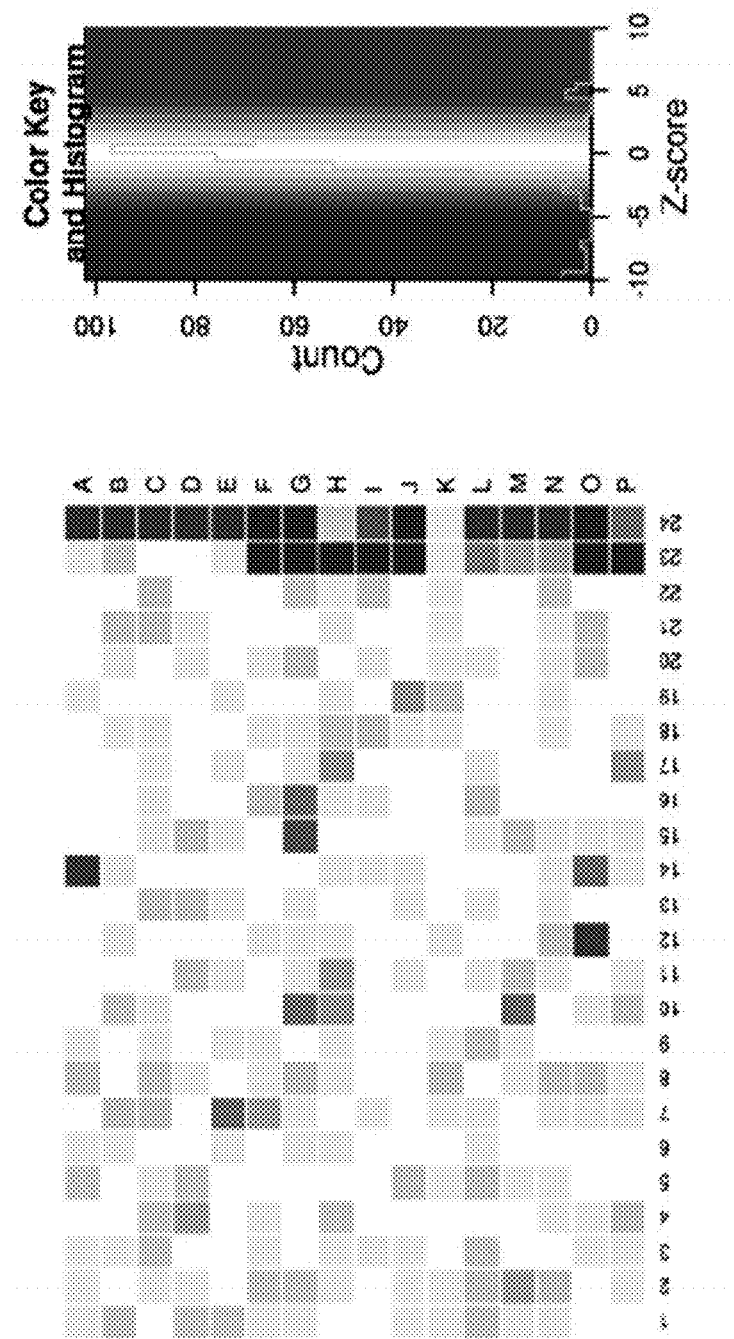

FIG. 8. Genome-wide RNA interference screen for VRAC.

Figure 9:
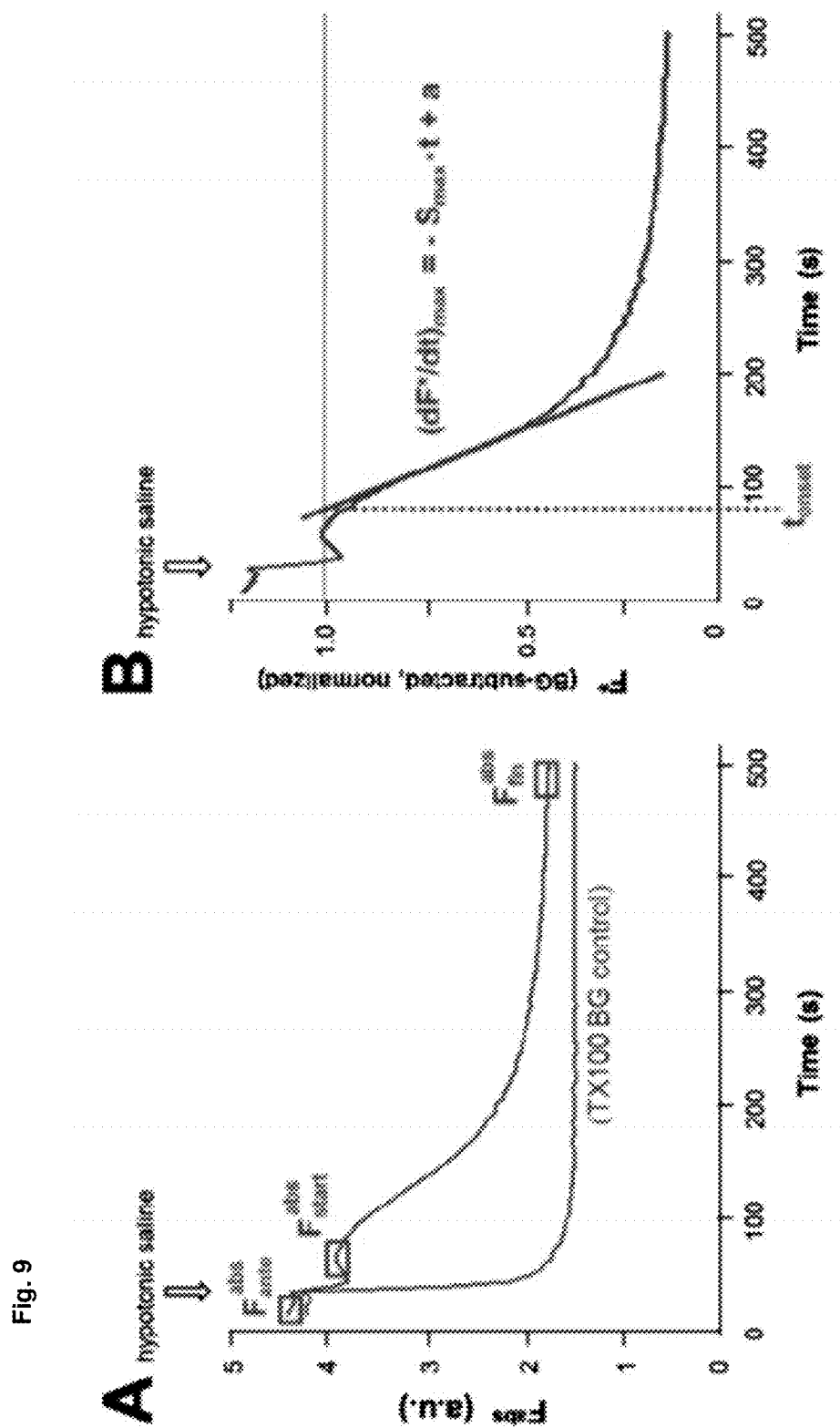
Figure 9:
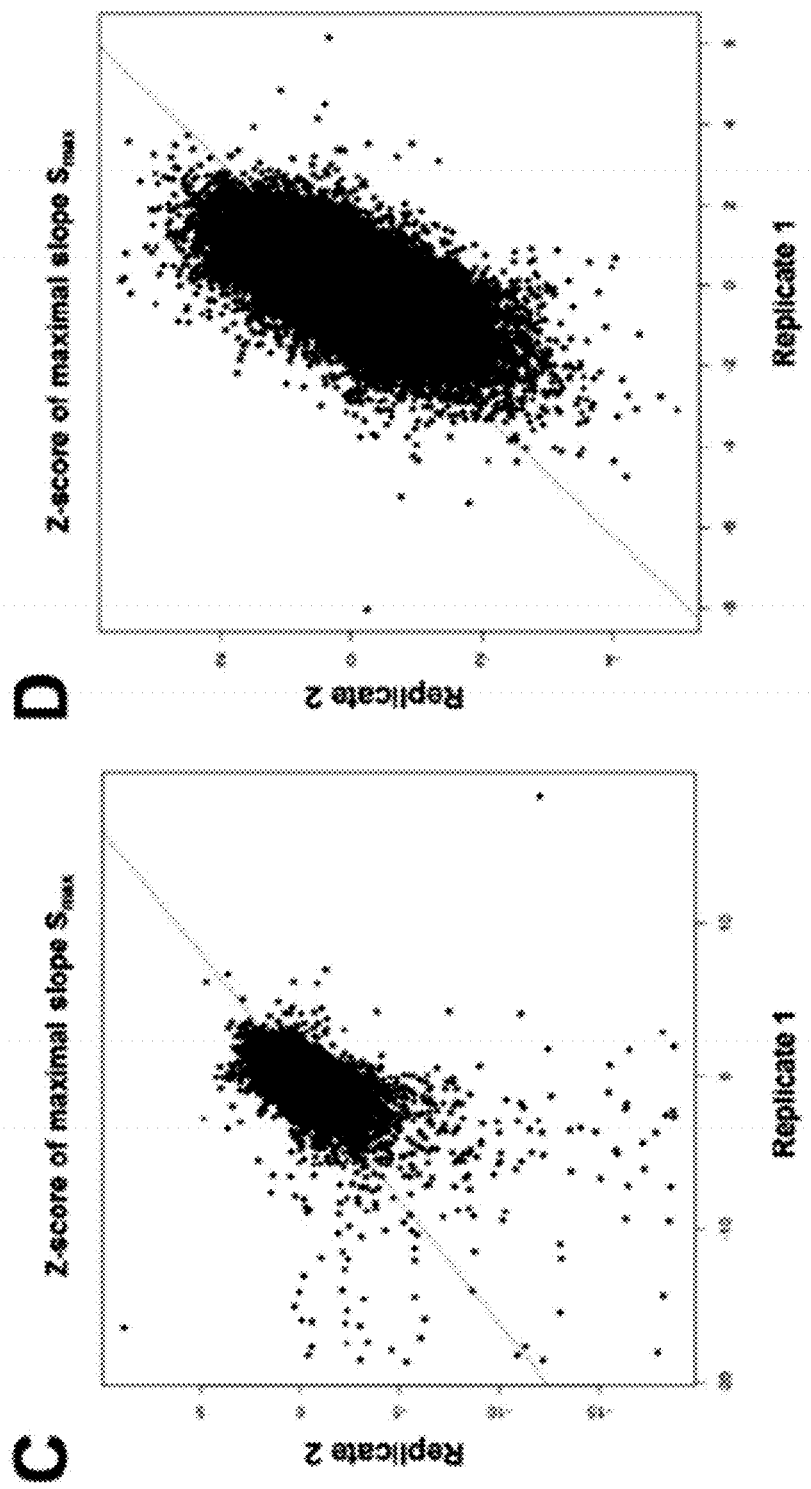
Figure 9:
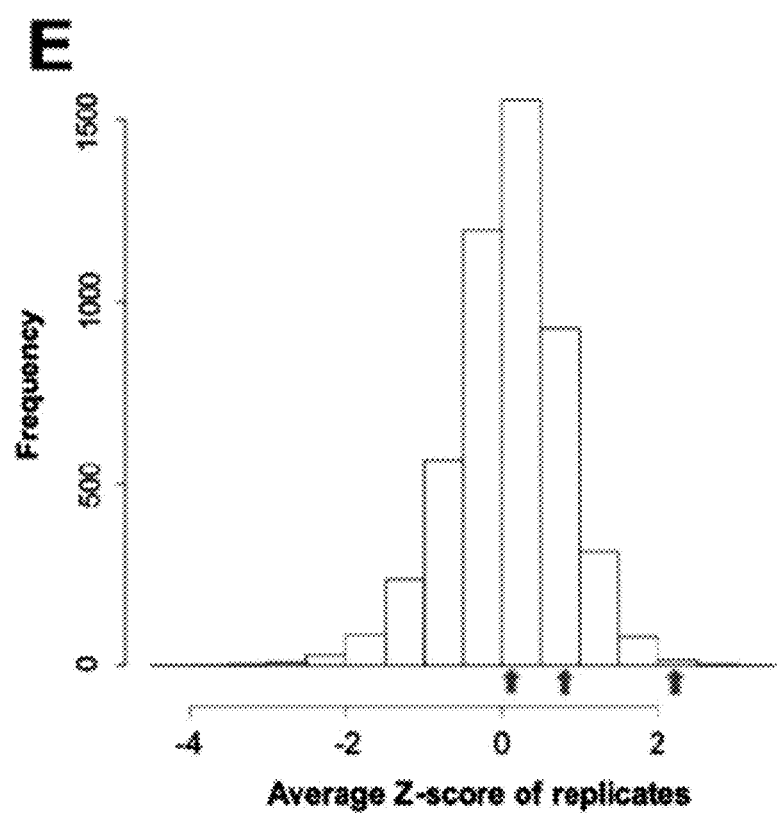

FIG. 9. Analysis of the primary, genome-wide siRNA screen for VRAC.

Figure 10:
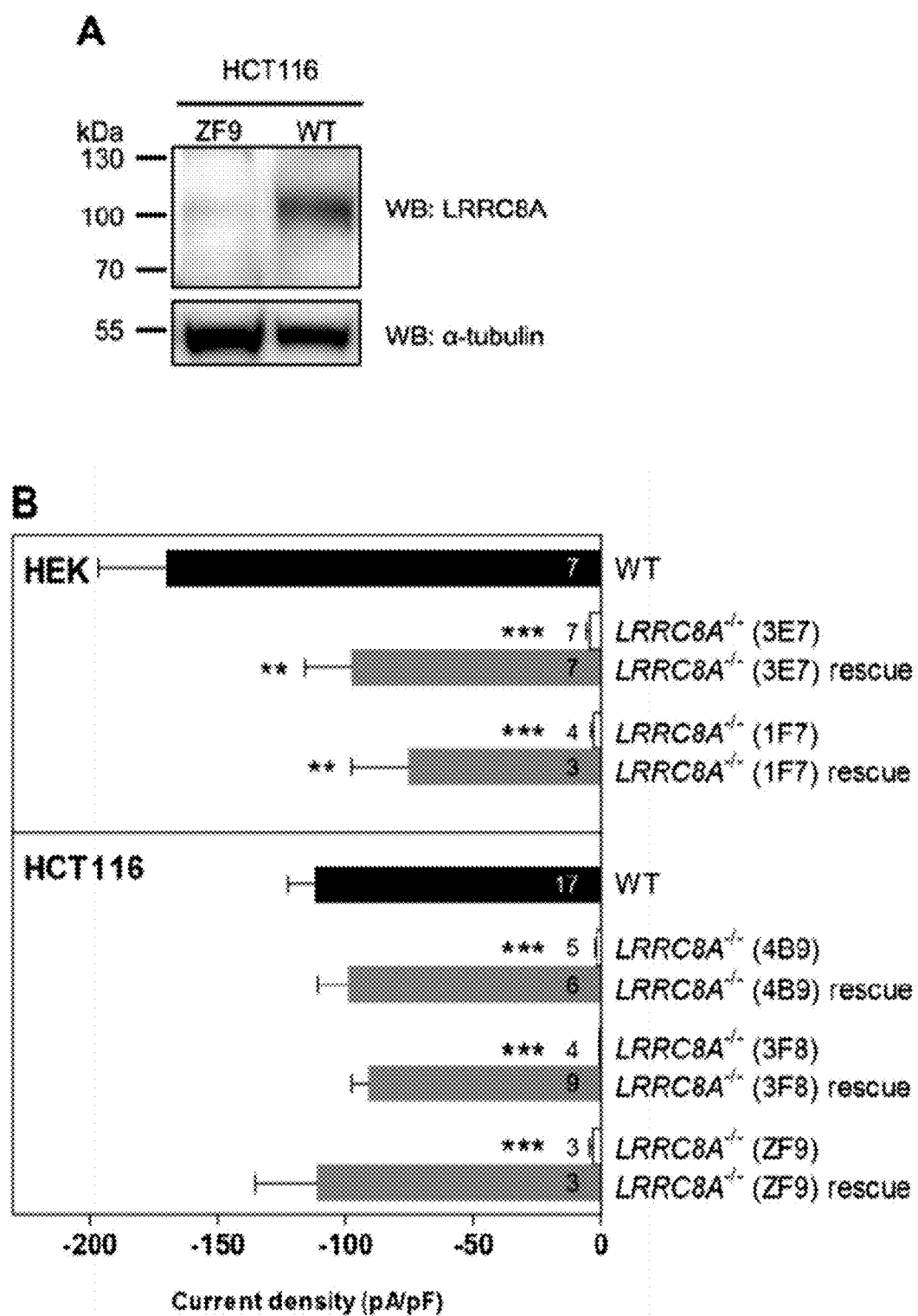

FIG. 10. Absence of $_{ICl(swell)}$ in independent LRRC8A$^{-/-}$ cell lines.

Figure 11:
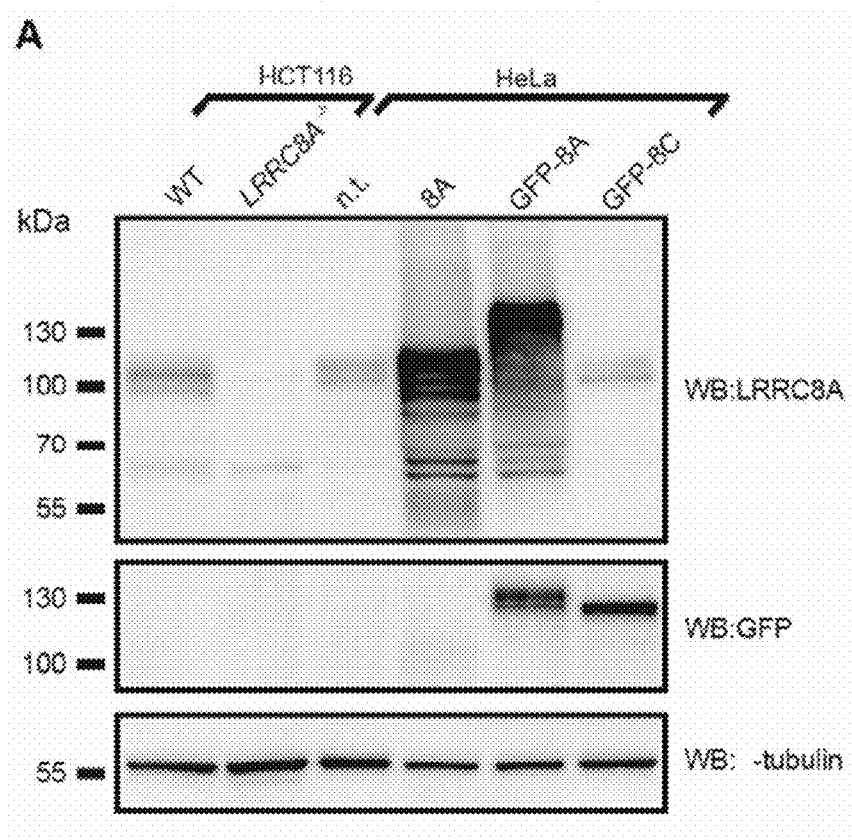
Figure 11:
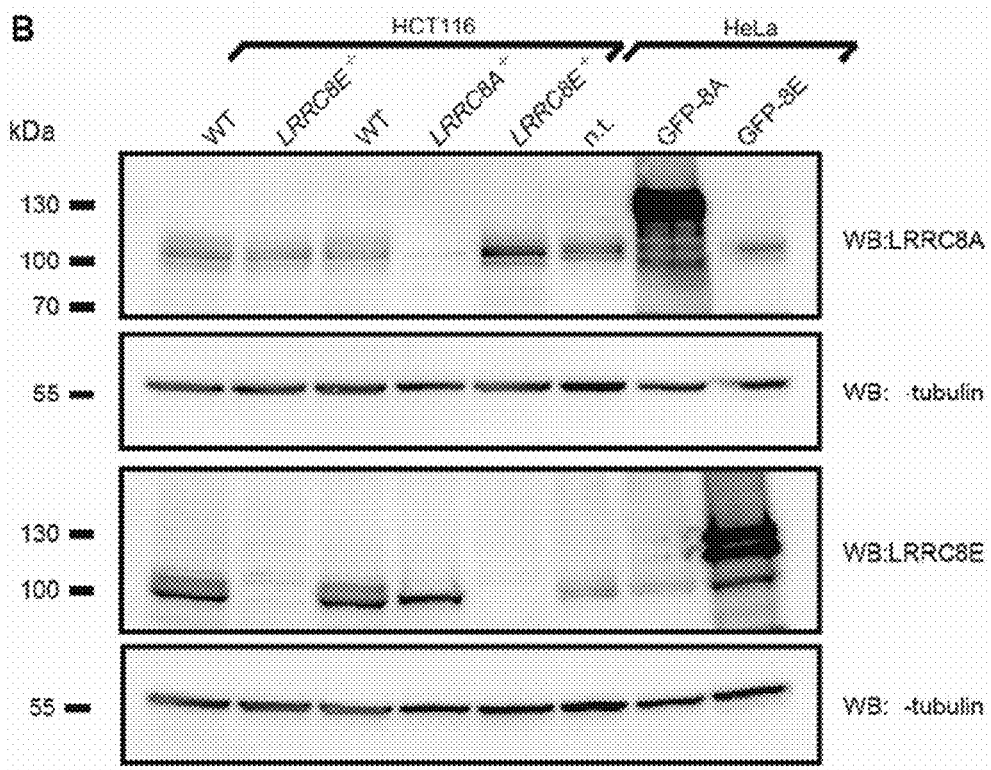
Figure 11:
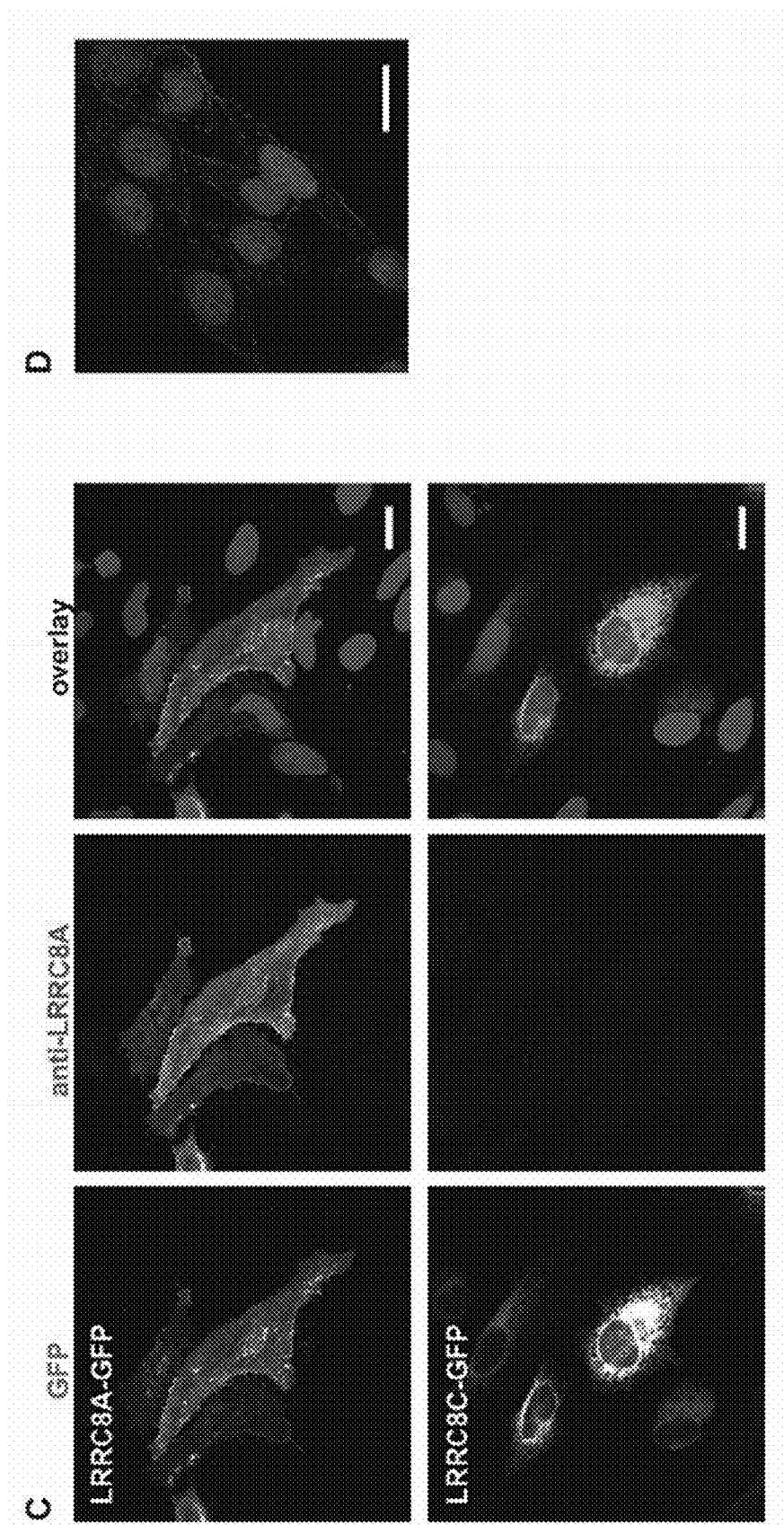

FIG. 11. Characterization of the LRRG8A and LRRG8E antibodies.

Figure 12:
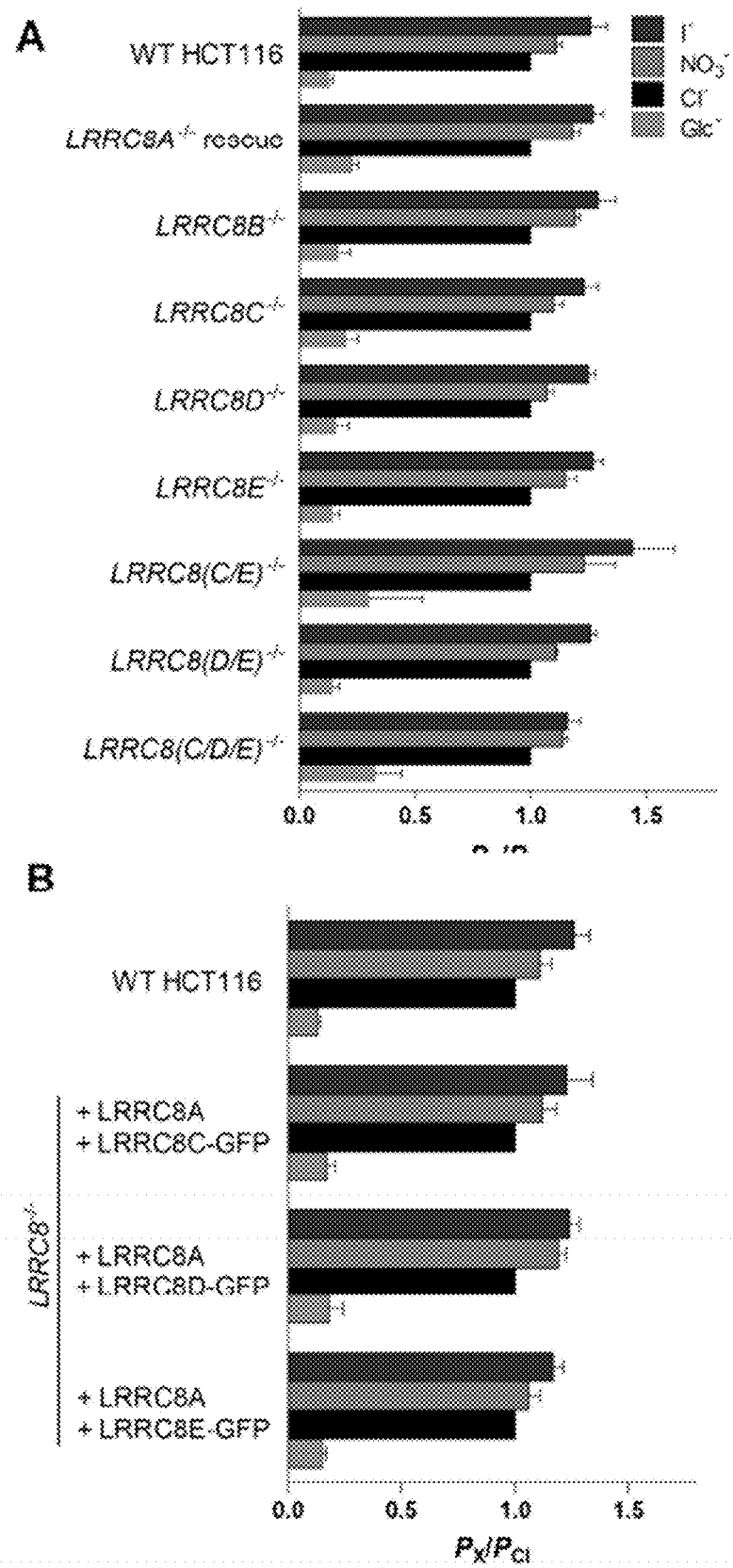
Figure 12:
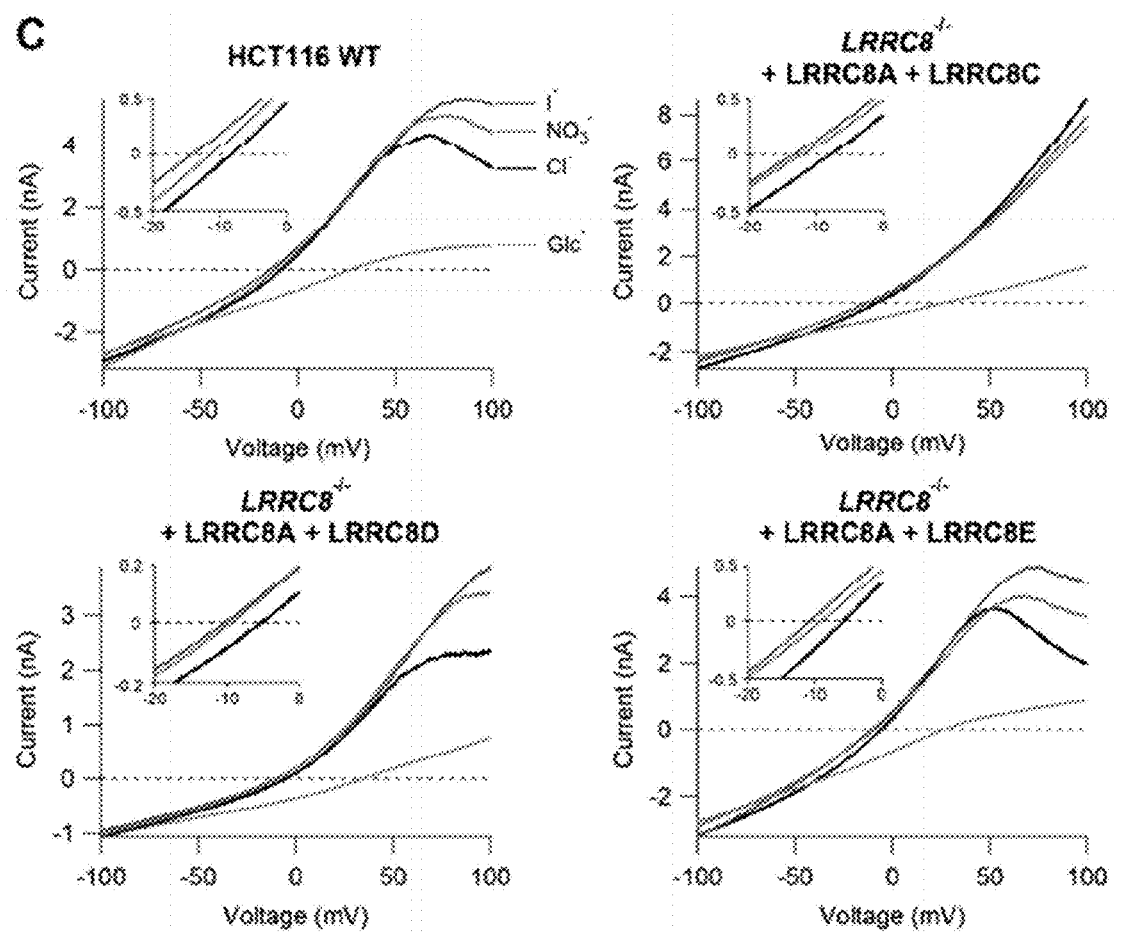
Figure 12:
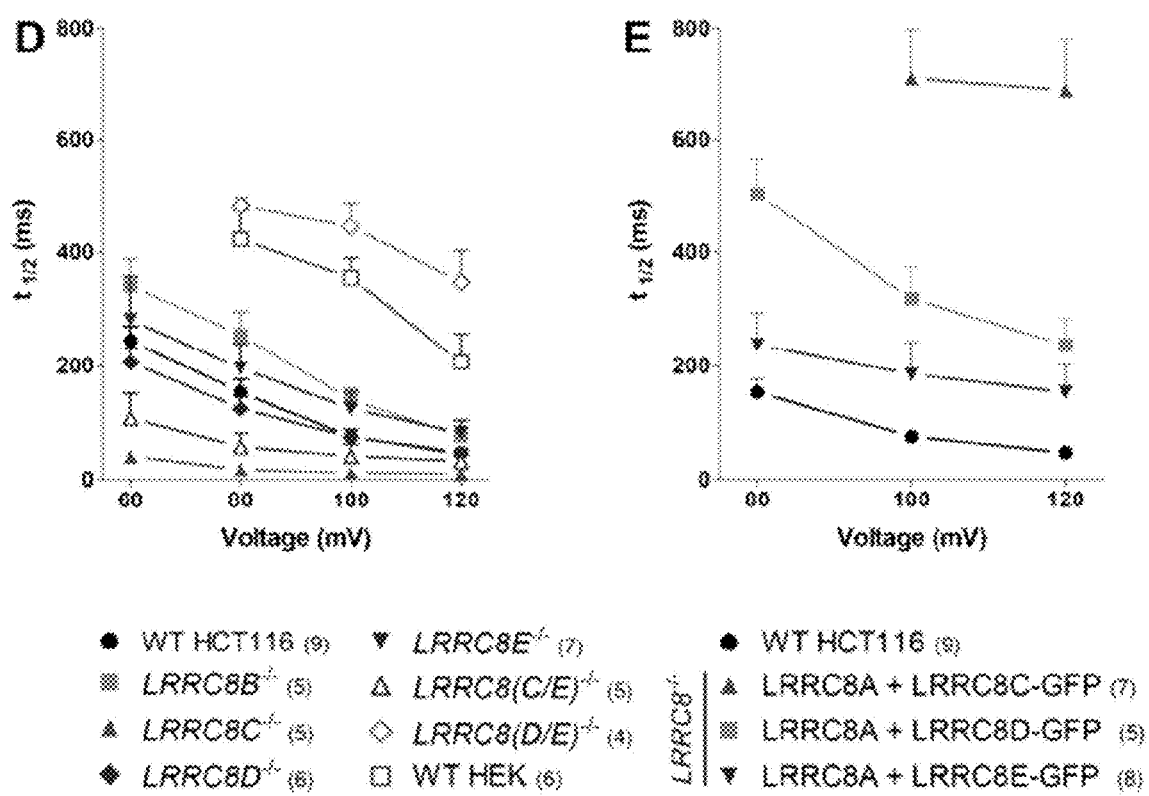

FIG. 12. Characterization of ICl(swell) in HCT116 cells.

Figure 13:
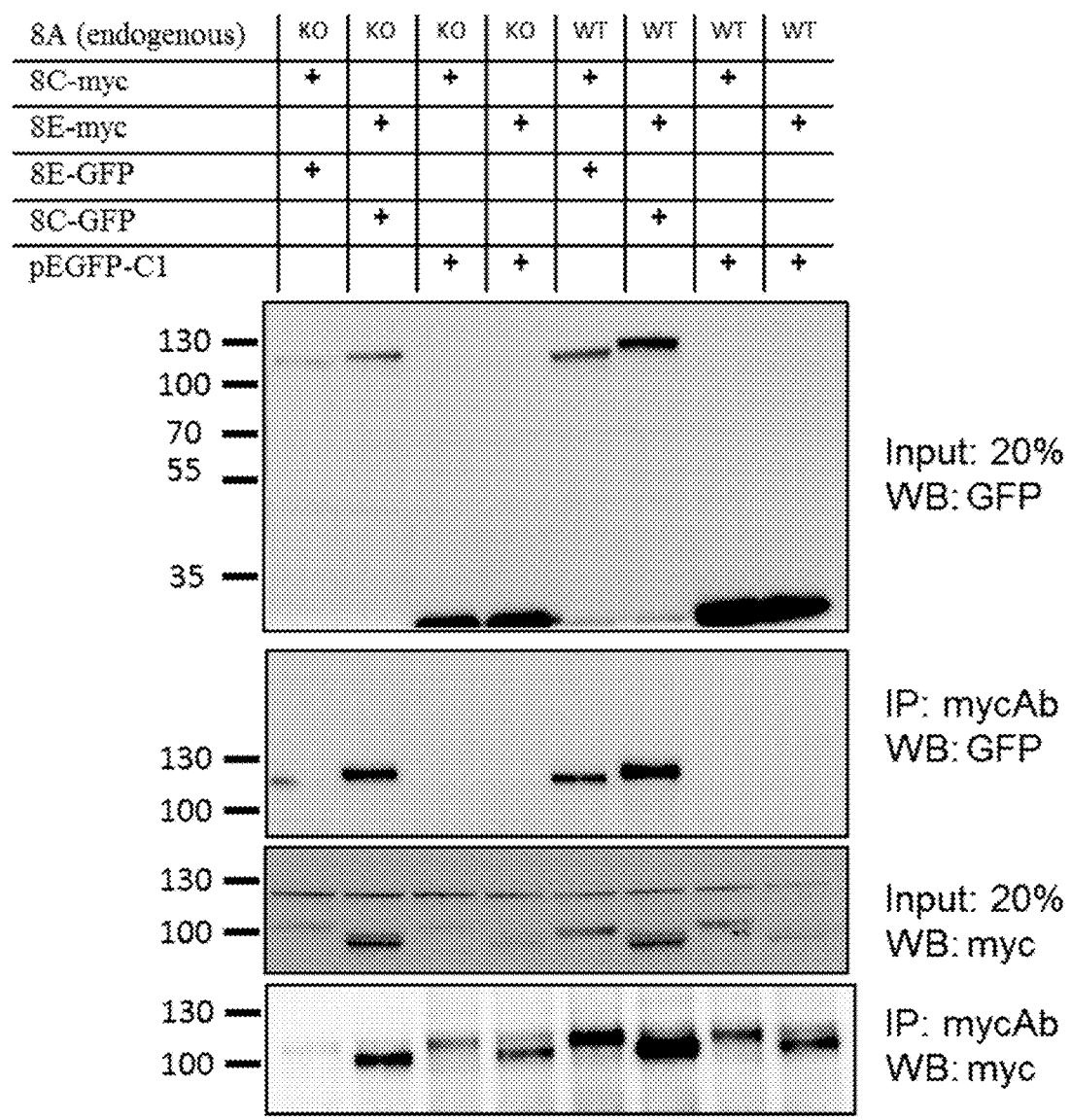

FIG. 13. Heteromerization of LRRC8 proteins in absence of LRRG8A.

SUMMARY OF THE INVENTION

There is a need in the art to provide for the identification and/or characterisation of channel modulators and/or volume regulated channel function.

This need and other needs are addressed by the features of the independent claims. Preferred embodiments of the present invention are provided by the dependent claims.

The invention therefore relates to a method for the identification of a channel modulator, such as a channel agonist (activator) or antagonist (inhibitor), comprising Providing one or more candidate substances;
Providing one or more LRRC8 proteins selected from LRRG8A, LRRG8B, LRRC8C, LRRG8D and LRRG8E, or a protein complex comprising one or more of LRRG8A, LRRG8B, LRRC8C, LRRG8D and/or LRRG8E;
Contacting said candidate substance(s) with said protein and/or protein complex; and
Determining the presence or absence of an interaction between said candidate substance(s) and said protein complex.

In one embodiment the method of the present invention is characterized in that the channel is a volume regulated anion channel (VRAC), for volume stimulated outward rectifier (VSOR), or volume-stimulated organic osmolyte/anion channel (VSOAC).

As discussed herein, until the present time the components of the volume regulated anion channel (VRAC) were unknown. The invention therefore provides the novel development of the art via the provision of LRRC8 proteins or complexes thereof as a structural component of VRAC. The provision of LRRC8 proteins A to E enables methods as described herein for identifying modulators of the channel for potential use as medically relevant compounds or as research tools for in vitro modulation of cell volume. LRRC8 proteins have not previously been proposed as a structural factor in VRAC. Methods for interrogating VRAC function based on LRRC8 proteins are novel and not suggested in the art.

In one embodiment the method of the invention is characterised in that a protein complex is provided, and wherein said complex is a heteromer and comprises more than one of LRRC8A, LRRC8B, LRRC8C, LRRC8D and/or LRRC8E.

In one embodiment the method of the invention is characterised in that a protein complex is provided, and wherein said complex is a heteromer and comprises LRRC8A and at least one or more of LRRC8B, LRRC8C, LRRC8D and/or LRRC8E.

As demonstrated herein, the VRAC appears to function as a heteromer of multiple LRRC8 proteins, comprising, in a preferred embodiment, at least LRRC8A and one or more of LRRC8B, LRRC8C, LRRC8D and/or LRRC8E. Any given number or combination of LRRC8B, LRRC8C, LRRC8D and/or LRRC8E may be present in the complex that comprises LRRC8A. In a preferred embodiment the protein complex comprises a heteromeric complex of six LRRC8 proteins.

In one embodiment the method of the present invention is characterised in that the protein or protein complex is isolated or purified.

In one embodiment the method of the present invention is characterised in that providing a protein or protein complex comprises providing one or more cells or a cell line, preferably in cell culture, expressing one or more of LRRC8A, LRRC8B, LRRC8C, LRRC8D and/or LRRC8E.

The present invention relates preferably to in vitro methods, but may comprise in vivo or ex vivo methods. Such in vitro methods comprise in a preferred embodiment the use of a cell, cells, or cell line in culture, that express LRRC8 proteins. LRRC8 protein expression may relate to expression from endogenous nucleic acids, i.e. the genes encoding LRRC8A (or other LRRC8 proteins) already present in the genome of the cells, or to expression from exogenous nucleic acids. Exogenous nucleic acids may relate to expression vectors, such as plasmids or viral vectors, that are transformed into the cell, and either integrated or not integrated into the host cell genome. The expression of LRRC8 proteins will lead to presentation of said proteins at the plasma membrane, so that the VRAC complex is present (or resides) in the plasma membrane of the cell and is accessible for testing with candidate compounds.

In one embodiment the method of the present invention is characterised in that said contacting of one or more candidate substance(s) with said protein complex comprises administration of said candidate substance in solution to said protein complex, wherein during contacting of the candidate substance(s) with the protein or protein complex, said protein or protein complex is situated in a biological membrane.

The contacting of candidate compound with LRRC8-comprising complex may in one embodiment relate to administration of the compound to cells in culture, for example in a petri dish or flask, by immersing or treating the cells in liquid, in which the candidate compound is soluble and in solution. The LRRC8-comprising complex may in another embodiment be isolated and/or in solution. Purified protein or complex may be used for example in studies related to physical interaction between LRRC8 proteins and a candidate compound.

In one embodiment the method of the present invention is characterised in that determining the presence or absence of an interaction between said candidate substance(s) and said protein or protein complex comprises determining a change in the passage of a marker substance across a biological membrane.

A functional change in ion transport can be assessed using both the methods described herein and those known to a skilled person.

A marker substance is intended as a substance to assess the interaction between candidate molecule and channel components. Any number of components may be transported by the channel of the present invention, and therefore may be used as a component of the assay described herein.

In one embodiment the method of the present invention is characterised in that the marker substance is an ion, preferably an anion, such as chloride or iodide.

In one embodiment the method of the present invention is characterised in that the marker substance is an amino acid, such as a glutamate.

In one embodiment the method of the present invention is characterised in that the marker substance is taurine. As demonstrated in the examples below, taurine is capable of being transported by the channel of the invention and may be used as a read-out of channel function.

In one embodiment the method of the present invention is characterised in that the marker substance is an antibiotic or cytotoxic substance. Recent experimental work has demonstrated that antibiotic and cytotoxic substances are transported into cells by LRRC8 proteins. The method as described herein is therefore useful for assessing antibiotic transport into (and potentially out of) cells, and for the identification of channel modulators that may play a role in enhancing or suppressing antibiotic or cytotoxic transport.

In one embodiment the method of the present invention is characterised in that the marker substance is a fluorescent marker. Essentially any marker molecule capable of being tracked in the context of cellular influx or out flux in or from a cell is appropriate for application in the method as described herein. Methods for such assays are known to one skilled in the art. For example, one could test for ATP-release from the cells. ATP could then be detected in the medium by a luminescence assay or by radioactive labelling. Suitable methods are known to a skilled person.

In one embodiment the method of the present invention is characterised by determining the presence or absence of an interaction between said candidate substance(s) and said protein or protein complex comprises determining a physical interaction between said candidate substance and said protein or protein complex Physical interaction between candidate compounds and said complex may be determined by methods commonly known to those skilled in the art. Such methods include but are not limited to protein-protein interaction assays, such as immunoprecipitation, fluorescence assays such as standard fluorescent microscopy and co-localisation assays, fluorescence resonance energy transfer assays (FRET), demonstrating physical interaction and/or close proximity of complex and candidate compound, or other assays known to a skilled person. Further structural experimentation is also possible, such as crystal structure determination of bound candidate compound and complex.

For example, technology from Biacore may be applied for measuring protein-protein interaction and binding affinity. The technology is based on surface plasmon resonance (SPR), an optical phenomenon that enables detection of unlabeled interactants in real time. The SPR-based biosensors can be used in determination of active concentration as well as characterization of molecular interactions in terms of both affinity and chemical kinetics. An alternative assay that could be used for detecting molecular interactions is fluorescence cross-correlation spectroscopy (FCCS), or fluorescence correlation spectroscopy (FCS), which is a procedure that examines the correlation between different colours rather than just the same colour. In other words, coincident green and red intensity fluctuations correlate if green and red labelled particles are moving together. As a result, FCCS provides a highly sensitive measurement of molecular interactions independent of diffusion rate. FCCS typically utilizes two species which are independently labelled with two differently coloured fluorescent probes. These fluorescent probes are excited and detected by two different laser light sources and detectors usually labelled as "green" and "red". Typically a confocal microscope is used to provide overlapping green and red focal volumes for excitation.

In one embodiment the method of the present invention is characterised in that passage of a marker substance across a biological membrane, preferably of iodide, taurine, chloride and/or glutamate, is induced by cell volume increase (swelling), such as caused by administration of a hypotonic solution to one or more cells. In one embodiment the method of the present invention is characterised in that said determining of the presence or absence of an interaction between said candidate substance(s) and said protein complex comprises measuring anion flux, preferably iodide, taurine and/or chloride cellular influx, and/or glutamate cellular release.

In one embodiment the method of the invention is characterised in that iodide, taurine and/or chloride cellular influx and/or glutamate cellular release is induced by cell volume increase (swelling), such as caused by administration of a hypotonic solution to one or more cells expressing LRRC8A.

For example, the administration of hypotonic solution to a cell, or cell population, may cause cell swelling due to the influx of water due to osmosis. To counteract such swelling the cell will initiate extrusion of intracellular $Cl^-$ and $K^+$ ions, as well as other osmolytes, across the plasma membrane. To counteract this effect VRAC is activated upon swelling and will transport anions into the cell, for example iodine, taurine and/or chloride. The co-administration of a candidate inhibitor compound with the treatment of a cell with a hypotonic solution will enable testing of whether the VRAC function is modulated, for example inhibited, or not by said candidate compound. Appropriate control runs may be carried out, with either isotonic solution or known inhibitors of VRAC, in order to provide comparative values.

In one embodiment the method of the present invention is characterised in that said determining of the presence or absence of an interaction between said candidate substance(s) and said protein complex comprises the use of a cell or cell line expressing a fluorescent protein variant, preferably a yellow fluorescent protein variant, such as YFP(H148Q/I152L), wherein the fluorescence of said fluorescent protein variant is modulated, preferably quenched, by the presence of iodide, taurine and/or chloride.

In a preferred embodiment the method of the present invention is characterised in that one or more of LRRC8A, LRRC8B, LRRC8C, LRRC8D and/or LRRC8E protein function is disrupted or absent, for example in one or more cell or cell lines in which via deletion, mutation and/or anti-sense interference of the gene or other nucleic acid molecule encoding said protein.

In another preferred embodiment the method of the present invention is characterised in that one or more cell or cell lines are used in which one or more of LRRC8A, LRRC8B, LRRC8C, LRRC8D and/or LRRC8E is expressed from an exogenous nucleic acid.

Such approaches may enable determination of subunit-specific channel modulation by said candidate modulator substance. In such embodiments the interrogation of particular sub-unit contributions towards VRAC function and/or particular subunit-compound interactions is possible. Any given candidate compound may interact primarily with one sub-unit of the heteromeric VRAC. By subsequently and individually eliminating each of the subunits in turn further information can be obtained as to which subunit of the heteromeric complex is required for activity of the candidate compound.

In a preferred embodiment of the method, preferably in the form of an in vitro cellular assay, a control is carried out in which one or more of LRRC8A, LRRC8B, LRRC8C, LRRC8D and/or LRRC8E protein function is disrupted or absent, whereby preferably LRRC8A is disrupted in the control cells. In this embodiment the same candidate compound is applied to both LRRC8A-expressing cells (preferably from an endogenous LRRC8A gene) and as a control to cells in which LRRC8A is disrupted. Through such a method a specific effect of the candidate compound on the LRRC8A-comprising VRAC can be ascertained. In such an embodiment the method is preferably carried out using expression of LRRC8A from its endogenous promoter as provision of an LRRC8A-comprising protein complex, although the method could be potentially carried out using LRRC8A-encoding exogenous nucleic acids.

In one embodiment the method as described herein is described in that either a) a control is conducted using cells in which LRRC8A, LRRC8B, LRRC8C, LRRC8D and/or LRRC8E function is disrupted and/or b) one or more of LRRC8A, LRRC8B, LRRC8C, LRRC8D and/or LRRC8E is expressed from an exogenous nucleic acid transformed into either test or control cells.

Further combinations using different LRRC8 proteins, either disrupted or exogenously expressed, are also encompassed by the present invention.

The combination of expressing particular combinations of LRRC8 proteins also enables interrogation of cell-type or tissue- or organ-specific effects of any given modulator compound. The LRRC8 proteins are expressed at different levels in various tissues and cell types in vivo, enabling the provision of a test system that mirrors such specific expression levels. Modulators could therefore be screened and identified that show activity against a particular sub-combination of LRRC8 proteins that is known to be expressed in a certain cell type or organ/tissue, thereby providing active compounds that show reduced off target effects.

Recent work has uncovered that certain LRRC8 proteins are for example only very lowly expressed in certain tissues and cell types, for example LRRC8E is expressed only at negligible (very low) levels in neurons and blood cells (for example HL60 cells, derived from a neutrophilic promyelocyte). A protein complex could therefore be provided for the test system proposed herein that does not contain LRRC8E, or in which a cell line is provided that has had LRRC8E knocked out or knocked down by interference. Modulators that bind such a complex may then show tissue specificity for neurons or blood cells. Alternatively, target channel complexes could exhibit LRRC8E, thereby being used for the identification of inhibitors that do not bind neurons or blood cells.

Furthermore, it has been demonstrated that colon cancer cells (HCT116) express only very low levels of LRRC8C. A test system as described herein without LRRC8C could enable the provision or identification of compounds that show colon cancer cell specificity.

In light of the role of VRAC in the transport of cytotoxic compounds, a test system or assay as described herein can be provided, in which specific cancer cell or other pathologic cell type is profiled for its expression levels of multiple (preferably all) LRRC8 proteins, and subsequently a test system is provided that exhibits the corresponding complex components. Through such an assay compounds could be identified that may be responsible for VRAC activation, or channel activation that enhances cellular uptake of cytotoxic compounds in a cell-type specific manner, according to the VRAC components used in order to screen for said compounds.

For example, the subunit composition between neurons (relatively low amount of subunit E as judged from EST profile databases) and other brain cells (e.g. glia) could be markedoy different. Targeting specific combinations of LRRC8 subunits could therefore be, in one aspect of the invention, relevant for identifying channel modulators that are potentially useful in the treatment and/or prevention of brain ischemia (glutamate toxicity vs. cell volume regulation).

Furthermore, a further example of the provision of a specific LRRC8 sub-unit composition is in the case of beta cells, whereby beta cells within the pancreas may exhibit a different subunit composition in comparison to surrounding pancreatic cells and may be targeted specifically to treat diabetes. Even in cases where the exact subunit composition of the LRRC8 channel is not yet known for any given cell or tissue type, profiling is possible and may be carried out without undue effort, in order to determine which particular LRRC8 subunits are expressed in any given cell type and at which level.

The method as described herein therefore also may encompass the profiling (measuring of the level of expression via for example mRNA levels or protein levels) of LRRC8 subunits in any given cell or tissue type, preferably comparing these to other cell types where the LRRC8 subunits profiles are already known, and subsequent provision of an appropriate protein complex comprising the desired LRRC8 subunits, or a cell to be used in the method described herein, in which the desired LRRC8 proteins are expressed. This approach applies to any given (patho-) physiological function, in particular those described herein, even if the particular LRRC8 subunit composition is as yet unknown.

A further aspect of the invention relates to an isolated protein selected from the group consisting of LRRC8A, LRRC8B, LRRC8C, LRRC8D and/or LRRC8E.

In a preferred embodiment the invention relates to an isolated protein complex comprising one or more of LRRC8A, LRRC8B, LRRC8C, LRRC8D and/or LRRC8E.

In a preferred embodiment the invention relates to an isolated protein complex comprising LRRC8A and at least one or more of LRRC8B, LRRC8C, LRRC8D and/or LRRC8E.

The invention also therefore relates to the use of LRRC8 proteins selected from LRRC8A, LRRC8B, LRRC8C, LRRC8D and LRRC8E, or a protein complex comprising one or more of LRRC8A, LRRC8B, LRRC8C, LRRC8D and/or LRRC8E in a method for the identification of a channel modulator. The use may preferably comprise application of said complex in a method as described herein. All features disclosed in context of the method also apply to said use.

In a further aspect the invention relates to an isolated heteromeric protein complex comprising one or more LRRC8 proteins, preferably LRRC8A. Until the present time, the VRAC has not been identified for isolation. The VRAC may be isolated according to standard procedures, for example by creating a "tagged" fusion protein and immunoprecipitation with an antibody directed against the tag. Immunoprecipitation could also be carried out using antibodies directed against the complex subunits directly. Suitable antibodies and protein tags suitable for immunoprecipitation are known to those skilled in the art. Reconstitution of the complex by expression of the complex subunits via recombinant protein expression is also possible.

In one embodiment the protein complex as described herein is characterised in that the complex comprises LRRC8A and one or more of LRRC8B, LRRC8C, LRRC8D and/or LRRC8E. As shown in the experimental examples, the LRRC8 proteins form heteromeric protein complexes, as various LRRC8 proteins co-precipitate with each other in appropriate immunoprecipitation experiments.

Further experimental evidence does also support the existence of complex formation without LRRC8A, whereby functionally relevant complex formation occurs with various combinations of other LRRC8 proteins.

The invention further relates to a channel, preferably an anion channel (VRAC), comprising one or more of LRRC8A, LRRC8B, LRRC8C, LRRC8D and/or LRRC8E, comprising preferably LRRC8A, wherein said channel comprises an isolated protein complex or a protein complex preferably present in a biological membrane. LRRC8 proteins have not previously been characterised as VRAC channel proteins. The provision of a channel comprising preferably one or more of LRRC8A, LRRC8B, LRRC8C, LRRC8D and/or LRRC8E represents a novel development in the art. It was entirely surprising that LRRC8 proteins are structural components of the VRAC complex.

The invention relates in a further aspect to a kit for carrying out a method for the identification of a channel modulator, comprising at least one of a) to c) and at least one of d) or e):
  a. LRRC8 protein selected from one or more of LRRC8A, LRRC8B, LRRC8C, LRRC8D and LRRC8E, or a protein complex comprising one or more of LRRC8A, LRRC8B, LRRC8C, LRRC8D and/or LRRC8E;
  b. One or more expression vectors encoding and capable of expressing one or more of LRRC8A, LRRC8B, LRRC8C, LRRC8D and LRRC8E; and/or
  c. A cell or cell line expressing one or more of LRRC8A, LRRC8B, LRRC8C, LRRC8D and LRRC8E;
  and (preferably)
  d. One or more cells or cell lines in which one or more of LRRC8A, LRRC8B, LRRC8C, LRRC8D and/or LRRC8E protein function is disrupted or absent, for example via deletion, mutation and/or anti-sense interference of the gene or other nucleic acid molecule encoding said protein, or a genetic construct such as a vector suitable for obtaining said disruption; and/or
  e. One or more cells or cell lines in which one or more of LRRC8A, LRRC8B, LRRC8C, LRRC8D and/or LRRC8E are expressed from an exogenous nucleic acid, or a genetic construct such as a vector suitable for such expression;
  and optionally
  f. a cell or cell line expressing a fluorescent protein variant, wherein the fluorescence of said fluorescent protein variant is modulated, preferably quenched, by the presence of iodide and/or chloride, wherein said fluorescent protein variant is YFP(H148Q/I152L); or a genetic construct such as a vector capable of expressing said fluorescent protein variant;
  g. one or more candidate (channel modulator) substances;
  h. Hypotonic solution and/or iodide, taurine and/or chloride solution; and/or
  i. Means for contacting said candidate substances with said LRRC8A protein or a protein complex comprising LRRC8A, or a cell or cell line expressing said LRRC8A protein or a protein complex comprising LRRC8A, such as cell culture equipment.

Also part of the present invention are computing devices, comprising: a processor and optionally, a tangible computer-readable medium, configured to comprise instructions that, when executed by the processor, are configured to cause the computing device to perform any one of the methods disclosed herein (see, e.g., US Patent Publication 20140349871, which is incorporated herein by reference in its entirety as are all other references referred to herein, including the literature references listed throughout the application and also set forth in the section entitled "References").

A kit for carrying out such a screening method may comprise one or more of kit components a) to i). In particular, the kit will comprise those components essential for carrying out the method described herein without necessarily comprising common laboratory items. Hypotonic solutions, or solutions containing iodide or chloride, may be produced via standard methods known to those skilled in the art. In a preferred embodiment the kit comprises those aspects of the invention suitable for interrogating specific sub-combinations of the various LRRC8 proteins, either via disruption or expression from exogenous nucleic acids.

The kit may comprise such solutions at appropriate concentrations for directly carrying out the method (see for example the experimental examples) or in concentrated form. The kit may comprise the vectors or cell lines required for testing specific complex subunits. Such cell lines may also be transformed with appropriate genetic material encoding and capable of expressing a fluorescent protein variant sensitive to ion influx, for example YFP(H148Q/I152L).

The method and products of the present invention are of particular clinical relevance. Previous work on VRAC/VSOAC function has described a number of clinically relevant functions that can be ascribed to regulation of this channel. In light of the identification of the molecular components of the channel, modulators of the channel represent clinically relevant substances that may be used in various therapeutic regimes.

For example, Hoffmann et al (1) describe a number of clinical areas in which cell volume is important for signalling and cellular function with respect to pathology. VRAC/VSOAC function is known to play an important role in transepithelial transport, regulation of metabolism, hormone release, cell contraction, cell migration, cell proliferation and tissue necrosis. Programmed cell death and cell differentiation are two further potential cellular functions mediated by VRAC/VSOAC.

Experimental support has been provided for a role for VRAC/VSOAC in cell migration and invasion, for example with respect to metastasis. Activation of swelling activated VRAC has been shown to facilitate cell migration. The increased migratory capacity of H-Ras-transformed NIH3T3 fibroblasts is also related to volume sensitivity of VRAC. VRAC inhibitors may therefore represent potential inhibitors of metastasis. Additional support exists for non-specific VRAC inhibitors, in that such inhibitors (eg NS3728) have been shown to inhibit cell migration more strongly in Ras-transformed cells compared to WT cells.

Cell shrinkage is also a known indicator for programmed cell death (PCD; also known as apoptotic volume decrease (AVD)). VRAC has been shown to be involved in AVD in HeLa cells and endothelial cells, amongst other cell types. Studies also exist in which cisplatin (toxic to cancer cells and PCD inducing) has been shown to activate VRAC in human epidermis cancer cells. Non-specific Cl-channel inhibitors that target VRAC are also known to delay/inhibit apoptosis, providing further support for the relevance of specific LRRC8 channel modulators, that may be identified by the method described herein, with respect to cancer treatment.

Furthermore, Cl-channels such as VRAC have been widely reported to be involved in the control of cell proliferation. VRAC inhibitors therefore represent potential inhibitors of cell proliferation, again suggesting potential application in cancer treatment.

Additional therapeutic indications for potential VRAC modulators relate to modulating cell permeability to antibiotic or cytotoxic substances. As mentioned herein, recent experimental work provides support that certain antibiotics are transported in a cell volume dependent (VRAC mediated) manner. The invention therefore also relates to the provision of compounds that activate VRAC activity, thereby enhancing permeability of the cells to cytotoxic agents or to enhance antibiotic uptake. In particular the variant LRRC8D has been implicated in antibiotic uptake. One particular example of clinical application relates to reducing cytostatic resistance, whereby potentially therapeutic anti-cancer substance are not taken up by the cell. VRAC modulator could potentially be identified that increase cytostatic permeability into the cell, either directly via VRAC or indirectly, due to the modulation of cell volume and subsequent uptake by an alternative transporter.

Further experimental support exists for a role of VRAC/VSOAC in the electrical activity of pancreatic islet cells. Recent studies have proposed that Beta cells are equipped with a volume-regulated anion channel that is activated by glucose concentrations within the range effective in modulating insulin release. VRAC modulators could therefore be developed that modulate insulin release, providing potentially medicinal candidate compounds for administration in diabetes therapy.

The present invention therefore also relates to a method for the provision of a therapeutic compound (candidate compound tested in the method described herein) for use as a medicament. The method of the present invention therefore may further comprise formulating the identified compound that exhibits channel modulation activity in a pharmaceutically acceptable form. The method may also encompass mixing the identified compound with a pharmaceutically acceptable carrier, whereby the pharmaceutical composition is suited for application in the treatment of a medical condition. Preferred medical conditions relate to cancer, relating to preferred embodiments such as inhibition of cell proliferation, metastasis inhibition or enhanced cell permeability of cytotoxic agents, infectious diseases, for example for increased cell permeability for antibiotics, or diabetes. Essentially any medical indication associated with cell volume regulation and transport of ions or organic substances across the cell membrane may potentially be addressed, in particular by the identification of active compounds that show specific (preferably cell- or tissue-specific) modulatory activity against the LRRC8 proteins and/or complexes thereof described herein.

The VRAC channel has been implicated in other clinically relevant scenarios, which are also encompassed by the present invention. For example, the VRAC channel as described herein is known to transport ATP, taurine and glutamate across the cell membrane. These molecules have been suggested to function as neurotransmitters or co-transmitters, and may therefore also be passaged across the membrane via VRAC from neurons. The modulators identified by the method described herein may therefore be relevant in modulating neuron function with respect to the release of neurotransmitters.

DETAILED DESCRIPTION OF VARIOUS AND PREFERRED EMBODIMENTS OF THE INVENTION

Regulation of cell volume is critical for many cellular and organismal functions, but the molecular identity of a much-studied channel, the volume-regulated anion channel VRAC, has remained unknown. The present invention reveals that VRAC defines a novel class of channel and provides means for identifying VRAC modulators in addition to relating to the VRAC components themselves. In light of the previous work carried out on VRAC/VSOAC, a number of cellular and potentially clinically relevant functions have been elucidated, therefore enabling the present invention to provide active compounds directed as modulators of the channel described herein for a multitude of clinically relevant applications.

According to the invention a channel modulator may relate to a channel agonist (activator) or antagonist (inhibitor). Channel activation and inhibition may be assessed by the methods disclosed herein or other methods known to those skilled in the art. Generally, channel modulation may be determined via measurement of ion or organic substance flux (passage) across a biological membrane, for example in a cellular assay.

The term channel relates to a substance or combination of multiple substances that enable transport or passage of any given compound across a biological membrane. Such substances are typically not lipids, or lipid-like compounds forming the biological membranes themselves. Preferred embodiments of channels relate to ion channels, or channels for organic substances, that comprise protein complexes and are situated in a biological membrane.

The LRRC8 proteins (leucine-rich repeat-containing protein 8) described herein relate preferably to human proteins, but may also relate to any given mammalian orthologue or homologue. Protein and gene sequences may be obtained from any given genomic database, such as the NCBI protein or gene databases. Sequence variants of the mammalian, preferably human sequences, of the LRRC8-encoding nucleic acids or proteins are encompassed within the scope of the present invention. In some embodiments LRRC8-encoding nucleic acids and/or proteins with more than 70%, more than 80% or preferably more than 90% sequence identity to the human LRRC8 sequences are encompassed in the invention. The term LRRC8 may relate to any given LRRC8 protein selected from LRRC8A, LRRC8B, LRRC8C, LRRC8D or LRRC8E.

According to this invention, tonicity is a measure of the osmotic pressure gradient (as defined by the water potential of the two solutions) of two solutions separated by a semipermeable membrane. It is commonly used when describing the response of cells immersed in an external solution. Hypertonic refers to a greater concentration. A hypertonic solution is one with a higher concentration of solutes outside the cell than inside the cell. When a cell is immersed into a hypertonic solution, the tendency is for water to flow out of the cell in order to balance the concentration of the solutes. Hypotonic refers to a lesser concentration. A hypotonic solution has a lower concentration of solutes outside the cell than inside the cell. In an attempt to balance the concentrations of solutes inside and outside the cell, water will enter the cell, causing it to swell and even burst. An isotonic solution is one in which its effective osmole concentration is the same as the solute concentration of a cell. In this case the cell neither swells nor shrinks because there is no concentration gradient for water across the cell membrane. Water molecules diffuse through the plasma membrane in both directions, and as the rate of water diffusion is the same in each direction that cell will neither gain nor lose water.

A protein complex according to the invention relates to a group of two or more physically associated polypeptide chains, which may be either the same or different. Protein complexes may be considered a form of quaternary structure. Proteins in a protein complex are typically linked by non-covalent protein-protein interactions, and different protein complexes have different degrees of stability over time and under different conditions. Heteromeric protein complexes relate to protein complexes comprising at least two different physically associated polypeptide chains.

According to the invention the term isolated, for example with respect to isolated protein or an isolated protein complex, relates to an entity, for example a protein or protein complex that has been removed from its cellular environment and is present in a relatively higher concentration compared to background components in comparison to its endogenous cellular environment. An isolated protein may, but does not necessarily, relate to a purified protein, in the sense that no significant background component or contaminant is present. Isolated proteins will often be contaminated with some level of background protein, albeit at an extent less than commonly found in a crude cellular homogenate or in a cellular environment. The term isolated or purified may relate to proteins or protein complexes that have been isolated or purified according to techniques commonly known to a skilled person without having to demonstrate total or complete isolation or purity. Purified or isolated proteins may also be reconstituted with membrane components in vitro, in order to form membranes loaded with VRAC components for testing.

The term isolation refers to the process by which an entity is isolated, and in the case of a protein or protein complex may refer to protein purification, whereby multiple methods are already known in the art, such as precipitation and differential solubilization, Ultracentrifugation, Size exclusion chromatography, Hydrophobic Interaction Chromatography, Ion exchange chromatography, Affinity chromatography, Metal binding, Immunoaffinity chromatography, immunoprecipitation, Purification of a tagged protein, HPLC or Ultrafiltration. Such purification or isolation methods can be carried out without undue skill and may be applied to the proteins and protein complexes as described herein.

According to the present invention a membrane, biological membrane or biomembrane is an enclosing or separating membrane that acts as a selectively permeable barrier. Biological membranes, in the form of cell membranes, often consist of a phospholipid bilayer with embedded, integral and peripheral proteins used in communication and transportation of chemicals and ions. The phospholipid bilayer contains a charged hydrophilic head, which interacts with polar water. It also contains a hydrophobic tail, which meets with the hydrophobic tail of the complementary layer. This maintains the fluidity of a cell. Distinct types of membranes also create intracellular organelles, such as endosome; smooth and rough endoplasmic reticulum; sarcoplasmic reticulum; Golgi apparatus; lysosome; mitochondrion (inner and outer membranes); nucleus (inner and outer membranes); peroxisome; vacuole; cytoplasmic granules; cell vesicles (phagosome, autophagosome, clathrin-coated vesicles, COPI-coated and COPII-coated vesicles) and secretory vesicles (including synaptosome, acrosomes, melanosomes, and chromaffin granules). Different types of biological membranes have diverse lipid and protein compositions.

The biological cell is a basic structural and functional unit of all known living organisms, and according to the present invention may relate to a living, non-living or artificial cell. All cells have a membrane that envelops the cell, regulates what moves in and out (selectively permeable), and maintains the electric potential of the cell. Inside the membrane of a living biological cell, a salty cytoplasm takes up most of the cell volume. The cell membrane, or plasma membrane, according to the present invention surrounds the cytoplasm of a cell. In animals, the plasma membrane is the outer boundary of the cell. This membrane serves to separate and protect a cell from its surrounding environment and is made mostly from a double layer of phospholipids, which are amphiphilic (partly hydrophobic and partly hydrophilic).

Synthetic biological membranes are also known in the art and may be used in the present invention, such as artificial cells. Artificial or minimal cells are engineered particles that mimic one or many functions of a biological cell. Often, artificial cells are biological or polymeric membranes which enclose biologically active materials. As such, nanoparticles, liposomes, polymersomes, microcapsules and a number of other particles have qualified as artificial cells. Such artificial cells or membrane particles also are considered biological membranes according to the present invention.

The term express or expression relates to gene and/or protein expression. As is commonly known in the art, a nucleic acid may be expressed by transcription (DNA to RNA), and subsequently translation (RNA to protein). Gene or protein expression may be determined via multiple techniques, such as those for nucleic acids (southern blotting, northern blotting, polymerase chain reaction (PCR)), or those for protein (western blotting, analytical chemistry, mass spectrometry). Exogenous nucleic acids relate to any given nucleic acid that is not comprised in the original genome of the organism in question. An exogenous element may therefore relate to an expression vector, transformed into a cell, either integrated or non-integrated into the hosts genome. Exogenous nucleic acids also relate to short nucleic acids such as DNA, RNA, LNA etc that may be transfected, transformed or expressed from a vector within the cell, in order to obtain a modulation or disruption of gene expression.

The term providing according to the present invention relates making available for use; or supply or provision of any given entity. The term contacting relates preferably to a physical interaction between any given entities. Contacting may also encompass indirect contact, where for example a candidate compound indirectly interacts with a protein or protein complex via an intermediate molecule. The term administration also refers essentially to the provision and giving of and/or contacting of any particular entities. The term determining relates to identification, measurement and/or realisation of any given effect.

According to the invention the term candidate compound relates to any given molecule or chemical entity to be tested as a modulator of VRAC structure or function. The candidate compound may be one or more of a small molecule, a nucleic acid, a protein, or any other organic, inorganic or biological molecule. Such candidate compounds may be present in libraries, such as those used commonly in screening methods for active compounds in pharmaceutical procedures, or biological libraries, for example of short interfering RNA molecules directed to various genes, or other compound libraries such as natural product libraries comprising isolated compounds obtained from natural sources.

The terms deletion and mutation relate to their common definitions as understood by one skilled in the art. A deletion may relate to the removal of any gene or any part of a gene from the genome of the cell or cell line used in the method. The removed sequence may relate to either coding sequence or any regulatory sequence with the effect that gene expression is disrupted. A mutation may relate to any change of the nucleotide sequence of the genome of an organism, virus, or extrachromosomal genetic element, preferably a substitution, insertion, addition and/or deletion of any given region of nucleic acid sequence.

The term anti-sense interference relates broadly to any administration of nucleic acids, preferably RNA, which based on its complementary to a target sequence subsequently leads to modification of gene expression. As an example, antisense RNA (asRNA) is a single-stranded RNA that is complementary to a messenger RNA (mRNA) strand transcribed within a cell. Antisense RNA may be introduced into a cell to inhibit translation of a complementary mRNA by base pairing to it and physically obstructing the translation machinery. RNA interference (RNAi) is a related process in which double-stranded RNA fragments called small interfering RNAs (siRNAs) trigger catalytically mediated gene silencing, most typically by targeting the RNA-induced silencing complex (RISC) to bind to and degrade the mRNA. These small RNAs can bind to other specific messenger RNA (mRNA) molecules and either increase or decrease their activity, for example by preventing an mRNA from producing a protein. The RNAi pathway is initiated by the enzyme Dicer, which cleaves long double-stranded RNA (dsRNA) molecules into short double stranded fragments of ~20 nucleotide siRNAs. Each siRNA is unwound into two single-stranded (ss) ssRNAs, respectively the passenger strand and the guide strand. The passenger strand is degraded and the guide strand is incorporated into the RNA-induced silencing complex (RISC). Post-transcriptional gene silencing occurs when the guide strand pairs with a complementary sequence in a messenger RNA molecule and induces cleavage by Argonaute, the catalytic component of the RISC complex. The design of appropriate antisense RNA or siRNA is known in the art, can be carried out as required and demands no inventive effort on the part of a skilled person.

DETAILED DESCRIPTION OF THE FIGURES

FIG. 1. siRNA screen for volume-regulated anion channel VRAC identifies LRRC8A. (A) Principle of screen. Top, in regulatory volume decrease (RVD) VRAC releases chloride. Below, quenching of YFP fluorescence by iodide entering through VRAC used as read-out. (B) Example traces, normalized to fluorescence at ~30-50 s. Averaged from wells treated with control siRNAs (scrambled, AE2, both n=3) and no siRNA (n=2) (error bars, SEM), and individual traces from wells singly transfected with the 3 siRNAs against LRRC8A. Except for LRRC8A siRNA2 and 3, all traces are from the same plate. Arrow indicates addition of iodide-containing hypotonic (hypo; 229 mOsm) or isotonic (iso; 329 mOsm) saline. (C) Secondary screen using siRNA pools against candidate genes. Averaged control traces as above. (D) Typical time course of VRAC activation in WT or LRRC8A siRNA-treated HEK cells. Current densities at −80 mV are shown. Bar, application of hypotonic (240 mOsm) saline (hypo). (E) Current traces of fully activated $I_{Cl(swell)}$ measured using the protocol shown below. Dotted lines indicate zero current. (F) $I_{Cl(swell)}$ amplitudes (at −80 mV) of WT HEK cells, cells treated with LRRC8A siRNA, or transfected with indicated LRRC8 cDNAs. Error bars, SEM; number of experiments is indicated; ***, p<0.001.

FIG. 2. Subcellular localization of LRRC8 proteins. (A) Plasma membrane localization of LRRC8A-GFP transfected into HeLa cells detected by GFP labeling. (B) Plasma membrane residence of endogenous HEK LRRC8A detected by LRRC8A antibody. (C) No LRRC8A labeling in LRRC8A$^{-/-}$ HEK cells. (D) Truncated LRRC8A fused at R719 to GFP failed to reach the plasma membrane. (E-H) Intracellular localization of LRRC8B-E when transfected alone. (I-L) LRRC8B-E reach the plasma membrane when co-transfected with LRRC8A. Insets, magnification of boxed areas showing exclusively GFP fluorescence. Scale bar, 10 µm for all panels.

FIG. 3. Characterization of LRRC8 KO cell lines. (A) Genomic sequencing of LRRC8A$^{-/-}$ HCT116 cell line 3F8 reveals a frameshift at G43 on both alleles. Guide sequence in bold, PAM sequence (37) underlined. (B) Western blots confirm LRRC8A disruption in mutant cell lines. α-tubulin, loading control. (C) Absence of $I_{Cl(swell)}$ in LRRC8A$^{-/-}$ HEK cells and rescue by LRRC8A-GFP transfection. (D) Example $I_{Cl(swell)}$ traces (as in FIG. 1E, but 2-s pulses) of WT and mutant HCT116 cells. (E) Current densities of maximally activated $I_{Cl(swell)}$ (at −80 mV) of WT and mutant HCT116 cells. Mean±SEM, number of cells is indicated. , p<0.01 and *, p<0.001 vs. WT. (F) $I_{Cl(swell)}$ inactivation assessed by ratio of current at end/beginning of pulse ($I_{2sec}/I_{max}$). V1/2 from Boltzmann fits (in mV): HEK, 81.7±2.7; HCT116, 59.1±1.5; HCT116 derivates: LRRC8B$^{-/-}$, 63.3±2.4; LRRC8C$^{-/-}$, 25.3±6.0; LRRC8E$^{-/-}$, 59.0±2.1; LRRC8(D/E)$^{-/-}$, 76.7±8.5; LRRC8(C/E)$^{-/-}$, 37.6±4.3. (G) Time needed to inactivate to 50% of the difference between currents at beginning and end of pulse.

FIG. 4. Reconstitution of $I_{Cl(swell)}$ in the quintuple KO cell line LRRC8. (A) When transfected into HCT116 LRRC8$^{-/-}$ cells (with all LRRC8 genes disrupted), LRRC8A rescues ICl(swell) only together with LRRC8C, D or E. (B) $I_{Cl(swell)}$ current densities (at −80 mV) of cells indicated. *, p<0.05 and ***, p<0.001 vs. WT. Numbers of measured cells are indicated. (C) Voltage-dependent inactivation of ICl(swell) measured by $I_{2sec}/I_{max}$ and (D), by speed of inactivation as in FIGS. 3, F and G. $_{V1/2}$ from Boltzmann fits (in mV): WT HCT116, 59.1±1.5; LRRC8A+C, 115.8±2.7; LRRC8A+D, 72.4±2.8; LRRC8A+E, 45.9±2.1. (E), mRNA expression of LRRC8A-E in HEK, HCT116, and HL-60 cells determined by quantitative RTPCR. Values were normalized to the respective value of HEK cells. Means from 4 experiments. Error bars, SEM.

FIG. 5. Transmembrane topology and heteromerization of LRRC8A. (A) Schematic diagram of LRRC8 protein (modified from (Abascal et al.)). Four transmembrane domains precede a Cterminus with up to 17 leucine-rich repeats (Smits et al.) (orange). Predicted N-linked glycosylation sites (Y) and added epitopes (HA or GFP) are indicated. (B) Western blot probed with LRRC8A antibody showed that PNGaseF treatment of endogenous LRRC8A, transfected LRRC8A, but not of the LRRC8A(N66A, N83A) mutant lacking the predicted glycosylationsites, led to a decrease in size. The changed banding pattern of the mutant might result from altered posttranslational modifications. n.t., non-transfected. (C) Immunofluorescence using HA antibody of non-permeabilized versus permeabilized HeLa cells transfected with GFPLRRC8A carrying an HA-tag as indicated. Overlays of GFP (green) and HA (red) labeling. Insets show exclusively HA-staining. Scale bar, 20 µm. (D) LRRC8A co-precipitated epitopetagged LRRC8B through LRRC8E in double-transfected HEK cells. LRRC8B and LRRC8D were poorly expressible. (E) LRRC8A did not co-precipitate the ClC-1 Cl⁻ channel. (F) Epitope-tagged LRRC8B through LRRC8E co-precipitated LRRC8A. (G) Heteromerization of endogenous LRRC8 proteins. LRRC8A co-precipitated LRRC8E (for which a suitable antibody was available) in immunoprecipitation with an LRRC8A antibody from wild-type (WT) HEK cell lysate, but not from the LRRC8A−/− knockout (KO, clone 3E7). The plasma membrane ion transporter KCC1 (negative control) did not co-precipitate with LRRC8A. Lysate equivalent to 25% of input was loaded as reference (input).

FIG. 6. LRRC8 proteins are indispensable for swelling-induced efflux of taurine. (A and B) Essential role of LRRC8A in $^3$[H]-taurine efflux from HEK (A) and HCT116 cells (B). WT cells (HEK or HCT116) were in isotonic solution throughout, whereas another set of WT and LRRC8A$^{-/-}$ cells were exposed to hypotonic solution starting at t=0 (arrows). Similar results were obtained with experiments for each cell line. (C) Taurine efflux in HCT116 cells with disrupted LRRC8B-E genes (LRRC8(B/C/D/E)$^{-/-}$). Bars, means of 6 measurements of efflux between the time points indicated; error bars, SEM. (D) Taurine efflux measurement as in (A), but the LRRC8A−/− HEK cells had been co-transfected with LRRC8A and LRRC8C-GFP. This co-transfection partially restores the taurine flux capability of LRRC8A−/− HEK cells. Co-transfection was necessary as overexpression of LRRC8A alone leads to a suppression of ICl(swell). Only partial rescue of fluxes with transfected cells agrees with the transfection efficiency of roughly 50%.

FIG. 7. Effect of carbenoxolone on hypotonicity-induced YFP quenching by iodide. Fluorescence trace from a FLIPR™ experiment similar to those in FIG. 1C in which the effect of carbenoxolone (CBX), an inhibitor of VRAC and gap junctions (Benfenati et al.), was investigated. Carbenoxolone was included in the I⁻-containing solution and added at the time point indicated by arrow.

FIG. 8. Genome-wide RNA interference screen for VRAC. (A) Plate lay-out. Cells in wells of rows 1-22 were transfected with individual siRNAs of the Ambion Silencer® Human Genome siRNA Library V3 and tested for hypotonicity-induced YFP-quenching (experimental wells). Rows 23 and 24 contained control wells that were treated as indicated. (B) Photograph (inverted) of YFP fluorescence of an entire plate before the pipetting step (top) and at the end of the experiment (below). Note that fluorescence of cells treated with siRNA against YFP and cell-death inducing siRNA is strongly reduced at the beginning of the experiment (top) (transfection control). At the end of the experiment (bottom), fluorescence has remained strong in wells remaining in isotonic solution throughout. Arrows indicate well H11 containing cells transfected with the most efficient siRNA against LRRC8A. (C) Heat map of the same plate. Z-scores for $S_{max}$ (maximal slope of quenching) are displayed using the color scale shown at right.

FIG. 9. Analysis of the primary, genome-wide siRNA screen for VRAC. (A and B) Parameters derived from the primary siRNA screen for VRAC. (A) Example of original data obtained from the FLIPR™ primary genome-wide screen, showing the absolute, noncorrected values of fluorescence ($F^{abs}$) measured at Ä=526-585 nm as a function of time. The top curve shows a representative trace from an experimental well with YFPexpressing HEK cells that have been treated with siRNA and were exposed to hypotonic, iodide-containing solution at the time indicated by the arrow. The bottom curve shows a control well from the same plate to which hypotonic, iodide-containing solution containing 1% Triton X100. (B) Background-subtracted and normalized fluorescence F*. After subtracting the background determined in control wells treated with Triton X100, the fluorescence of every experimental well was normalized to its individual $F^{abs}$ start value. The maximal slope of fluorescence decrease $S_{max}$ was determined by linear regression to the curve between 35 and 300 seconds and was used as main parameter to identify hits. $t_{onset}$ was defined as indicated and can be used as measure of the speed of signal transduction between volume increase and VRAC opening. (C and D) Fidelity of replicate screens. Correlation of Z-scores of maximal slope $S_{max}$ between the original and the replicate screen observed with all 65,061 siRNAs (C) and after filtering out those measurements that were flagged for low cell number or did not reach near-steady-state fluorescence by the end of the measurement (D). Z-scores from screen 1 and screen 2 are plotted on the x- and y-axis, respectively. The Pearson correlation coefficient (r=0.62 and r=0.65, respectively) indicates positive correlation between replicate screens. The regression line from simple linear regression is shown as a dashed red line. The elimination of outliers demonstrated the usefulness of these warning flags. (E) Histogram of Z-scores for maximal slope ($S_{max}$) from the genome-wide siRNA screen. Measurements which were flagged for low cell number or did not reach steady state fluorescence by the end of measurement were filtered out, resulting in values for 50,258 siRNAs. The averaged Z-scores from screen 1 and screen 2 are plotted. Arrows indicate the Z-scores of three individual siRNAs against LRRC8A (0.125, 0.809 and 2.217).

FIG. 10. Absence of $I_{Cl(swell)}$ in independent LRRC8A$^{-/-}$ cell lines. (A) Western blot with LRRC8A antibody confirms the disruption of LRRC8A in the HCT116 clone ZF9 (generated with zinc-finger nuclease) α-tubulin, loading control. (B) Amplitudes of maximally activated $I_{Cl(swell)}$ (at −80 mV) of WT HEK, WT HCT116 and different LRRC8A$^{-/-}$ cell lines, rescued by transfection of LRRC8A-GFP cDNA. Note that the amplitude of $I_{Cl(swell)}$ current was not fully rescued in HEK cells by LRRC8-GFP transfection, an observation that fits to the suppression of $I_{Cl(swell)}$ from native HEK cells by LRRC8A transfection (FIG. 1F). Mean currents±SEM, number of measurements is indicated. , p<0.01 and *, p<0.001 compared to WT HEK or WT HCT116, respectively. For description of different cell lines see table S4.

FIG. 11. Characterization of LRRC8A and LRRC8E antibodies. (A) Western blots of lysates from wild-type (WT) and LRRC8A−/− (clone 3F8) HCT116 cells, and from HeLa cells that were not transfected (n.t.), or transfected with LRRC8A or with LRRC8A and LRRC8C GFP fusion proteins were probed with the LRRC8A antibody, or antibodies against GFP and α-tubulin (loading control) as indicated. The LRRC8A antibody recognizes native and overexpressed LRRC8A specifically. (B) Western blots of lysates from WT, LRRC8A−/− (clone 4B9) and LRRC8E−/− (clones BCDE(WT)-F5 and CE(WT)-B6) HCT116 cells, and from HeLa cells that were not transfected (n.t.) or transfected with LRRC8A or LRRC8E GFP fusion proteins were probed with antibodies against LRRC8A, LRRC8E and α-tubulin. The LRRC8E antibody recognizes specifically native and overexpressed LRRC8E, whereas LRRC8E is not recognized by the LRRC8A antibody. (C) HeLa cells methanol-fixed and immunostained with the LRRC8A antibody (red in overlay) 24 h after transfection with LRRC8A (upper panel) and LRRC8C (bottom panel) GFP fusion proteins (GFP signal, green in overlay), nuclei in blue. The LRRC8A antibody recognizes specifically overexpressed LRRC8A. Scale bars, 20 μm. (D) Higher exposure of non-transfected HeLa cells reveals plasma membrane staining with the LRRC8A antibody (red; nuclei in blue). Scale bar, 20 μm.

FIG. 12. Characterization of ICl(swell) in HCT116 cells. (A) Relative anion permeabilities (PX/PCl) as determined from shifts in reversal potential of ICl(swell) upon anion substitution in WT, LRRC8 knock-out HCT116 cell lines, and (B) LRRC8−/− cells transfected with the combinations indicated. Mean±SEM, number of cells=4. (C) Example current-voltage relationships obtained at the time of maximal current activation of endogenous and reconstituted ICl(swell) with normal and anion substituted hypotonic extracellular solutions. Insets show a magnification of reversal potentials for Cl—, I— and NO3. The reversal potential is shifted to slightly more negative voltages when extracellular Cl— is replaced by I— and NO3 and to drastically more positive voltages upon replacement by D-gluconate. (D-E) Voltage-dependent ICl(swell) inactivation assessed by time needed to inactivate to 50% of the difference between currents at end/beginning of pulse (12 sec/Imax). In panel E, constructs were transfected into the quintuple KO HCT116 cell line (LRRC8−/−). Numbers in brackets indicate the number of cells measured.

FIG. 13. Heteromerization of LRRC8 proteins in absence of LRRC8A. Epitope (myc)-tagged LRRC8C co-precipitated GFP-tagged LRRC8E and myc-tagged LRRC8E co-precipitated GFP-tagged LRRC8C (but both did not co-precipitate GFP) in double-transfected HEK cells, independent of whether endogenous, functional LRRC8A was present (WT) or absent (KO).

EXAMPLES

The invention is further described by the following examples. The examples relate to a practical and in some cases preferred embodiments of the invention that do not limit the scope of the invention.

The experimental examples relate to a genome-wide siRNA screen in mammalian cells, which has identified LRRC8A as a VRAC component. The examples also reveal that LRRC8A formed heteromers with LRRC8B through LRRC8E, which all have four transmembrane domains and C-terminal leucine-rich repeats. Genomic disruption of LRRC8A ablated VRAC currents. LRRC8−/− cells, in which all five LRRC8 genes were disrupted, required LRRC8A co-transfection with other LRRC8 isoforms to reconstitute VRAC currents. The subunit composition determined their inactivation kinetics. Taurine flux also depended on LRRC8 heteromers. Protein complexes with multiple LRRC8 proteins, but without LRRC8A have also been isolated. The experiments are described in more detail as follows:

LRRC8A is Indispensable for ICl(Swell)

To identify VRAC we opted for a genome-wide RNA interference screen that could identify non-redundant VRAC components even if the channel were a heteromer. Swelling-induced iodide influx into HEK cells, which display typical $I_{Cl(swell)}$ currents (Nilius et al., 2001, Hernandez-Carballo et al.), was used as readout (FIG. 1A). We generated a clonal HEK cell line expressing a yellow fluorescent protein variant YFP(H148Q/I152L) whose fluorescence is efficiently quenched by iodide (Galietta et al.). The assay used the FLIPR™ fluorometric imaging plate reader system which allows parallel pipetting and continuous fluorescence measurements of all wells. The solution covering the cells was exchanged to a hypotonic or isotonic (control) saline containing 50 mM iodide and YFP fluorescence was followed over time (FIG. 1B). Compatible with a background permeation pathway for I− the fluorescence decayed slowly in I−-containing isotonic control solution. Exposure to hypotonicity induced a delayed, robust increase in YFP quenching (FIG. 1B). This decrease in fluorescence depended on the presence of iodide and could be partially inhibited by several non-specific inhibitors of VRAC including carbenoxolone (Benfenati et al.) (FIG. 7) and DCPIB (Decher et al.). In a prescreen we targeted 21 known anion transporters (table S1) with pools of siRNAs to test their role in iodide uptake. Only the siRNA pool against the Cl/HCO3-exchanger AE2 (SLC4A2) had a significant effect (FIG. 1B). It partially decreased iodide influx under both isotonic and hypotonic conditions.

Our genome-wide screen used three independent, separately transfected siRNAs per gene and was performed in duplicate. Each 384-well plate contained cells transfected with siRNAs targeting YFP or leading to cell death as transfection controls and cells treated with siRNAs against AE2 as assay-specific control (see supplementary materials and methods, and FIG. 8). We followed the fluorescence of each well over ~500 seconds after adding the iodide-containing hypotonic solution. Offline data analysis included background subtraction and normalization. It yielded various parameters (see supplementary materials and methods, and FIGS. 9, A and B), including the maximal slope of fluorescence quenching that was our primary criterion to define hits rather than final steady-state fluorescence as used by others (Stotz et al.). This slope, which is related to the rate of iodide influx, was normalized to the average slope of fluorescence decrease and expressed in terms of standard deviations from the mean (Z-score). We prioritized the genes according to the mean Z-score for those two siRNAs that gave the largest value. Further criteria included the number of predicted transmembrane domains (at least one) and a wide tissue expression pattern. Well established protein functions that may exclude a role in VRAC served as negative criteria. Based on these criteria, 87 genes (table S2) were taken into a secondary screen with pools of four siRNAs distinct from those used in the primary screen. Among these genes, only suppression of LRRC8A robustly slowed hypotonicity-induced YFP quenching (FIG. 1C). To ascertain that LRRC8A siRNA reduced VRAC currents rather than affecting other iodide transport proteins, we measured $I_{Cl(swell)}$ of HEK cells transfected with siRNA pools against either LRRC8A or unrelated control genes. Indeed, knock-down of LRRC8A strongly suppressed $I_{Cl(swell)}$ (FIGS. 1, D to F), suggesting that the multispan membrane protein LRRC8A is an indispensable component of VRAC itself or a crucial factor needed for its activation.

To test whether LRRC8A is sufficient to form VRAC we transfected a full-length LRRC8A cDNA into HEK cells and measured $I_{Cl(swell)}$ after 1-3 days. Although it reached the plasma membrane (FIG. 2A for HeLa cells), transfected LRRC8A did not increase, but rather specifically decreased $I_{Cl(swell)}$ (FIG. 1F). We therefore hypothesized that VRAC contains LRRC8A as part of a heteromeric complex and that LRRC8A overexpression led to a subunit stoichiometry that was incompatible with channel activity.

$I_{Cl(swell)}$ Requires Combinations of LRRC8 Isoforms

LRRC8A has four closely related homologs (LRRC8B-LRRC8E), all of which share the same topology of four putative transmembrane domains (Kubota et al, Abascal et al). EST databases suggested that all homologs were expressed in a wide range of tissues. We therefore suspected that VRAC is formed by LRRC8 heteromers and co-expressed LRRC8A with other LRRC8 proteins in mammalian cells. Immunocytochemistry of transfected HeLa cells and of native HEK cells showed that LRRC8A was present at the plasma membrane (FIGS. 2, A to C). This localization depended on the LRRC8A carboxy-terminus since a truncated mutant was retained in the cytoplasm (FIG. 2D). Unlike LRRC8A, LRRC8B through LRRC8E resided in intracellular, ER-like compartments when transfected alone (FIGS. 2, E to H). Upon coexpression with LRRC8A, however, these isoforms were detected at the plasma membrane (FIGS. 2, I to L), suggesting that they are trafficked there in a complex with LRRC8A. Unlike transfection with LRRC8A, co-expression of LRRC8A with LRRC8C did not suppress native $I_{Cl(swell)}$ in HEK cells (FIG. 1F), suggesting that LRRC8 heteromers may mediate $I_{Cl(swell)}$. However, neither this co-expression, nor any other combination tested, significantly increased current amplitudes above WT levels.

To avoid problems associated with the only partial knockdown of target proteins by siRNA we used the zinc-finger nuclease and CRISPR/Cas (Cong et al.) technologies to constitutively disrupt LRRC8 genes in cell culture. Besides polyploid HEK cells we mainly used the stably diploid human HCT116 cell line to increase the efficiency of disruption. To exclude off-target effects, we generated two different HEK and three different HCT116 LRRC8A$^{-/-}$ cell lines in which the LRRC8A gene was disrupted at different positions with different constructs (tables S3 and S4). Gene disruption was confirmed by DNA sequencing and Western blots (FIGS. 3, A and B and FIG. 10A). $I_{Cl(swell)}$ was abolished in all five cell lines and could be rescued by LRRC8A transfection (FIGS. 3, C and E, and FIG. 10B), proving that LRRC8A is essential for ICl(swell). We also produced several HCT116 cell lines in which other LRRC8 genes were disrupted singly or in several combinations, including a line in which all five LRRC8 genes were disrupted (henceforth called LRRC8$^{-/-}$ cells). With the exception of LRRC8A, disruption of single LRRC8 genes did not abolish VRAC currents (FIGS. 3, D and E). However, $I_{Cl(swell)}$ amplitudes were reduced by >50% in LRRC8E$^{-/-}$ and by >80% in LRRC8C$^{-/-}$/LRRC8E$^{-/-}$ and LRRC8C$^{-/-}$/LRRC8D$^{-/-}$/LRRC8E$^{-/-}$ double and triple knock-out (KO) cells, respectively and was abolished in cells lacking functional LRRC8B through E (FIGS. 3, D and E). Strikingly, $I_{Cl(swell)}$ inactivated faster and at less positive potentials in LRRC8C$^{-/-}$ and in LRRC8C$^{-/-}$/LRRC8E$^{-/-}$ double KO cells compared to wild-type (WT) HCT116, LRRC8B$^{-/-}$, LRRC8D$^{-/-}$ or LRRC8E$^{-/-}$ cells (FIGS. 3, D, F and G). By contrast, $I_{Cl(swell)}$ inactivated more slowly and at more positive voltages in LRRC8D$^{-/-}$/LRRC8E$^{-/-}$ HTC116 cells and WT HEK cells (FIGS. 3C, D, F and G).

LRRC8A transfection into the quintuple KO cell line LRRC8$^{-/-}$ failed to rescue $I_{Cl(swell)}$ (FIGS. 3A and B). This result agrees perfectly with the absence of $_{ICl(swell)}$ in cells lacking functional LRRC8B through E (LRRC8(B,C,D,E)$^{-/-}$ cells) (FIGS. 3, D and E). Co-transfecting LRRC8$^{-/-}$ cells with LRRC8A and either LRRC8C or LRRC8E yielded $I_{Cl(swell)}$ with current densities similar to those of native cells (FIG. 4B). Co-expressing LRRC8A with LRRC8D yielded lower currents (FIGS. 4, A and B) and no current was observed upon LRRC8A+B coexpression, a finding that may be related to the fact that both LRRC8B and D were poorly expressible in several cell lines (FIGS. 5, D and F for HEK). The small or undetectable ICl(swell) observed with these combinations fits to the low currents of LRRC8C$^{-/-}$/LRRC8E$^{-/-}$ cells (FIG. 3E) in which LRRC8A can only interact with LRRC8B and/or LRRC8D.

ICl(swell) inactivated more slowly and at more positive voltages when LRRC8A was coexpressed with LRRC8C in LRRC8$^{-/-}$ cells compared to cells co-expressing LRRC8A and LRRC8E or LRRC8A and LRRC8D (FIGS. 4, A, C and D). This observation agreed with the faster $I_{Cl(swell)}$ inactivation in LRRC8C$^{-/-}$ cells (FIGS. 3, D, F and G), suggesting that in those cells the missing 'decelerating' LRRC8C subunit was replaced by LRRC8E or other 'accelerating' subunits. These effects on intrinsic channel properties strongly suggested that LRRC8 proteins are integral parts of VRAC rather than purely regulatory proteins in the signaling cascade leading to channel opening.

Depending on the cell type, native $I_{Cl(swell)}$ currents display different inactivation kinetics (3). Whereas $I_{Cl(swell)}$ shows prominent inactivation at positive potentials in many epithelial cells, HEK cells (30, 31) (FIG. 1E, and FIGS. 3, C, F and G) and more pronounced in HCT116 cells (FIGS. 3, D, F and G), it inactivates much less in lymphocytes, neutrophils and promyelocytic HL-60 cells (Hernandez-Carballo et al., Perez-Cornejo et al.), vascular smooth muscle cells (Wang et al.) and neurons (Leaney et al.). Additional data on characterisation of $I_{Cl(swell)}$ is provided in FIG. 12.

NCBI EST databases suggest that blood cells, vasculature and nervous tissue express the 'decelerating' subunit LRRC8C, but lack LRRC8E that most potently induces inactivation (FIGS. 4, A, C and D). Quantitative RT-PCR confirmed that HEK and HCT116 cells express LRRC8A through LRRC8E, whereas the 'accelerating' isoform LRRC8E was almost absent from HL-60 cells (FIG. 4E). Moreover, HCT116 cells, whose ICl(swell) inactivates faster and at more negative voltages than in HEK cells (FIGS. 3, C, D, F and G), express much less 'decelerating' LRRC8C than HEK (FIG. 4E). Hence, differences in VRAC inactivation among native cells may be explained by tissue-specific expression patterns of LRRC8 isoforms.

Topology of LRRC8 Proteins and Assembly to Heteromers

LRRC8 proteins have four predicted transmembrane domains (TMDs) followed by rather long hydrophilic C-termini that contain up to 17 leucine-rich repeats (Smits et al.) (hence their abbreviation LRRC8=leucine-rich repeat containing 8) (FIG. 5A). Their C-termini were originally thought to be extracellular (Kubota et al., Sawada et al.) where their leucine-rich repeats might interact with other proteins (Kobe et al.), but an analysis (Abascal et al.) of glycosylated or phosphorylated peptides deposited in proteome databases indicated that LRRC8 N- and C-termini are cytoplasmic (FIG. 5A). This work (Abascal et al.) also detected a weak homology to pannexins (Penuela et al.), a family of pore-forming proteins with four TMDs which display the same topology as connexins. Connexins form hexameric hemichannels that bind to similar hexamers on adjacent cells to form gap junctions (Maeda et al.). This similarity led to the proposal (Abascal et al.) that LRRC8 proteins also assemble to hexamers and form channels for so far unknown substrates. LRRC8 proteins are found in vertebrates and other chordates, but not in other phyla like arthropoda (Abascal et al.). This observation fits to the expression pattern of VRAC currents, which were found in many vertebrate species (Nilius et al. 1994), but not in insect cells whose volume-activated Cl$^-$ currents have different properties and are mediated by bestrophins (Stotz et al., Chien et al.).

We used two approaches to ascertain the transmembrane topology of LRRC8A. Mutational inactivation of consensus sites for N-linked glycosylation in the loop between TMD1 and TMD2 decreased the apparent molecular weight of heterologously expressed LRRC8A (FIG. 5B), demonstrating that this loop faces the ER lumen during biogenesis.

Moreover, constructs in which HA-epitopes were inserted either into the loop between TMD3 and TMD4 of LRRC8A, or attached to its C-terminus, were expressed in HeLa cells. Comparative immunofluorescence of non-permeabilized and permeabilized transfected cells placed the TMD3-4 segment to the extracellular side and the C-terminus into the cytoplasm (FIG. 5C). Thus LRRC8 proteins indeed resemble pannexins and connexins in their transmembrane topology.

The formation of LRRC8 heteromers, as indicated by our immunocytochemical (FIG. 2) and electrophysiological analysis (FIG. 4) of co-transfected cells, was confirmed by co-immunoprecipitation from HEK cells transfected with LRRC8A and epitope-tagged versions of either LRRC8B, C, D, or E. LRRC8A precipitation brought down each of the other isoforms, but not the Cl⁻ channel ClC-1 used as control (FIGS. 5, D and E). Conversely, precipitation of epitope-tagged versions of LRRC8B through LRRC8E brought down LRRC8A (FIG. 5F). LRRC8A also co-precipitated LRRC8E from WT HEK cell lysate (FIG. 5G).

LRRC8 Complex Formation in the Absence of LRRC8A

Although LRRC8A appears to be required for $I_{Cl(swell)}$, other LRRC8 proteins do form protein complexes independently of LRRC8A, indicating that VRAC function, either under different conditions or in different membrane compartments, may in fact be present without LRRC8A. As shown in FIG. 13, tagged versions of LRRC8 proteins LRRC8C and LRRC8E expressed in LRRC8A-deficient cells physically interact, when assayed by co-immunoprecipitation with antibodies directed against the respective tags.

LRRC8-Dependent Taurine Flux Suggests that VRAC is VSOAC

The identification of LRRC8A as essential VRAC subunit now allowed us to rigorously test the controversial (Lambert et al., Shennan et al., Stutzin et al.) contention that VRAC also serves as a conduit for the organic osmolyte taurine (6). Swelling-induced taurine efflux was determined with HEK and HCT116 cells and the respective LRRC8A⁻/⁻ cell lines. Exposure to hypotonic saline induced a robust efflux of taurine in both parent cell lines, but not in their LRRC8A⁻/⁻ derivates (FIGS. 6, A and B). Swelling-induced taurine efflux was also abolished in LRRC8(B/C/D/E)⁻/⁻ HCT116 cells in which LRRC8A was the only LRRC8 gene remaining intact (FIG. 6C). FIG. 6D also demonstrates taurine efflux, in particular partial rescue after transfection with LRRC8A and -C. Hence, both $I_{Cl(swell)}$ and swelling-induced taurine efflux depended on LRRC8 heteromers, with LRRC8A being an essential constituent. These results strongly suggested that VRAC is identical to VSOAC, the postulated volume-stimulated organic osmolyte/anion channel (Strange et al.).

Discussion of the Examples

The identification of LRRC8 proteins as crucial VRAC constituents ends a two-decade long hunt for the elusive molecular identity of this important channel. The absence of $I_{Cl(swell)}$ upon genomic disruption of LRRC8A and its rescue by transfection of the corresponding cDNA identified LRRC8A as an indispensable component of VRAC or alternatively as being crucial for its activation. The wide expression pattern of LRRC8 genes and the plasma membrane residency of LRRC8A-containing heteromers are fulfilled prerequisites for LRRC8 proteins forming the channel. The dependence of current inactivation kinetics on the combination of LRRC8 isoforms strongly indicated that LRRC8 heteromers are integral components of VRAC itself, a notion further supported by the homology of LRRC8 proteins to pannexins. The fact that co-transfection of LRRC8 isoforms failed to significantly increase $I_{Cl(swell)}$ amplitude over WT levels indicated that other, still unknown factors limit VRAC activity. Such a limiting component could be part of the signal transduction machinery involved in channel activation or might be an auxiliary subunit of VRAC itself. In this respect, it is interesting to note that VRAC currents seem to be highly regulated. ICl(swell) amplitudes differ only by a factor of 2-3 across many different cell types (Nilius et al. 1997, Nilius et al. 1994). The invention therefore provides the basis for identifying associated proteins, for identifying potential VRAC modulators and for elucidating the signal transduction cascade leading to VRAC opening.

The homology between LRRC8 proteins and pannexins led to the proposal that LRRC8 proteins form hexameric channels (Abascal et al.). We experimentally confirmed the pannexin-like topology of LRRC8A and indicate that the VRAC pore is formed by LRRC8 hexamers that contain LRRC8A and minimally one other family member. While the stoichiometry and permissible subunit compositions remain to be determined, we showed that the obligatory LRRC8A subunit can physically interact with all other four LRRC8 isoforms. LRRC8A supported $I_{Cl(swell)}$ in combination with either LRRC8C, LRRC8D, or LRRC8E. Small, but significant $I_{Cl(swell)}$ of cells lacking functional LRRC8C, D, and E demonstrated that also LRRC8B can form channels with LRRC8A. Assuming a hexameric assembly and depending on oligomerization efficiencies and tissue expression patterns, VRAC may contain one to five different LRRC8 isoforms. Potentially this can give rise to a very large variety of VRAC channels that may differ in various aspects including current inactivation as shown here. The inactivation kinetics of VRAC varies between different tissues and cells (3), a finding that can now be ascribed to different expression ratios of different LRRC8 isoforms.

LRRC8A was indispensable for swelling induced transport of both halides and the organic osmolyte taurine, a zwitterion that is in part negatively charged at physiological pH. Experiments on cells with disrupted LRRC8B through LRRC8E revealed that taurine and chloride flux similarly depended on LRRC8 heteromers.

Although LRRC8A was indispensable for swelling induced transport in the assay disclosed herein, further experimentation has demonstrated that LRRC8 heteromeric protein complexes do exist in cells without LRRC8A. This indicates that VRAC alternatives, with distribution in alternative cell types or membrane compartments other than those assessed directly, do exist. The immunoprecipitation data for LRRC8 heteromeric protein complexes without LRRC8A provides support for such complexes and enable utilisation of such complexes in the test system described herein.

The seemingly promiscuous interactions of LRRC8 isoforms allows for the possibility that the ratio of Cl⁻ to taurine flux may depend on the isoform composition of the channel and we cannot exclude that different accessory subunits influence their substrate specificity. Our data also indicate that swelling-induced glutamate release, which was invoked in VSOAC-mediated neurotoxicity in stroke (4), may be mediated by LRRC8-containing channels. Finally, the permeation of both Cl⁻ and taurine fits to the notion that the VRAC/VSOAC pore is formed by LRRC8 hexamers since hexameric pannexin channels also display rather poor substrate specificity (Penuela et al.). Further data now demonstrates that a large number of different molecule types may be transported through the LRRC8 channel complex described herein. Essentially any ion or organic substance could potentially be transported, as recent reports have also disclosed the transport of antibiotic compounds in addition to organic compounds such as taurine.

Abnormal forms or deleted versions of LRRC8 family members are potentially pathologic. A patient with a chromosome translocation that truncated the LRRC8A protein within the cytoplasmic leucine-rich repeat region displayed agammaglobulinemia and facial abnormalities (Sawada et al.). This observation and experiments in which mutant LRRC8A was transfected into bone marrow cells suggested that LRRC8A is important for B-cell development (Sawada et al.). Our experiments now showed that a similarly truncated LRRC8A protein was non-functional (FIG. 2D). LRRC8C was previously identified as a factor of adipocyte differentiation, hence its alternative name fad158 (Tominaga et al.). LRRC8C knock-down impaired differentiation of 3T3-L1 cells into adipocytes (Tominaga et al.), whereas LRRC8C$^{-/-}$ mice displayed subtle changes in insulin resistance and body fat under high fat diet (Hayashi et al.). The identification of potential VRAC modulators therefore could play an important role in developing new treatments for such conditions.

Our identification of LRRC8 heteromers as an integral part of VRAC/VSOAC provides the basis to explore the structure-function relationship of this important channel, to clarify the hitherto enigmatic signal transduction from cell volume increase to channel opening, to identify potential modulators of the channel and to investigate the role of the channel in basic cellular processes like cell division, growth, and migration. It also allows a rigorous assessment of the various physiological and pathological roles that have been ascribed to VRAC/VSOAC and will facilitate the development of specific inhibitors or openers that may be beneficial for several pathological conditions.

Materials and Methods Used in the Examples:
HEK293-YFP Cell Line Used in the siRNA Screen The T-REx® system (Life Technologies) was used to generate a stable HEK293 cell line inducibly expressing the halide-sensitive YFP(H148Q/I152L) (Galietta et al.). Clones were selected using 200 µg/ml hygromycin B and 10 µg/ml blasticidin. Monoclonal cell lines were subsequently tested for robust and homogenous expression of YFP after induction with 1.25 µg/ml doxycycline using life-cell imaging. The clone 1:5—(Jackson et al.) was chosen for the genome-wide screening procedure. The cells were kept in DMEM with tetracycline-free Hyclone FCS (Thermo Scientific) and the above-mentioned antibiotics.

Genome-Wide siRNA Screen

The screen was performed at the FMP Screening Unit using the Ambion Silencer® Human Genome siRNA Library V3 (Life Technologies) containing 189 384-well plates. This library targets each gene by three independently placed siRNAs. The screen was performed in two replicates. Each screening plate contained several controls like siRNA pools against YFP (Silencer GFP siRNA from Ambion), a non-targeting siRNA (Silencer Negative Control from Ambion), an siRNA pool against AE2 (ON-TARGETplus SMARTpool siRNA SLC4A2 from Thermo Scientific) and a cell death-inducing siRNA mixture (AllStars Hs Cell Death Control siRNA from Qiagen). For detailed plate layout see FIG. 8. For siRNA transfection, in each well of the 384-well assay-plate 8 µl of a 500 nM library-siRNA-OptiMEM® solution was mixed with 0.2 µl Lipofectamine® RNAimax transfection reagent (Life Technologies) previously diluted in 11.8 µl Opti-MEM® (Life Technologies). Subsequently 6000 cells/well in antibioticfree DMEM were seeded onto the pre-dispensed transfection mixture using a BioTek EL406™ dispenser resulting in a final concentration of 50 nM siRNA in a total volume of 80 µl per well. After 24 h the cell culture medium was exchanged to phenol red-free DMEM containing 1.25 µg/ml doxycycline to induce YFP-expression.

The YFP-quenching assay was performed 72 h post-transfection. After having exchanged the cell culture medium in all wells of the plate with 10 µl of isotonic solution (in mM: 145 NaCl, 5 KCl, 1 MgCl2, 2 CaCl2, 10 glucose, 10 HEPES pH 7.4, 329 mOsm) in a Tecan Freedom EVO 200 workstation, the plates were transferred into the FLIPR™ (Molecular Devices) High Throughput Cellular Screening Device and fluorescence measurements were initiated. All wells of the plate were simultaneously illuminated at λ=495-505 nm and YFP-fluorescence was measured at λ=526-585 nm using the FLIPR Fluo3 LED/filter set. After 5 measurements in intervals of 5 s, parallel pipetting within the FLIPR™ added 25 µl iodide-containing hypotonic (rows 1-23) (in mM: 70 NaI, 5 NaCl, 5 KCl; 1 MgCl2, 2 CaCl2, 10 glucose, 10 HEPES pH 7.4, 189 mOsm) or isotonic (row 24) (in mM: 70 NaI, 5 NaCl, 5 KCl; 1 MgCl2, 2 CaCl2, 10 glucose, 140 mannitol, 10 HEPES pH 7.4, 329 mOsm) solution into each well. The solution added to wells 023, P23, O24 and P24 was hypotonic and contained 1% Triton X100. The mixture of the pre-existing 10 µl isotonic solution and the newly added 25 µl hypotonic solution resulted in a final osmolarity of 229 mOsm, i.e. a ~30% decrease in osmolarity, and a final concentration of 50 mM iodide. Fluorescence measurements were continued for 55 s in 5-s intervals, followed by 8 measurements in 30-s intervals to minimize bleaching, and finally 10 measurements in 1-s intervals. The total amount of measurement (500 s) was sufficient for YFP-quenching to nearly reach steady state. At time points 0 s and 5 s (before pipetting) and at 25, 30, 35, 40, 45, and 490 s (during/after pipetting) photographs of the entire plate were taken to allow post-hoc control of the integrity of the cell layers of each well. All original fluorescence traces were stored for reanalysis.

Parameters Extracted from FLIPR™ Screen and Bioinformatics Analysis

Several parameters were extracted from the primary data and used for subsequent data evaluation (FIGS. 9, A and B). The averaged fluorescence before the pipetting step, $F^{abs}_{ante}$, was obtained by averaging values from measurements 1-3 and was used to set a warning low cell' flag when its value was less than 0.8 times of mean $F^{abs}_{ante}$ averaged over all experimental wells from the plate. After pipetting, the fluorescence acutely changed to new values that were more or less stable for about 30 s before swelling-induced quenching of YFP set in. We averaged fluorescence values from measurements 9 to 12 to obtain $F^{abs}_{start}$ which was subsequently used for normalization. $F^{abs}_{fin}$ was defined as averaged fluorescence from the four last measurements and we set another warning flag if fluorescence had not reached quasi-steady-state at the end of the measurement. $F^{abs}_{fin}$ might be used for background subtraction. We preferred, however, to subtract FBG TX100, the averaged (over the last 300 s) fluorescence of the four control wells from the same plate that had been exposed to Triton X100 to maximally quench YFP fluorescence. The background-subtracted fluorescence value of each well was then normalized to the corresponding $F^{abs}_{start}$ value to yield F* (FIG. 9B).

siRNA-mediated knock-down of VRAC should reduce iodide current magnitude, but not necessarily the final intracellular iodide concentration (reflected in $F^{abs}_{fin}$). Although not being a linear function of iodide influx, the speed of YFP quenching after exposure to hypotonicity is the best indicator for the magnitude of VRAC currents. We therefore determined the slope of fluorescence change by linear regression of 11 points in a sliding window between 35 and 350 s. The maximum of these slopes was defined as $S_{max}$. The intersection of the corresponding linear regression line with $F^*=1$ defined $t_{onset}$ as a measure for the speed of response to the hypotonic challenge, a delay that might be changed e.g. by interfering with the signal transduction cascade leading to VRAC opening (FIG. 9B). For each individual plate we then calculated the mean maximal slope $S_{maxmean}$ of all experimental wells and the corresponding standard deviation. $S_{max}$ of each individual siRNA-treated well was expressed in terms of standard deviations to yield Z-scores, with e.g. Z=2 meaning that the slope is slower by two standard deviations compared to the average of the plate.

siRNAs leading to cell death or targeting YFP confirmed that results of none of our 384-well plates had to be discarded because of low transfection efficiency. Results were sorted by genes and listed individually for each of the three siRNAs (which generally were on different plates) the Z-score, $t_{onset}$, $F^{abs}_{ante}$, $F^{abs}_{fin}$, the low-cell and the non-steady-state flags (1 or 0). It also listed the protein families associated with the gene products (as obtained from UniProtKB database (Magrane et al.)), the genes' tissue expression pattern (as determined by publicly available microarray data (Lopes et al.)) and predicted number of transmembrane domains that was calculated by the software TMHMM 2.0c (Krogh et al.). Comparison of the first and replicate screen showed that the effects of individual siRNAs on the respective Z-scores of $S_{max}$ correlated reasonably well and demonstrated the usefulness of our warning flags (FIGS. 9, C and D). To account for different efficiencies of siRNA knockdown with the three individual siRNAs against each gene, some of which may be ineffective or show off-target effects, we sorted our results according to the mean Z obtained with the two 'best' siRNAs (giving the largest values of Z).

As expected, many of the hits could be ruled out by one or more criteria. For instance, siRNAs against several ribosomal proteins led to large Z-scores that were caused by poor cell growth or cell death as indicated by the 'low cell' flag. Large Z-scores that were not reproduced in the replicate screen could sometimes be eliminated by examining the photographs of the plates which showed dirt at the respective well that had caused high background fluorescence. As we were looking for the channel itself and not for proteins involved in the activation of VRAC, we limited our search to proteins having at least one predicted transmembrane domain. Many candidates could be eliminated by their well established function or their inclusion in well-known gene families like olfactory receptors or other G-protein coupled receptors. However, as annotations are not always reliable and as proteins may serve more than one function, several candidates whose annotated function appeared to be incompatible with VRAC function but which otherwise seemed promising were earmarked for a secondary screen. As VRAC currents have been observed in every mammalian tissue that has been investigated, we excluded candidates that showed a narrow tissue distribution or very low expression levels as indicated by NCBI EST profile databases or the scientific literature, except when they belonged to a gene family whose overlapping expression pattern covered many tissues.

On the basis of these criteria 87 candidate genes (table S2) were selected for a secondary screen that used again the FLIPR™ assay with pools of four siRNAs (ONTARGET-plus SMARTpool siRNA, Thermo Scientific) that were different from the ones used in the primary screen. Of these genes, only LRRC8A passed the test. The SMART pool directed against LRRC8A slowed hypotonicity-induced quenching of YFP fluorescence better than the SMART-pool against AE2 (FIG. 1C). It is interesting to note that LRRC8A was at the $222^{nd}$ position of hits sorted exclusively by the mean Z-score averaged across both screens from the 2 out of 3 siRNAs per gene that gave the best score. Only one of the three siRNAs against LRRC8A gave a Z-score for maximal slope of ~2, the two others were below 1 (FIG. 9E).

Generation of Monoclonal Knock-Out Cell Lines Using the CRISPR/Cas and Zinc-Finger Nuclease Technologies For the disruption of LRRC8 genes by the CRISPR/Cas system in cell culture, we used the px330 single plasmid system as described (Cong et al). The targeting sgRNA sequences were chosen using both the UCSC Genome Browser tool at www.genome-engineering.org and the sequence collection from (Mali et al) (for sequences, table S3). Target sgRNAs were cloned into the px330 vector and transfected into the described YFP expressing HEK293 clone or WT HCT116 cells in a E-well format using 3 µl of the Fugene HD transfection reagent and 900 ng targeting vector(s) (up to 4) plus 100 ng pEGFP-C1-vector. In HCT116 cells, the LRRC8A gene was additionally disrupted using custom-designed CompoZr® Knock-out Zinc-Finger Nucleases (Sigma). The zinc-finger nuclease (ZFN) pair encoded on two separate plasmids was transfected as the CRISPR/Cas constructs described above, using 500 ng of each ZFNplasmid and 100 ng of the pEGFP-C1 vector. 2-5 days post-transfection single GFP-positive cells were FACS-sorted into 96-well plates containing preconditioned DMEM (for HEK cells) or McCoy's 5A (for HCT116 cells) medium. In some cases, transfected cells were enriched by G418 selection before FACS sorting.

Monoclonal cell lines were raised and tested for sequence alterations using target-sitespecific PCR on genomic DNA followed by Sanger-sequencing and/or Western blot analysis to confirm the absence of the protein when specific antibodies were available. To generate multiple KOs of several genes, the respective plasmids were transfected together, or cell lines already carrying LRRC8 gene disruptions were targeted again for other LRRC8 genes.

Antibodies

Polyclonal antibodies were raised in rabbits against the peptide QRTKSRIEQGIVDRSE (SEQ ID NO.: 21) that was coupled to KLH through an N-terminally added cysteine. Its sequence corresponds to LRRC8A protein sequence between TMD2 and TMD3. Sera were affinity-purified against the peptide and proved specific in Western blots (FIG. 3B and FIG. 11A) and immunofluorescence (FIGS. 2, B and C, and FIGS. 11C, D). The LRRC8E antibody is characterised in FIG. 11B.

The following commercial primary antibodies were used: rabbit anti-myc (A-14, Santa Cruz Biotechnology), rabbit anti-GFP (A-11122, Life Technologies) for IP and chicken antiGFP (1020, Ayes Lab) for Western blot, mouse anti-α-tubulin (DM1A, Sigma), mouse anti-HA (HA.11, Covance). Secondary antibodies were conjugated to AlexaFluor 488 or 546 (Molecular Probes) or to horseradish peroxidase (Jackson ImmunoResearch).

Expression Constructs and Immunocytochemistry

For expression of LRRC8A-E with GFP fused to their N-termini or C-termini, cDNA encoding the respective human protein (or only aa 1-719 for $_{LRRC8Atrunc}$) was cloned with stop codon into pEGFP-C1 or without stop codon into pEGFP-N1, respectively. For expression of C-terminally RFP-tagged LRRC8A, the cDNA was cloned into μm RFP-N1. cDNA encoding human ClC-1 was in pEGFP-C1. For untagged (co-expression in electrophysiological experiments and antibody testing by Western blot) and C-terminally myc-tagged (deglycosylation experiment and co-immunoprecipitations) expression, cDNA encoding LRRC8A was cloned (with and without stop codon, respectively) into pcDNA3.1/myc-His(−)B (Invitrogen). HA-tags at T307 or at the extreme C-terminus of LRRC8A) and point mutations were introduced by PCR. All constructs were confirmed by sequencing the complete ORF.

For immunocytochemistry, cells were transfected (if indicated) with plasmid encoding the respective construct(s) using Fugene HD. 24-36 h after transfection, cells were fixed in pre-cooled methanol at −20° C. for 10 min (immunostaining with LRRC8A antibody), or in 2% (topology assay) or 4% PFA in PBS for 15 min followed by a 5-min incubation with 30 mM glycine in PBS at room temperature. Cells were incubated sequentially for 1 h each with primary and secondary antibodies (where applicable) in PBS containing 0.1% Triton X-100 (or without, for non-permeabilized cells) supplemented with 3% BSA. Images were acquired with an LSM510 confocal microscope with a 63×, 1.4 NA oil-immersion lens (Zeiss).

Quantitative RT-PCR

Total RNA was isolated from cell pellets using the RNeasy Mini Kit (Qiagen). We subjected ~1 μg of RNA to DNase I (amplification grade, Invitrogen) digestion and subsequently transcribed it into cDNA using random primers and Superscript II reverse transcriptase (Invitrogen). A 20 μl qRT-PCR reaction was set up using the Power SYBR Green PCR Master Mix (Applied Biosystems) and 0.5 μM of specific primers. Reactions were run in triplicates with a 60 s elongation time at 60° C. Amplification and melting curves were monitored using a StepOnePlus Real-Time PCR System and StepOne Software (Applied Biosystems). GAPDH was used as internal control and for ΔΔCt calculations. Primers were designed using the QuantPrime selection tool (Arvidsson et al) to preferentially span exon-exon boundaries and give products of 60-150 bp.

The following primer pairs were used (5'-3'):

```
GAPDH:
                                     (SEQ ID NO.: 1)
ACAGTCAGCCGCATCTTCTT
and
                                     (SEQ ID NO.: 2)
GTTAAAAGCAGCCCTGGTGA LRRC8A:
                                     (SEQ ID NO.: 3)
GGGTTGAACCATGATTCCGGTGAC
and
                                     (SEQ ID NO.: 4)
GAAGACGGCAATCATCAGCATGAC LRRC8B:
                                     (SEQ ID NO.: 5)
ACCTGGATGGCCCACAGGTAATAG
and
                                     (SEQ ID NO.: 6)
ATGCTGGTCAACTGGAACCTCTGC LRRC8C:
                                     (SEQ ID NO.: 7)
ACAAGCCATGAGCAGCGAC
and
```

-continued
```
                                     (SEQ ID NO.: 8)
GGAATCATGTTTCTCCGGGC LRRC8D:
                                     (SEQ ID NO.: 9)
ATGGAGGAGTGAAGTCTCCTGTCG
and
                                     (SEQ ID NO.: 10)
CTTCCGCAAGGGTAAACATTCCTG LRRC8E:
                                     (SEQ ID NO.: 11)
ACCGTGGCCATGCTCATGATTG
and
                                     (SEQ ID NO.: 12)
ATCTTGTCCTGTGTCACCTGGAG.
```

Electrophysiology

HEK or HCT cells were plated onto gelatine-coated coverslips and transfected using Fugene HD (Promega) or Lipofectamine 2000 (Life Technologies) transfection reagents, respectively. One of the transfected LRRC8 isoforms was fused C-terminally to GFP. When LRRC8A was co-transfected with other LRRC8 isoforms only the latter carried GFP because plasma membrane fluorescence indicated co-expression with LRRC8A.

Whole-cell voltage-clamp experiments were performed in isotonic extracellular solution containing (in mM) 150 NaCl, 6 KCl, 1 MgCl2, 1.5 CaCl2, 10 glucose, and 10 HEPES, pH 7.4 with NaOH (320 mOsm). $I_{Cl(swell)}$ was elicited by perfusing the cells with hypotonic solution containing (in mM) 105 NaCl, 6 CsCl, 1 MgCl2, 1.5 CaCl2, 10 glucose, 10 HEPES, pH 7.4 with NaOH (240 mOsm). The pipette solution contained (in mM) 40 CsCl, 100 CsMeS, 1 MgCl2, 1.9 CaCl2, 5 EGTA, 4 Na2ATP, and 10 HEPES, pH 7.2 with CsOH (290 mOsm). Osmolarities of all solutions were assessed with an Osmomat 030 freezing point osmometer (Gonotec). All experiments were performed at constant temperature of 20-22° C. Currents were recorded with an EPC-10 USB patch-clamp amplifier and PatchMaster software (HEKA Elektronik) or a MultiClamp 700B patch-clamp amplifier/Digidata 1440A digitizer and pClamp 10 software (Molecular Devices). Patch pipettes had a resistance of 1-3 MΩ. Series resistance was compensated by 80-90% to minimize voltage errors. Currents were sampled at 5 kHz and low-pass filtered at 10 kHz. The holding potential was −30 mV. Cells with a membrane resistance below 800 MΩ or series resistance above 10 MΩ were discarded. The standard protocol for measuring the time course of $I_{Cl(swell)}$ activation, applied every 15 s after membrane rupture, consisted of a 0.6 s step to −80 mV followed by a 2.6 s ramp from −100 to 100 mV. The read-out for $I_{Cl(swell)}$ was the steady-state whole-cell current at −80 mV normalized to the cell capacitance (current density) subtracted by the baseline current density at −80 mV before perfusion with hypotonic solution. The voltage protocol, applied after complete activation of $I_{Cl(swell)}$, consisted of 1-s or 2-s steps starting from −120 mV to 120 mV in 20 mV intervals preceded and followed by a 0.5-s step to −80 mV every 5 s.

The inactivation kinetics of $I_{Cl(swell)}$ could not be fitted appropriately by a single-exponential function. We therefore calculated the fraction of remaining current by dividing the current amplitude at the end of the 2-s voltage step by the current amplitude 1.5 ms after the beginning of the voltage step (avoiding contamination by capacitive transients). The half inactivation time $t_{1/2}$ was determined by the time point where the inactivation reached half of the total inactivation after 2 s. Calculation of current densities and inactivation characteristics was done with an automatic script written in MATLAB R2011a (MathWorks) and plotted with Graph Pad Prism 5 (Graph Pad Software). Boltzmann curve-fitting and calculation of $\tau_{1/2}$ was done with Graph Pad Prism with the following fitting constraints: bottom value less than 0.2, top value greater than 0.9. Example current traces were lowpass-filtered at 2 kHz and reduced to a sampling rate of 1 kHz for clarity. Averaged data is presented as mean±SEM. Significance was calculated by one-way ANOVA and Tukey's post-hoc test, where applicable. At least 4 cells per condition were measured on at least two different days; exact n-values are given in the figures. Where possible, measurements were done blinded.

Deglycosylation, Co-Immunoprecipitation and Western Blot

To assess glycosylation of LRRC8A, HEK cells were transfected on 10-cm dishes using 17 µl of polyethylenimine (PEI) and 6 µg of plasmid encoding myc-tagged LRRC8A (wild-type or mutant). Cells were lysed in Ripa lysis buffer (150 mM NaCl, 1% NP-40, 0.5% sodium deoxycholate, 0.1% SDS, 50 mM Tris, pH 8.0, 4 mM Complete Proteinase Inhibitor (Roche), 4 mM Pefabloc (Roth)). After 10 min centrifugation at 14.000 rpm at 4° C., protein concentrations of cell lysates were determined by BCA assay. 60 µg of total protein were mixed with 2 µl of denaturing buffer (NEB) and 2 µl of 0.1 M Tris/HCl pH 7.4 in a reaction volume of 20 µl and denatured at 75° C. for 10 min. Then 4 µl of 10×G7 Buffer (NEB), 4 µl of 10% NP-40 (NEB) and 4 µl of PNGase F (Roche) were added in a total volume of 40 µl. After 2 h incubation at 37° C., the reaction was terminated by adding 10 µl 5×Lämmli sample buffer. Samples were separated by SDS-PAGE and analyzed by Western blot using the LRRC8A antibody. The experiment was repeated 3 times.

For co-immunoprecipitation, HEK cells were co-transfected with plasmids (6 µg total) encoding myc-tagged or untagged LRRC8A and N-terminal fusion constructs of LRRC8A-E or ClC-1 (or soluble GFP) on 10 cm dishes using PEI as described above. 48 h posttransfection cells were lysed in 300 µl lysis buffer (150 mM NaCl, 1% NP-40, 0.5% sodium deoxycholate, 50 mM Tris-HCl pH 7.5, 4 mM Complete Proteinase Inhibitor (Roche), 4 mM Pefabloc (Roth)) for 10 min on ice. The lysate was pre-cleared by centrifugation at 14.000 rpm for 10 min at 4° C. and subsequently spun at 30.000 g for 30 min at 4° C. 150 µl of the supernatant were mixed with 10 µg of the respective antibody and IP buffer (150 mM NaCl, 0.1% NP-40; 0.05% sodium deoxycholate, 50 mM Tris-HCl, pH 7.5, 4 mM Complete Proteinase Inhibitor (Roche)) was added to final volume of 800 µl. The sample was rotated for 1-2 h at 4° C. before 10 µl of Protein A Dynabeads® (Life Technologies) were added and rotation continued overnight at 4° C. After four washes with 500 µl IP buffer, precipitates were eluted in 40 µl Lämmli sample buffer, separated by SDS-PAGE and analyzed by Western blot as indicated. Experiments were repeated 3 times.

To assess protein expression cells were lysed as described above. Protein concentrations were determined by BCA and equal amounts were separated by SDS-PAGE and analyzed by Western blot as indicated.

Taurine Efflux Experiments

HEK or HCT116 cells were grown to ~80% confluency (48-72 h after plating) in 35-mm diameter plates coated with poly-L-lysine. Cells were loaded with $^3$[H]-taurine (2 µCi/ml; Perkin-Elmer) for 2-2.5 h in culture medium (without FCS) at 37° C. They were then washed 7 times at room temperature with isotonic solution (in mM: 150 NaCl, 6 KCl, 1 MgCl2, 1.5 CaCl2, 10 glucose, 10 HEPES pH 7.4, 320 mOsm). After washing, external media were removed in 5-min intervals and replaced with fresh isotonic or hypotonic solution (in mM: 105 NaCl, 6 KCl, 1 MgCl2, 1.5 CaCl2, 10 glucose, 10 HEPES pH 7.4, 240 mOsm) and saved for counting. At the end of the experiment, cells were lysed with 0.75 ml of 0.1 M NaOH. The radioactivity of cell supernatants and of the final cell lysate was determined in a liquid scintillation counter. Values presented were normalized to the total cellular radioactivity at that time point which was determined by adding the counts from the cell lysate and those of the supernatants collected at the corresponding and following time points. In each flux experiment, each data point represents the mean of 6 wells.

Supplementary Tables

TABLE S1

List of anion transporters tested by siRNA interference in HEK cells in a FLIPR ™ prescreen.

| Gene name | Alternative name(s) | Proposed function |
|---|---|---|
| ANO1 | Anoctamin1, TMEM16A | $Ca^{2+}$-activated $Cl^-$ channel |
| ANO3 | Anoctamin3, TMEM16C | $Ca^{2+}$-activated $Cl^-$ channel (?) |
| ANO4 | Anoctamin4, TMEM16D | $Ca^{2+}$-activated $Cl^-$ channel (?) |
| ANO5 | Anoctamin5, TMEM16E | $Ca^{2+}$-activated $Cl^-$ channel (?) |
| ANO6 | Anoctamin6, TMEM16F | $Ca^{2+}$-activated $Cl^-$ or cation channel, scramblase |
| ANO7 | Anoctamin7, TMEM16G | $Ca^{2+}$-activated $Cl^-$ channel (?) |
| ANO8 | Anoctamin8, TMEM16H | $Ca^{2+}$-activated $Cl^-$ channel (?) |
| ANO9 | Anoctamin9, TMEM16J | $Ca^{2+}$-activated $Cl^-$ channel (?) |
| ANO10 | Anoctamin10, TMEM16K | $Ca^{2+}$-activated $Cl^-$ channel (?) |
| CLCN3 | ClC-3 | $Cl^-/H^+$-exchanger, wrongly claimed to be VRAC |
| BEST1 | Bestrophin 1 | $Ca^{2+}$-activated $Cl^-$ channel |
| BEST2 | Bestrophin 2 | $Ca^{2+}$-activated $Cl^-$ channel |
| SLC4A2 | AE2, anion exchanger 2 | $Cl^-/HCO3^-$ exchanger |
| SLC4A3 | AE3, anion exchanger 3 | $Cl^-$/HCO3 - exchanger |
| SLC12A2 | NKCC1 | NaK2Cl cotransporter |
| SLC12A4 | KCC1 | KCl cotransporter |
| SLC12A6 | KCC3 | KCl cotransporter |
| SLC12A7 | KCC4 | KCl cotransporter |
| SLC26A1 | SAT1 | anion exchanger, sulfate transporter |
| SLC26A9 | | anion transporter |
| SLC26A11 | KBAT | $Na^+$-dependent sulfate transporter, $Cl^-$ channel (?) |

TABLE S2

List of candidate genes from genome-wide siRNA screen that were taken into a secondary FLIPR™ RNA interference screen using SMARTpools of independent siRNAs.

|    | Gene ID | Gene symbol    | TMDs* | Z-score† |
|----|---------|----------------|-------|----------|
| 1  | 3371    | TNC            | 1     | 2.6931   |
| 2  | 79652   | TMEM204        | 4     | 2.3119   |
| 3  | 253558  | ALCAT1         | 3     | 2.1069   |
| 4  | 54879   | ST7L           | 2     | 1.9163   |
| 5  | 5793    | PTPRG          | 1     | 1.8685   |
| 6  | 28959   | LR8/TMEM176B   | 4     | 1.8351   |
| 7  | 51234   | EMC4           | 2     | 1.7410   |
| 8  | 10098   | TM4SF9/TSPAN5  | 4     | 1.7358   |
| 9  | 125111  | GJC1/GJD3      | 4     | 1.7326   |
| 10 | 29940   | SART2          | 3     | 1.6643   |
| 11 | 284723  | SLC25A34       | 2     | 1.6399   |
| 12 | 130814  | PQLC3          | 4     | 1.6306   |
| 13 | 23505   | RW1/TMEM131    | 2     | 1.6096   |
| 14 | 199953  | TMEM201        | 6     | 1.5948   |
| 15 | 80759   | KHDC1          | 2     | 1.5846   |
| 16 | 9415    | FADS2          | 4     | 1.5817   |
| 17 | 57484   | RNF150         | 2     | 1.5569   |
| 18 | 54741   | OBRGRP         | 4     | 1.5488   |
| 19 | 5348    | FXYD1          | 1     | 1.5477   |
| 20 | 56172   | ANKH           | 8     | 1.5316   |
| 21 | 4034    | LRCH4          | 1     | 1.5303   |
| 22 | 57198   | ATP8B2         | 9     | 1.5268   |
| 23 | 53346   | TM6SF1         | 9     | 1.5216   |
| 24 | 120224  | TMEM45B        | 5     | 1.5205   |
| 25 | 56262   | LRRC8A         | 4     | 1.5129   |
| 26 | 10959   | RNP24          | 2     | 1.4911   |
| 27 | 79022   | TMEM106C       | 2     | 1.4885   |
| 28 | 349149  | GJE1/GJC3      | 3     | 1.4769   |
| 29 | 746     | TMEM258        | 2     | 1.4751   |
| 30 | 53827   | FXYD5          | 1     | 1.4684   |
| 31 | 55009   | C19orf24       | 2     | 1.4654   |
| 32 | 29058   | C20orf30       | 2     | 1.4566   |
| 33 | 10099   | TM4SF8/TSPAN3  | 4     | 1.4361   |
| 34 | 54929   | TMEM161A       | 8     | 1.4268   |
| 35 | 84561   | SLC12A8        | 10    | 1.4140   |
| 36 | 113829  | SLC35A4        | 9     | 1.4016   |
| 37 | 29956   | LASS2          | 5     | 1.3728   |
| 38 | 145407  | C14orf37       | 2     | 1.3710   |
| 39 | 51522   | TMEM14C        | 4     | 1.3670   |
| 40 | 55739   | FLJ10769       | 1     | 1.3656   |
| 41 | 284099  | C17orf78       | 1     | 1.3551   |
| 42 | 81555   | SMAP-5         | 4     | 1.3487   |
| 43 | 57181   | SLC39A10       | 7     | 1.3480   |
| 44 | 7355    | SLC35A2        | 8     | 1.3401   |
| 45 | 51338   | MS4A4A         | 4     | 1.3255   |
| 46 | 92255   | DKFZp434H2226  | 9     | 1.3153   |
| 47 | 79762   | FLJ14146       | 1     | 1.3139   |
| 48 | 159371  | TMEM20         | 10    | 1.3091   |
| 49 | 79683   | ZDHHC14        | 4     | 1.3016   |
| 50 | 65062   | ALS2CR4        | 4     | 1.2954   |
| 51 | 79844   | ZDHHC11        | 5     | 1.2780   |
| 52 | 10100   | TSPAN-2        | 4     | 1.2743   |
| 53 | 123606  | NIPA1          | 8     | 1.2581   |
| 54 | 55362   | TMEM63B        | 11    | 1.2448   |
| 55 | 124491  | TMEM170A       | 3     | 1.2369   |
| 56 | 56674   | TMEM9B         | 2     | 1.2335   |
| 57 | 94015   | TTYH2          | 6     | 1.2300   |
| 58 | 203562  | TMEM31         | 2     | 1.2116   |
| 59 | 27069   | GHITM          | 6     | 1.2099   |
| 60 | 26526   | TM4-B          | 3     | 1.1928   |
| 61 | 81671   | VMP1           | 6     | 1.1703   |
| 62 | 374882  | TMEM205        | 4     | 1.1329   |
| 63 | 10712   | Fam189B        | 4     | 1.1222   |
| 64 | 85414   | Prostein/SLC45A3 | 11  | 1.1208   |
| 65 | 91147   | TMEM67         | 4     | 1.1122   |
| 66 | 57348   | TTYH1          | 5     | 1.0725   |
| 67 | 128506  | OCSTAMP        | 6     | 1.0707   |
| 68 | 55852   | TEX2           | 2     | 1.0702   |
| 69 | 93109   | TMEM44         | 4     | 1.0630   |
| 70 | 11161   | C14orf1        | 4     | 1.0598   |
| 71 | 64137   | ABCG4          | 7     | 1.0392   |
| 72 | 29097   | HSPC163        | 3     | 1.0315   |
| 73 | 55625   | ZDHHC7         | 4     | 1.0268   |
| 74 | 64429   | ZDHHC6         | 4     | 1.0165   |
| 75 | 54860   | MS4A12         | 4     | 1.0130   |
| 76 | 162427  | FAM134C        | 3     | 1.0120   |
| 77 | 23460   | ABCA6          | 13    | 1.0099   |
| 78 | 9906    | SLC35E2        | 3     | 0.9891   |
| 79 | 64645   | HIAT1          | 12    | 0.9848   |
| 80 | 345274  | SOAT/SLC10A6   | 8     | 0.9758   |
| 81 | 347735  | TDE2L/SERINC2  | 11    | 0.9695   |
| 82 | 55002   | TMCO3          | 10    | 0.9674   |
| 83 | 202915  | TMEM184A       | 7     | 0.9488   |
| 84 | 8082    | SSPN           | 4     | 0.9236   |
| 85 | 84548   | FAM11A/TMEM185A | 8    | 0.9025   |
| 86 | 135656  | DPCR1          | 2     | 0.8911   |
| 87 | 85013   | TMEM128        | 4     | 0.7763   |

*predicted number of transmembrane domains
†mean Z-score for Smax of the two 'best' siRNAs from 2 replicate primary screens

TABLE S3

Guide sequences used for the generation of knock-out cell lines with the CRISPRICas system.

| Target gene | No. | Guide sequence (5'-3')            | Strand | Target location in protein         |
|-------------|-----|-----------------------------------|--------|------------------------------------|
| LRRC8A      | 1A  | ggctgatgtagaaggacgcc agg (SEQ ID NO.: 13) | −      | aa 320-328 (beginning of TMD4)     |
|             | 3A  | tgatgattgccgtcttcggg ggg (SEQ ID NO.: 14) | +      | aa 36-43 (in TMD2)                 |
|             | 4A  | tcctgcaatgattcgttccg ggg (SEQ ID NO.: 15) | +      | aa 64-71 (between TMD1 and TMD2)   |
| LRRC8B      | 1B  | tttttctcttaacgcctcaa agg (SEQ ID NO.: 16) | −      | aa 346-353 (after TMD4)            |
|             | 2B  | ggccacaaaatgctcgagcc tgg (SEQ ID NO.: 17) | −      | aa 147-354 (between TMD2 and TMD3) |

TABLE S3 -continued

Guide sequences used for the generation of
knock-out cell lines with the CRISPR/Cas system.

| Target gene | No. | Guide sequence (5'-3') | Strand | Target location in protein |
|---|---|---|---|---|
| LRRC8C | 1C | atgctcatgatcggcgtgtt tgg (SEQ ID NO.: 18) | + | aa 35-42 (in TMD1) |
| LRRC8D | 1D | gtggctctgagaggtatgtc agg (SEQ ID NO.: 19) | − | aa 107-114 (between TMD1 and TMD2) |
| LRRC8E | 1E | gctggccgagtacctcacc tgg (SEQ ID NO.: 20) | + | aa 27-34 (in TMD1) | aa = amino acid;
TMD = transmembrane domain;
PAM sequences are underlined

TABLE S4

Clonal cell lines with disrupted LRRc8A genes
Table S4. Clonal cell lines with disrupted LRRC8 genes.

| Cell line | Clone name | Construct used | Genetic modification | Protein modification | Used for FIG |
|---|---|---|---|---|---|
| LRRC8A−/− (HEK) | 3E7 | 3A | a1: Δ21nt (t110-a130) | A1: ΔM37-G43 in TMD1 (non-functional) | FIG. 2C; FIGS. 3B, 3C FIG. 6A |
|  |  |  | a2: insertion of 1 nt (t after c123) | A2: G42W-fs in TMD1 | FIG. S4B |
|  | 1F7 | 1A | a1: Δ9nt (a958-g966) | A1: ΔI320-A322 at start of TMD4 (non-functional) | FIG. 3B, FIG. S4B |
|  |  |  | a2: Δ2nt (c964-g965) | A2: A322V-fs at start of TMD4 |  |
|  |  |  | a3: Δ23nt (a958-g980) | A3: I320P-fs at start of TMD4 |  |
| LRRC8A−/− (HCT116) | 3F8 | 3A | Δ2g out of 6g (g124-g129) | G43D-fs in TMD1 | FIGS. 3A, 3B, 3D, 3E FIG. S4B; FIG. S6A |
|  | 4B9 | 4A | a1: Δ32nt (c195-g228) | A1: C65W-fs between TMD1 and TMD2 | FIG. 4B; FIG. 6B FIG. S4B |
|  |  |  | a2: duplication of I206 | A2: R70P-fs between TMD1 and TMD2 |  |
|  | ZF9 | ZFN | a1: Δ2nt (a508-c509) | A1: T170E-fs between TMD2 and TMD3 | FIGS. S4A, S4B |
|  |  |  | a2: Insertion of 5nt (cacga after a511) | A2: R171T-fs between TMD2 and TMD3 |  |
| LRRC8B−/− (HCT116) | n2B-D3 | 2B | duplication of t446 | E150R-fs after TMD2 | FIGS. 3D, 3E, 3F, 3G |
| LRRC8C−/− (HCT116) | n1C-C2 | 1C | duplication of t119 | F41V-fs in TMD1 | FIGS. 3D, 3E, 3F, 3G |
| LRRC8D−/− (HCT116) | n1D-F11 | 1D | a1: Δ19nt (a325-t343) | D1: P110L-fs between TMD1 and TMD2 | FIGS. 3D, 3F, 3G data from both clones pooled for: FIG. 3E |
|  |  |  | a2: duplication of a325 | D2: I109N-fs between TMD1 and TMD2 |  |
|  | n1D-B2 | 1D | duplication of a325 | I109N-fs between TMD1 and TMD2 |  |
| LRRC8E−/− (HCT116) | BCDE (WT)-F5 | 1E | duplication of a94 | T32N-fs in TMD1 | FIG. 3D, data from both clones pooled for: FIGS. 3E, 3F, 3G |
|  | CE(WT)-B6 | 1E | duplication of a94 | T32N-fs in TMD1 |  | a = allele (only given if alleles differed in modifications);
fs = frameshift;
nt = nucleotide;
TMD = transmembrane domain;
ZFN = zinc-finger nuclease;
Δ = deletion Indicated nucleotide numbers give nucleotide position within the ORF.
*Targeting with construct 1B in LRRC8−/− cell line resulted in a duplication of a1043 which would lead to A349G-fs after TMD4. However, the mutations by the 2B targeting (given in table) truncate LRRC8B already after TMD2.

REFERENCES

1. E. K. Hoffmann, I. H. Lambert, S. F. Pedersen, Physiology of cell volume regulation in vertebrates. *Physiol. Rev.* 89, 193 (2009).
2. H. Pasantes-Morales, R. A. Lezama, G. Ramos-Mandujano, K. L. Tuz, Mechanisms of cell volume regulation in hypo-osmolality. *Am. J. Med.* 119, S4 (2006).
3. B. Nilius et al., Properties of volume-regulated anion channels in mammalian cells. *Prog. Biophys. Mol. Biol.* 68, 69 (1997).
4. Y. Okada, K. Sato, T. Numata, Pathophysiology and puzzles of the volume-sensitive outwardly rectifying anion channel. *J. Physiol.* 587, 2141 (2009).
5. Y. Okada, Volume expansion-sensing outward-rectifier Cl-channel: fresh start to the molecular identity and volume sensor. *Am. J. Physiol.* 273, C755 (1997).
6. P. S. Jackson, K. Strange, Volume-sensitive anion channels mediate swelling-activated inositol and taurine efflux. *Am. J. Physiol.* 265, C1489 (1993).
7. S. J. Mulligan, B. A. MacVicar, VRACs CARVe a path for novel mechanisms of communication in the CNS. *Sci. STKE* 2006, pe42 (2006).
8. G. Roy, C. Malo, Activation of amino acid diffusion by a volume increase in cultured kidney (MDCK) cells. *J. Membr. Biol.* 130, 83 (1992).
9. K. Strange, P. S. Jackson, Swelling-activated organic osmolyte efflux: a new role for anion channels. *Kidney Int.* 48, 994 (1995).
10. I. H. Lambert, E. K. Hoffmann, Cell swelling activates separate taurine and chloride channels in Ehrlich mouse ascites tumor cells. *J. Membr. Biol.* 142, 289 (1994).
11. D. B. Shennan, Swelling-induced taurine transport: relationship with chloride channels, anion-exchangers and other swelling-activated transport pathways. *Cell Physiol. Biochem.* 21, 15 (2008).
12. A. Stutzin et al., Separate taurine and chloride efflux pathways activated during regulatory volume decrease. *Am. J. Physiol.* 277, C392 (1999).
13. Y. Okada et al., Volume-sensitive chloride channels involved in apoptotic volume decrease and cell death. *J. Membr. Biol.* 209, 21 (2006).
14. T. Moser, R. H. Chow, E. Neher, Swelling-induced catecholamine secretion recorded from single chromaffin cells. *Pflügers Arch.* 431, 196 (1995).
15. M. A. Valverde et al., Volume-regulated chloride channels associated with the human multidrug-resistance P-glycoprotein. *Nature* 355, 830 (1992).
16. M. Paulmichl et al., New mammalian chloride channel identified by expression cloning. *Nature* 356, 238 (1992).
17. J. Fürst et al., Structure and function of the ion channel ICln. *Cell. Physiol. Biochem.* 10, 329 (2000).
18. W. T. Pu, G. B. Krapivinsky, L. Krapivinsky, D. E. Clapham, plCln inhibits snRNP biogenesis by binding core spliceosomal proteins. *Mol. Cell. Biol.* 19, 4113 (1999).
19. D. Duan, C. Winter, S. Cowley, J. R. Hume, B. Horowitz, Molecular identification of a volume-regulated chloride channel. *Nature* 390, 417 (1997).
20. S. M. Stobrawa et al., Disruption of ClC-3, a chloride channel expressed on synaptic vesicles, leads to a loss of the hippocampus. *Neuron* 29, 185 (2001).
21. T. Voets et al., The chloride current induced by expression of the protein plCln in *Xenopus oocytes* differs from the endogenous volume-sensitive chloride current. *J. Physiol.* 495, 441 (1996).
22. J. J. Wine, D. B. Luckie, Cell-volume regulation: P-glycoprotein—a cautionary tale. *Curr. Biol.* 6, 1410 (1996).
23. M. Tominaga, T. Tominaga, A. Miwa, Y. Okada, Volume-sensitive chloride channel activity does not depend on endogenous P-glycoprotein. *J. Biol. Chem.*—270, 27887 (1995).
24. W. Gong et al., ClC-3-independent, PKC-dependent Activity of Volume-sensitive Cl Channel in Mouse Ventricular Cardiomyocytes. *Cell. Physiol. Biochem.* 14, 213 (2004).
25. S. Gründer, A. Thiemann, M. Pusch, T. J. Jentsch, Regions involved in the opening of ClC-2 chloride channel by voltage and cell volume. *Nature* 360, 759 (1992).
26. H. C. Hartzell, Z. Qu, K. Yu, Q. Xiao, L. T. Chien, Molecular physiology of bestrophins: multifunctional membrane proteins linked to best disease and other retinopathies. *Physiol. Rev.* 88, 639 (2008).
27. S. C. Stotz, D. E. Clapham, Anion-sensitive fluorophore identifies the *Drosophila* swell-activated chloride channel in a genome-wide RNA interference screen. *PLoS ONE* 7, e46865 (2012).
28. L. T. Chien, H. C. Hartzell, Rescue of volume-regulated anion current by bestrophin mutants with altered charge selectivity. *J. Gen. Physiol.* 132, 537 (2008).
29. R. Fischmeister, H. C. Hartzell, Volume sensitivity of the bestrophin family of chloride channels. *J. Physiol.* 562, 477 (Jan. 15, 2005).
30. B. Nilius, J. Prenen, U. Wissenbach, M. Bodding, G. Droogmans, Differential activation of the volume-sensitive cation channel TRP12 (OTRPC4) and volumeregulated anion currents in HEK-293 cells. *Pflügers Arch.* 443, 227 (2001).
31. C. Y. Hernandez-Carballo, J. A. De Santiago-Castillo, T. Rosales-Saavedra, P. Pérez-Cornejo, J. Arreola, Control of volume-sensitive chloride channel inactivation by the coupled action of intracellular chloride and extracellular protons. *Pflügers Arch.* 460, 633 (2010).
32. L. J. Galietta, P. M. Haggie, A. S. Verkman, Green fluorescent protein-based halide indicators with improved chloride and iodide affinities. *FEBS Lett.* 499, 220 (2001).
33. V. Benfenati et al., Carbenoxolone inhibits volume-regulated anion conductance in cultured rat cortical astroglia. *Channels* 3, 323 (2009).
34. N. Decher et al., DCPIB is a novel selective blocker of ICl,swell and prevents swelling-induced shortening of guinea-pig atrial action potential duration. *Br. J. Pharmacol* 134, 1467 (2001).
35. K. Kubota et al., LRRC8 involved in B cell development belongs to a novel family of leucine-rich repeat proteins. *FEBS Lett.* 564, 147 (2004).
36. F. Abascal, R. Zardoya, LRRC8 proteins share a common ancestor with pannexins, and may form hexameric channels involved in cell-cell communication. *Bioessays* 34, 551 (2012).
37. L. Cong et al., Multiplex genome engineering using CRISPR/Cas systems. *Science* 339, 819 (2013).
38. P. Pérez-Cornejo, J. Arreola, F. Y. Law, J. B. Schultz, P. A. Knauf, Volume-sensitive chloride channels do not mediate activation-induced chloride efflux in human neutrophils. *J. Immunol.* 172, 6988 (2004).
39. G. X. Wang et al., Hypotonic activation of volume-sensitive outwardly rectifying chloride channels in cultured PASMCs is modulated by SGK. *Am. J. Physiol.* 287, H533 (2004).
40. J. L. Leaney, S. J. Marsh, D. A. Brown, A swelling-activated chloride current in rat sympathetic neurones. *J. Physiol.* 501, 555 (1997).

41. G. Smits, A. V. Kajava, LRRC8 extracellular domain is composed of 17 leucine-rich repeats. *Mol. Immunol.* 41, 561 (2004).
42. A. Sawada et al., A congenital mutation of the novel gene LRRC8 causes agammaglobulinemia in humans. *J. Clin. Invest.* 112, 1707 (2003).
43. B. Kobe, A. V. Kajava, The leucine-rich repeat as a protein recognition motif. *Curr. Opin. Struct. Biol.* 11, 725 (2001).
44. S. Penuela, R. Gehi, D. W. Laird, The biochemistry and function of pannexin channels. *Biochim. Biophys. Acta* 1828, 15 (2013).
45. S. Maeda et al., Structure of the connexin 26 gap junction channel at 3.5 Å resolution. *Nature* 458, 597 (2009).
46. B. Nilius et al., Volume-activated Cl-currents in different mammalian non-excitable cell types. *Pflügers Arch.* 428, 364 (1994).
47. K. Tominaga et al., The novel gene fad158, having a transmembrane domain and leucine-rich repeat, stimulates adipocyte differentiation. *J. Biol. Chem.* 279, 34840 (2004).
48. T. Hayashi et al., Factor for adipocyte differentiation 158 gene disruption prevents the body weight gain and insulin resistance induced by a high-fat diet. *Biol. Pharm. Bull.* 34, 1257 (2011).
49. M. Magrane, U. Consortium, UniProt Knowledgebase: a hub of integrated protein data. *Database* 2011, bar009 (2011).
50. T. J. Lopes et al., Tissue-specific subnetworks and characteristics of publicly available human protein interaction databases. *Bioinformatics* 27, 2414 (2011).
51. A. Krogh, B. Larsson, G. von Heijne, E. L. Sonnhammer, Predicting transmembrane protein topology with a hidden Markov model: application to complete genomes. *J. Mol. Biol.* 305, 567 (2001).
52. P. Mali et al., RNA-guided human genome engineering via Cas9. *Science* 339, 823 (2013).
53. S. Arvidsson, M. Kwasniewski, D. M. Riano-Pachon, B. Mueller-Roeber, QuantPrime—a flexible tool for reliable high-throughput primer design for quantitative PCR. *BMC Bioinformatics* 9, 465 (2008).

What we claim is:

1. A method for identifying channel modulators comprising:
   providing one or more candidate substances for the channel modulator;
   providing a protein complex comprising one or more LRRC8 proteins (leucine-rich repeat-containing proteins 8) selected from the group consisting of LRRC8A (family member A), LRRC8B (family member B), LRRC8C (family member C), LRRC8D (family member D), and LRRC8E (family member E), wherein said complex is a heterometer and comprises LRRC8A and at least one or more of LRRC8B, LRRC8C, LRRC8D and/or LRRC8E;
   contacting said one or more candidate substances with said protein complex; and
   determining a presence or absence of an interaction between said one or more candidate substances and said protein complex,
   wherein said determining comprises determining whether a change in the passage of a marker substance across a biological membrane in which the protein complex is situated occurs, and when a change in the passage of the marker substance across the biological membrane is determined, the one or more candidate substances are identified as the channel modulators.

2. The method of claim 1, wherein the channel modulator is a channel agonist.

3. The method of claim 1, wherein the channel modulator is a channel antagonist.

4. The method of claim 1, wherein the biological membrane is provided by one or more cells or a cell line expressing one or more of the LRRC8A, LRRC8B, LRRC8C, LRRC8D and LRRC8E.

5. The method of claim 1, wherein the marker substance is an ion, an amino acid, an antibiotic, a cytotoxic substance and/or a fluorescent marker.

6. The method of claim 5, wherein the ion is chloride or iodide and/or the amino acid is a glutamate or taurine.

7. The method of claim 1, wherein the marker substance is iodide, taurine, chloride and/or glutamate.

8. The method of claim 4, wherein the cells or cell lines express a fluorescent protein variant, wherein the fluorescence of said fluorescent protein variant is modulated by presence of iodide and/or chloride, wherein said fluorescent protein variant is YFP(H148Q/I152L).

9. The method of claim 8, wherein one or more of LRRC8A, LRRC8B, LRRC8C, LRRC8D and/or LRRC8E function is disrupted or absent in one or more of said cells or cell lines.

10. The method of claim 9, wherein one or more of LRRC8A, LRRC8B, LRRC8C, LRRC8D and/ef LRRC8E function is disrupted or absent in one or more of said cells or cell lines as a result of deletion, mutation and/or antisense interference of a gene or other nucleic acid molecule encoding said protein.

11. The method of claim 8, wherein one or more of the LRRC8A, LRRC8B, LRRC8C, LRRC8D and LRRC8E is expressed from an exogenous nucleic acid in said cells or cell lines.

* * * * *

```
                         SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
acagtcagcc gcatcttctt                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gttaaaagca gccctggtga                                                     20

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gggttgaacc atgattccgg tgac                                                24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gaagacggca atcatcagca tgac                                                24

<210> SEQ ID NO 5
```

```
<211> LENGTH: 24
<212> TYPE: DNA
<213> ORGANISM: Artificial Sequence
<220> FEATURE:
<223> OTHER INFORMATION: Primer

<400> SEQUENCE: 5
acctggatgg cccacaggta atag                                              24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
atgctggtca actggaacct ctgc                                              24

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
acaagccatg agcagcgac                                                    19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggaatcatgt ttctccgggc                                                   20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
atggaggagt gaagtctcct gtcg                                              24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
cttccgcaag ggtaaacatt cctg                                              24

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
```
accgtggcca tgctcatgat tg                                          22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
atcttgtcct gtgtcacctg gag                                         23

<210> SEQ ID NO 13
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 13
ggctgatgta gaaggacgcc agg                                         23

<210> SEQ ID NO 14
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 14
tgatgattgc cgtcttcggg ggg                                         23

<210> SEQ ID NO 15
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 15
tcctgcaatg attcgttccg ggg                                         23

<210> SEQ ID NO 16
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 16
tttttctctt aacgcctcaa agg                                         23

<210> SEQ ID NO 17
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 17
ggccacaaaa tgctcgagcc tgg                                         23

<210> SEQ ID NO 18
<211> LENGTH: 23
<212> TYPE: DNA

```
<213> ORGANISM: Artificial Sequence
<220> FEATURE:
<223> OTHER INFORMATION: CRISPRICas Guide

<400> SEQUENCE: 18
atgctcatga tcggcgtgtt tgg                                              23

<210> SEQ ID NO 19
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 19
gtggctctga gaggtatgtc agg                                              23

<210> SEQ ID NO 20
<211> LENGTH: 23
<212> TYPE: DNA
<213> ORGANISM: Artificial Sequence
<220> FEATURE:
<223> OTHER INFORMATION: CRISPRICas Guide

<400> SEQUENCE: 20
gctggccgag tacctcaccg tgg                                              23

<210> SEQ ID NO 21
<211> LENGTH: 16
<212> TYPE: PRT
<213> ORGANISM: Homo sapiens

<400> SEQUENCE: 21

Gln Arg Thr Lys Ser Arg Ile Glu Gln Gly Ile Val Asp Arg Ser Glu
1               5                   10                  15

<210> SEQ ID NO 22
<211> LENGTH: 24
<212> TYPE: DNA
<213> ORGANISM: Artificial Sequence
<220> FEATURE:
<223> OTHER INFORMATION: mutated genome sequence

<400> SEQUENCE: 22
ctgatgattg ccgtcttcgg ggac                                             24

<210> SEQ ID NO 23
<211> LENGTH: 26
<212> TYPE: DNA
<213> ORGANISM: Mus musculus

<400> SEQUENCE: 23
ctgatgattg ccgtcttcgg ggggac                                           26
```

UNITED STATES PATENT AND TRADEMARK OFFICE
CERTIFICATE OF CORRECTION

PATENT NO. : 9,927,423 B2  
APPLICATION NO. : 14/642776  
DATED : March 27, 2018  
INVENTOR(S) : Thomas Jentsch et al.

Page 1 of 1

It is certified that error appears in the above-identified patent and that said Letters Patent is hereby corrected as shown below:

In the Specification

Column 3, Line 11, delete "LRRG8A and LRRG8E" and insert --LRRC8A and LRRC8E--, therefor.

Column 3, Lines 29-33, delete "Providing one or more LRRC8 proteins selected from LRRG8A, LRRG8B, LRRC8C, LRRG8D and LRRG8E, or a protein complex comprising one or more of LRRG8A, LRRG8B, LRRC8C, LRRG8D and/or LRRG8E;" and insert --Providing one or more LRRC8 proteins selected from LRRC8A, LRRC8B, LRRC8C, LRRC8D and LRRC8E, or a protein complex comprising one or more of LRRC8A, LRRC8B, LRRC8C, LRRC8D and/or LRRC8E;--, therefor.

Column 28, Line 22, Delete "E-well" and insert --6-well--, therefor.

In the Claims

Column 46, Line 59, in Claim 1, delete "and/or" and insert --and--, therefor.

Column 48, Line 7, in Claim 9, delete "and/or" and insert --and--, therefor.

Column 48, Line 11, in Claim 10, delete "and/ef" and insert --and--, therefor.

Signed and Sealed this  
Twenty-sixth Day of February, 2019

Andrei Iancu  
*Director of the United States Patent and Trademark Office*